US011805865B2

(12) United States Patent
Fiedler et al.

(10) Patent No.: US 11,805,865 B2
(45) Date of Patent: Nov. 7, 2023

(54) CLOSING DEVICE HAVING A WINDING ELEMENT

(71) Applicant: Fidlock GmbH, Hannover (DE)

(72) Inventors: Joachim Fiedler, Hannover (DE); Breido Botkus, Hannover (DE); Heiko Buettner, Hannover (DE)

(73) Assignee: Fidlock GmbH, Hannover (DE)

( * ) Notice: Subject to any disclaimer, the term of this patent is extended or adjusted under 35 U.S.C. 154(b) by 0 days.

(21) Appl. No.: 17/731,582

(22) Filed: Apr. 28, 2022

(65) Prior Publication Data

US 2022/0248810 A1 Aug. 11, 2022

Related U.S. Application Data

(63) Continuation of application No. 16/461,136, filed as application No. PCT/EP2018/054968 on Feb. 28, 2018, now Pat. No. 11,344,086.

(30) Foreign Application Priority Data

Feb. 28, 2017 (DE) .................... 10 2017 203 263.4
Nov. 14, 2017 (DE) .................... 10 2017 220 304.8
Jan. 23, 2018 (DE) .................... 10 2018 201 019.6

(51) Int. Cl.
*A44B 99/00* (2010.01)
*A45C 13/10* (2006.01)
*A43C 11/16* (2006.01)

(52) U.S. Cl.
CPC .......... *A44B 99/00* (2013.01); *A45C 13/1038* (2013.01); *A43C 11/165* (2013.01); *A44D 2203/00* (2013.01)

(58) Field of Classification Search
CPC ... A44B 99/00; A44B 11/258; A45C 13/1038; A45C 11/165; A45C 13/1046; A44D 2203/00; A42B 3/145; A41D 13/06; A43C 1/06; A43C 7/005; A61F 5/01; A61F 5/0111; A61F 5/055; A61F 2013/00978; A45F 2005/006; A45F 2200/0516; A45F 5/004; E06B 2009/425; E06B 9/42
See application file for complete search history.

(56) References Cited

U.S. PATENT DOCUMENTS

| 7,076,843 B2 | 7/2006 | Sakabayashi |
| 8,052,459 B2 | 11/2011 | Smith et al. |
| 8,353,544 B2 | 1/2013 | Fiedler |

(Continued)

FOREIGN PATENT DOCUMENTS

| CN | 1618363 A | 5/2005 |
| CN | 201360619 Y | 12/2009 |

(Continued)

*Primary Examiner* — Robert Sandy
*Assistant Examiner* — Louis A Mercado
(74) *Attorney, Agent, or Firm* — THE WEBB LAW FIRM

(57) ABSTRACT

A fastener device includes a first fastener part and a second fastener part which can be mounted on one another along a closing direction and are held against one another in a closed position, and are releasable from one another in order to open the fastener device. The second fastener part has a winding element on which a tension element can be arranged and which is rotatable relative to the first fastener part in order to wind up the tension element on the winding element in a winding direction.

18 Claims, 76 Drawing Sheets

(56) References Cited

U.S. PATENT DOCUMENTS

| | | |
|---|---|---|
| 8,910,353 B2 | 12/2014 | Polegato Moretti |
| 8,914,951 B2 | 12/2014 | Gaudillere et al. |
| 9,072,341 B2 | 7/2015 | Jungkind |
| 9,635,906 B2 | 5/2017 | Midorikawa |
| 9,706,814 B2 | 7/2017 | Converse et al. |
| 9,717,323 B2 * | 8/2017 | Tsai .................. A45F 5/004 |
| 9,770,070 B2 | 9/2017 | Cotterman et al. |
| 10,143,270 B2 | 12/2018 | Fiedler et al. |
| 10,212,993 B2 | 2/2019 | Fiedler et al. |
| 10,264,852 B2 | 4/2019 | Kim et al. |
| 10,285,472 B2 | 5/2019 | Wyatt et al. |
| 10,492,568 B2 | 12/2019 | Burns et al. |
| 10,702,409 B2 | 7/2020 | Burns et al. |
| 10,874,175 B2 | 12/2020 | So |
| 10,959,492 B2 | 3/2021 | Converse et al. |
| 11,109,644 B2 * | 9/2021 | Fiedler .................. F16B 21/02 |
| 2001/0024039 A1 | 9/2001 | Lippoldt et al. |
| 2003/0020288 A1 | 1/2003 | Jungkind et al. |
| 2003/0122342 A1 | 7/2003 | Germano et al. |
| 2003/0204938 A1 | 11/2003 | Hammerslag |
| 2005/0098673 A1 | 5/2005 | Huang |
| 2005/0167946 A1 | 8/2005 | Rampp |
| 2005/0247813 A1 | 11/2005 | Kovacevich et al. |
| 2007/0271738 A1 | 11/2007 | Yang |
| 2009/0172928 A1 * | 7/2009 | Messmer .................. A43C 7/00 242/407.1 |
| 2009/0255486 A1 | 10/2009 | Thompson et al. |
| 2010/0283269 A1 | 11/2010 | Fiedler |
| 2010/0287741 A1 | 11/2010 | Fiedler |
| 2010/0308605 A1 | 12/2010 | Fiedler |
| 2011/0030174 A1 | 2/2011 | Fiedler |
| 2011/0131770 A1 | 6/2011 | Fiedler |
| 2011/0138583 A1 | 6/2011 | Fiedler |
| 2011/0167543 A1 | 7/2011 | Kovacevich et al. |
| 2011/0266384 A1 | 11/2011 | Goodman et al. |
| 2014/0290016 A1 | 10/2014 | Lovett et al. |
| 2015/0007422 A1 | 1/2015 | Cavanagh et al. |
| 2015/0014463 A1 | 1/2015 | Converse et al. |
| 2015/0076272 A1 | 3/2015 | Trudel et al. |
| 2015/0135486 A1 | 5/2015 | Fiedler et al. |
| 2016/0113381 A1 | 4/2016 | Tsai |
| 2016/0354223 A1 | 12/2016 | Burns et al. |
| 2017/0127764 A1 | 5/2017 | Fiedler |
| 2017/0303643 A1 | 10/2017 | Converse et al. |
| 2018/0035761 A1 | 2/2018 | Midorikawa |
| 2018/0319617 A1 | 11/2018 | Kim |
| 2018/0363689 A1 * | 12/2018 | Richter .................. F16M 13/02 |
| 2019/0144150 A1 | 5/2019 | Chen |

FOREIGN PATENT DOCUMENTS

| | | |
|---|---|---|
| CN | 101843388 A | 9/2010 |
| CN | 102326922 A | 1/2012 |
| CN | 103153112 A | 6/2013 |
| CN | 103476288 A | 12/2013 |
| CN | 103899611 A | 7/2014 |
| CN | 203676303 U | 7/2014 |
| CN | 203913633 U | 11/2014 |
| CN | 204070830 U | 1/2015 |
| CN | 104394730 A | 3/2015 |
| CN | 104853636 A | 8/2015 |
| CN | 206213402 U | 6/2017 |
| CN | 107205524 A | 9/2017 |
| DE | 102013203440 A1 | 8/2014 |
| EP | 0693260 A2 | 1/1996 |
| EP | 1259134 B1 | 11/2005 |
| FR | 2500878 A1 | 9/1982 |
| GB | 2480622 A | 11/2011 |
| JP | 7208 A | 1/1995 |
| JP | 2013122319 A | 6/2013 |
| JP | 2015293 A | 1/2015 |
| JP | 2016520401 A | 7/2016 |
| WO | 2007016983 A1 | 2/2007 |
| WO | 2008006354 A2 | 1/2008 |
| WO | 2008006356 A2 | 1/2008 |
| WO | 2008006357 A2 | 1/2008 |
| WO | 2009010049 A2 | 1/2009 |
| WO | 2009092368 A2 | 7/2009 |
| WO | 2009127196 A2 | 10/2009 |
| WO | 2010006594 A2 | 1/2010 |
| WO | 2014090926 A1 | 6/2014 |
| WO | 2014180512 A1 | 11/2014 |
| WO | 2015006616 A1 | 1/2015 |
| WO | 2017000013 A1 | 1/2017 |

\* cited by examiner

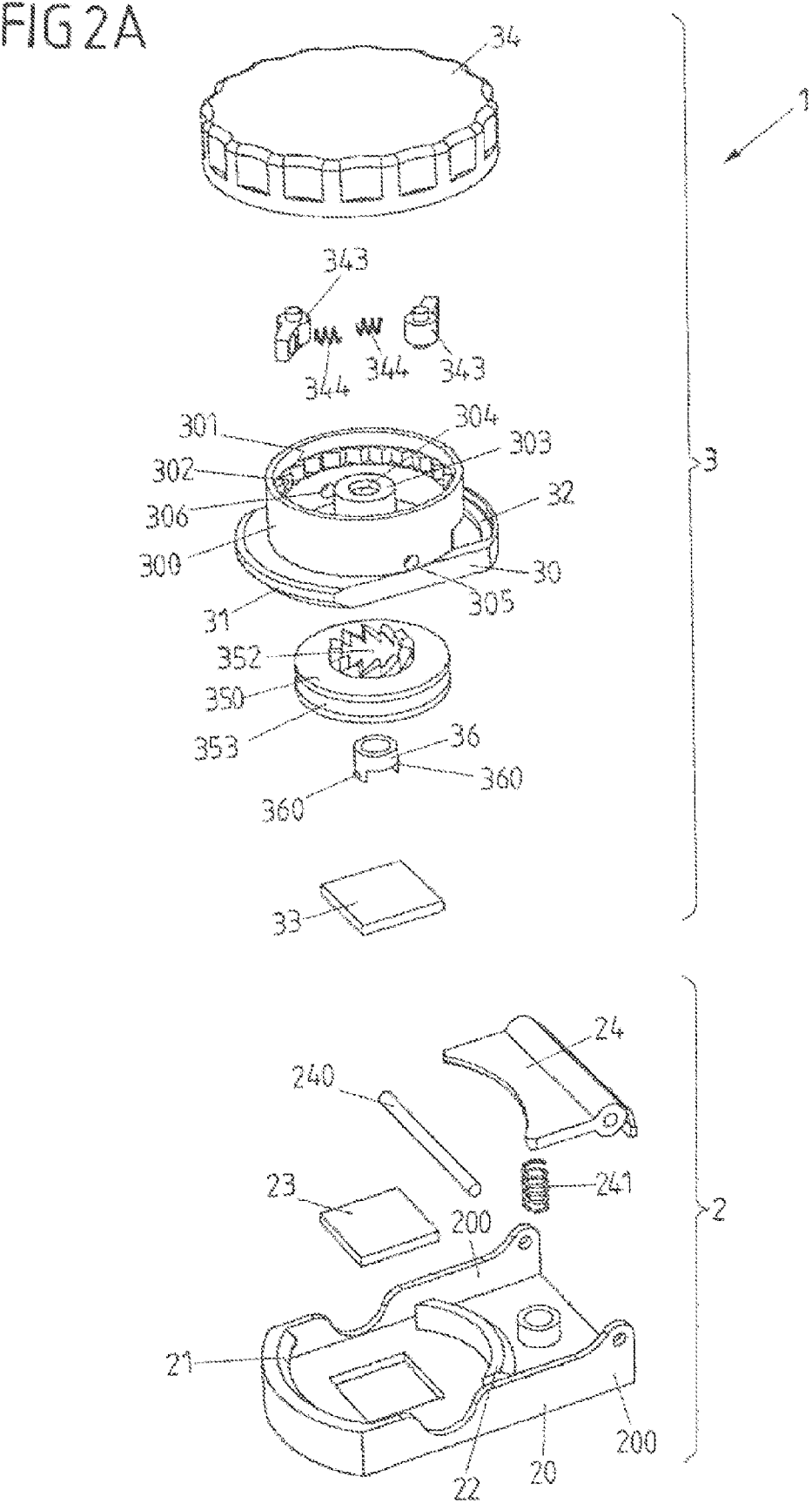

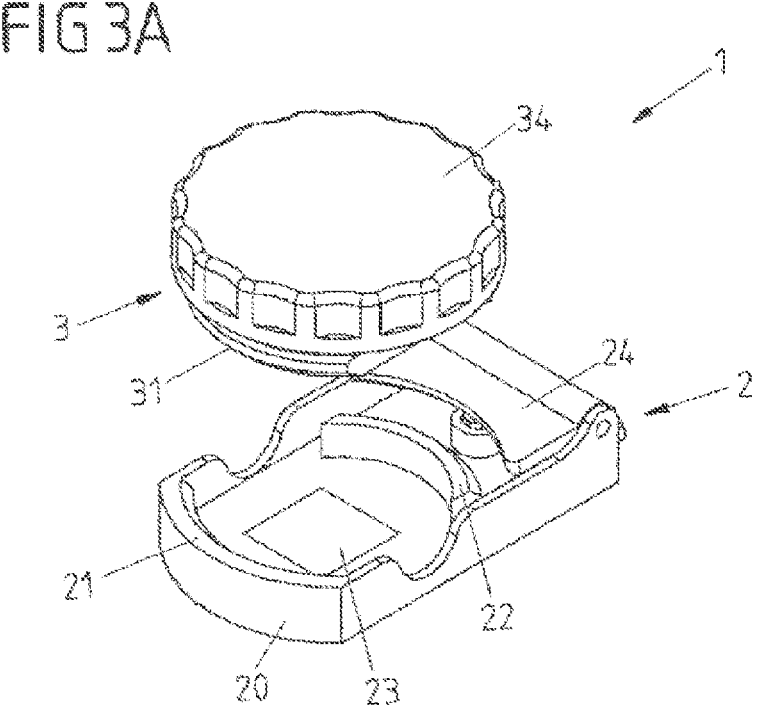
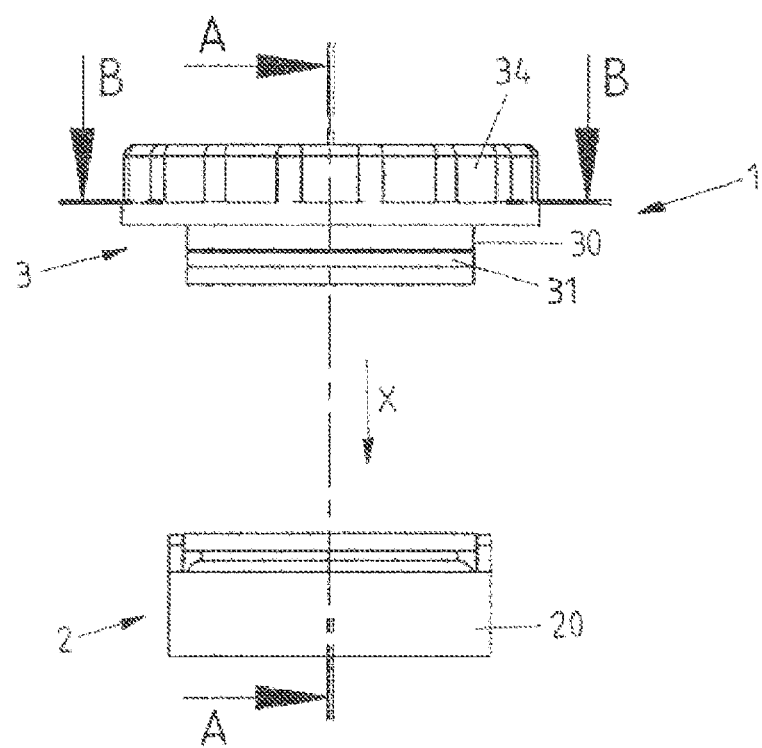

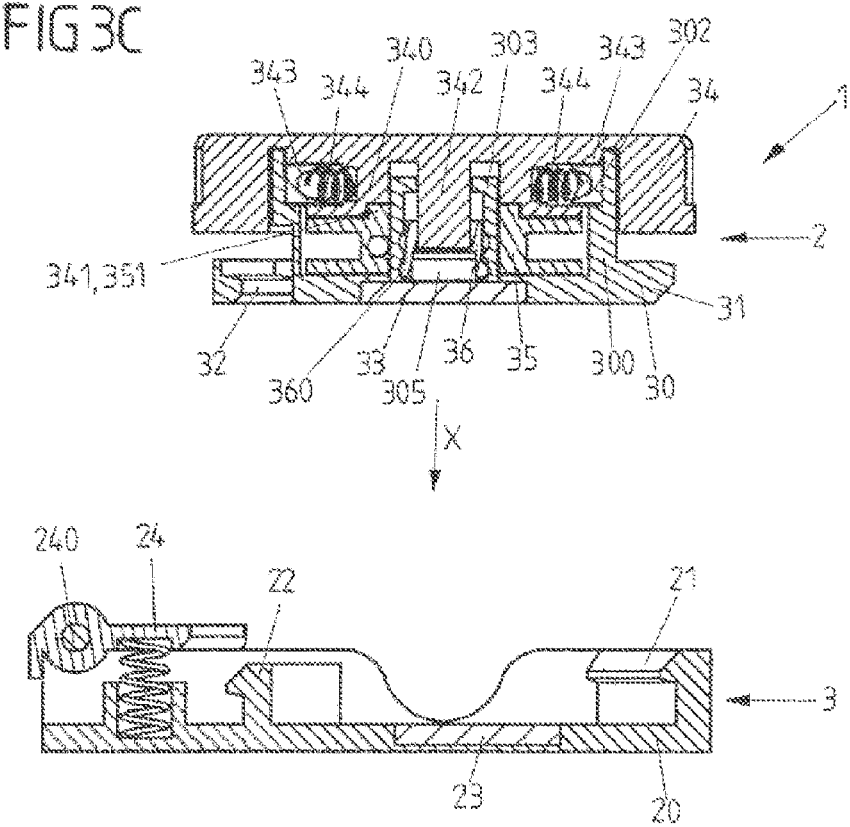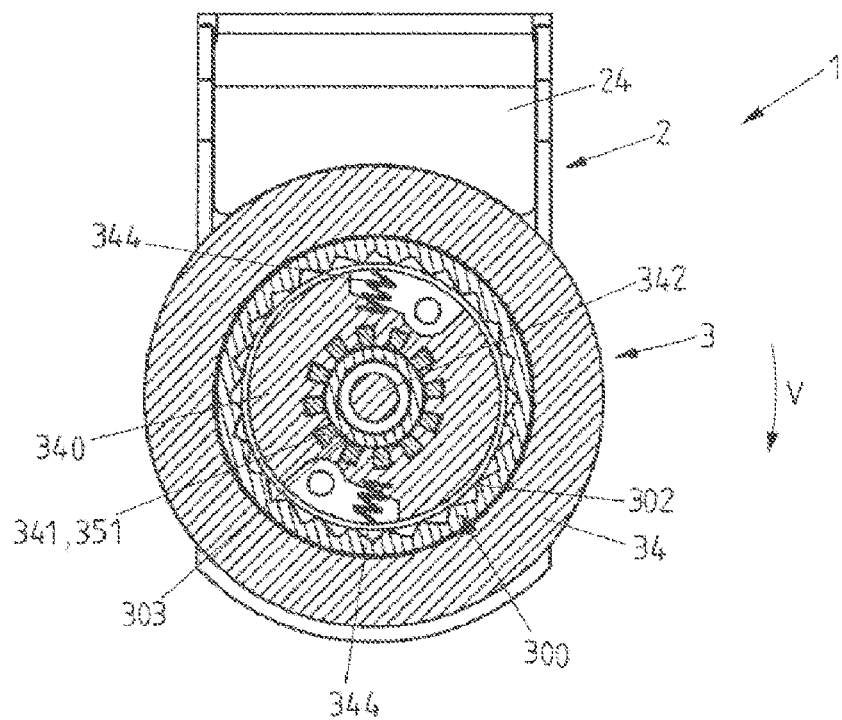

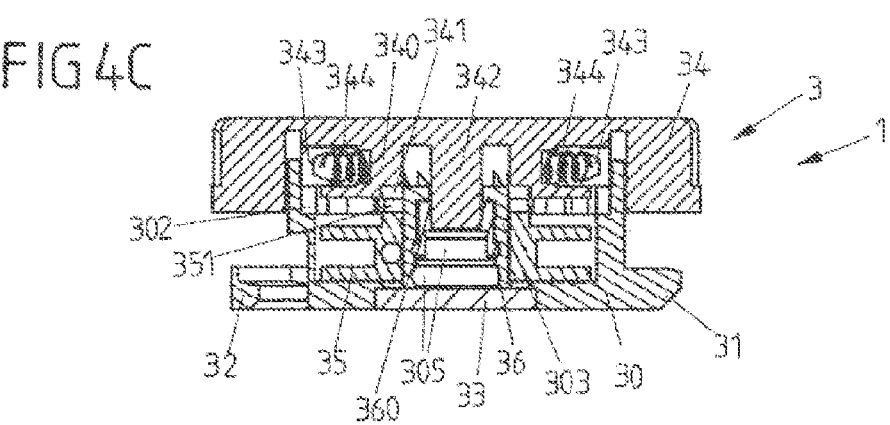
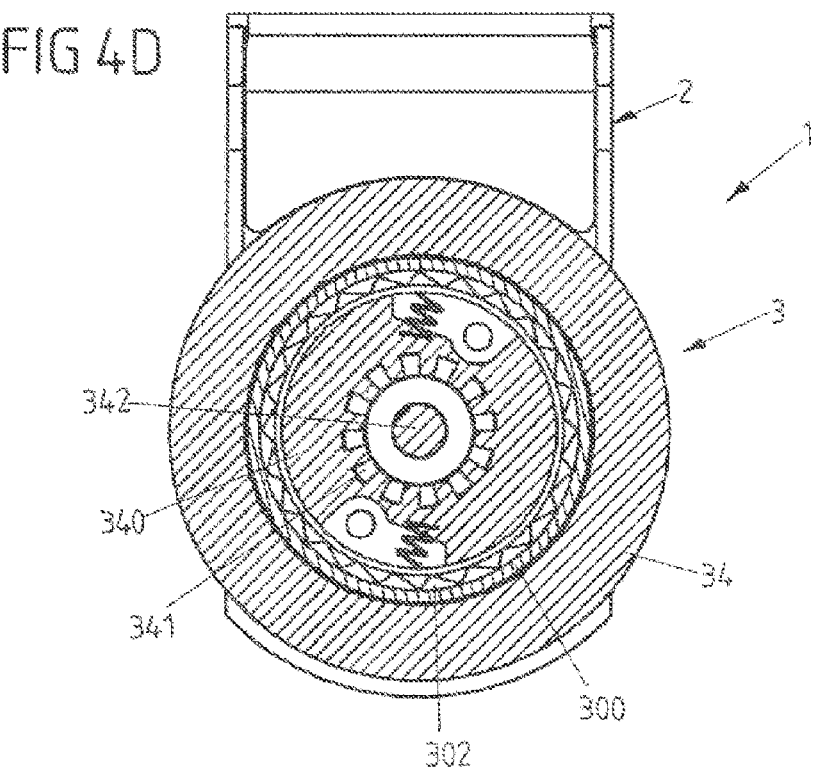

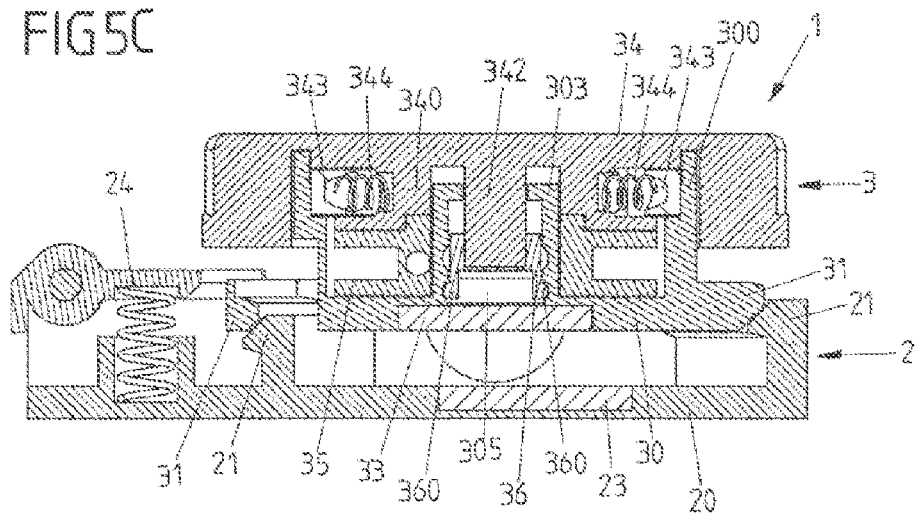
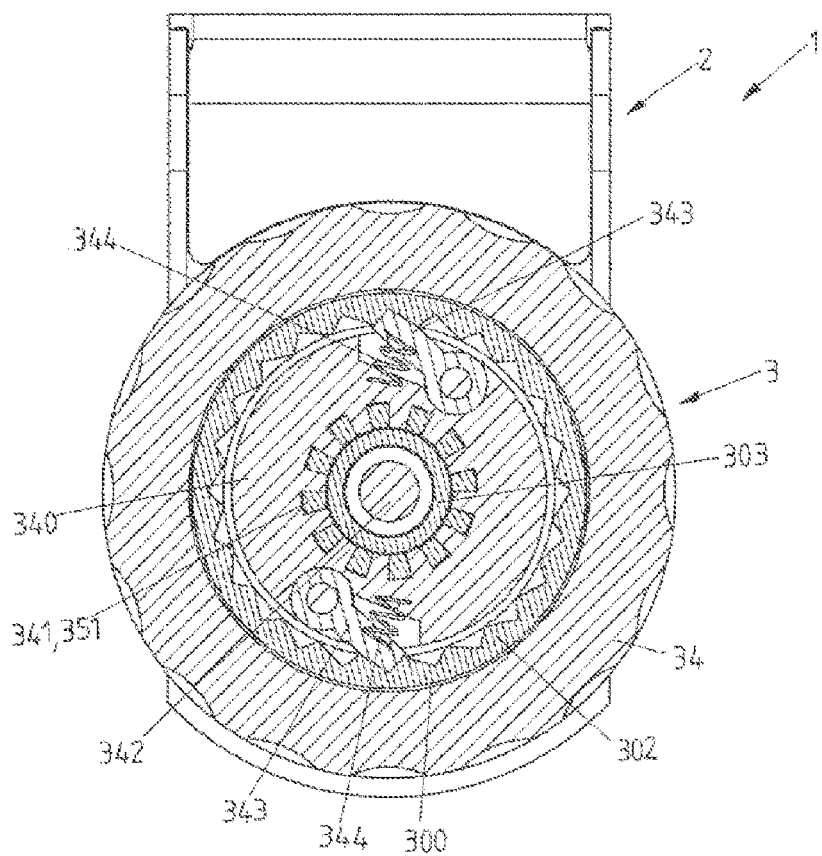

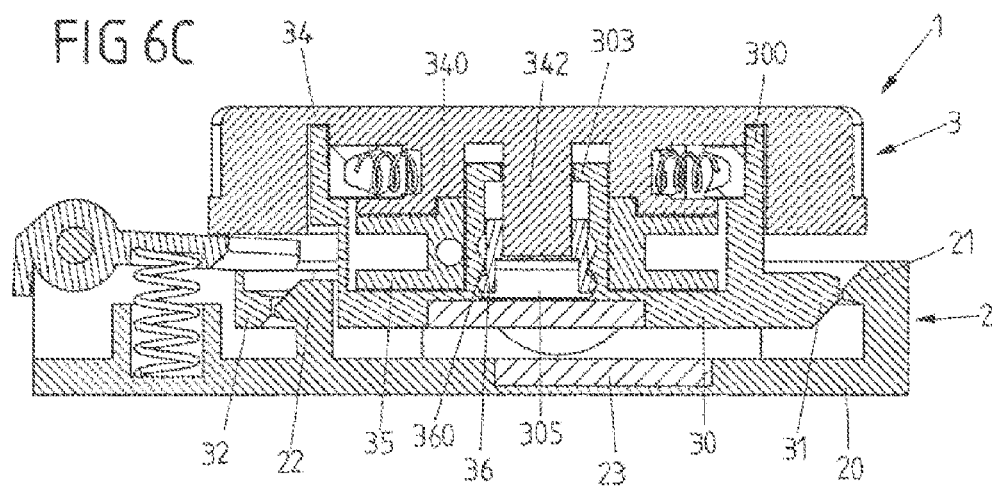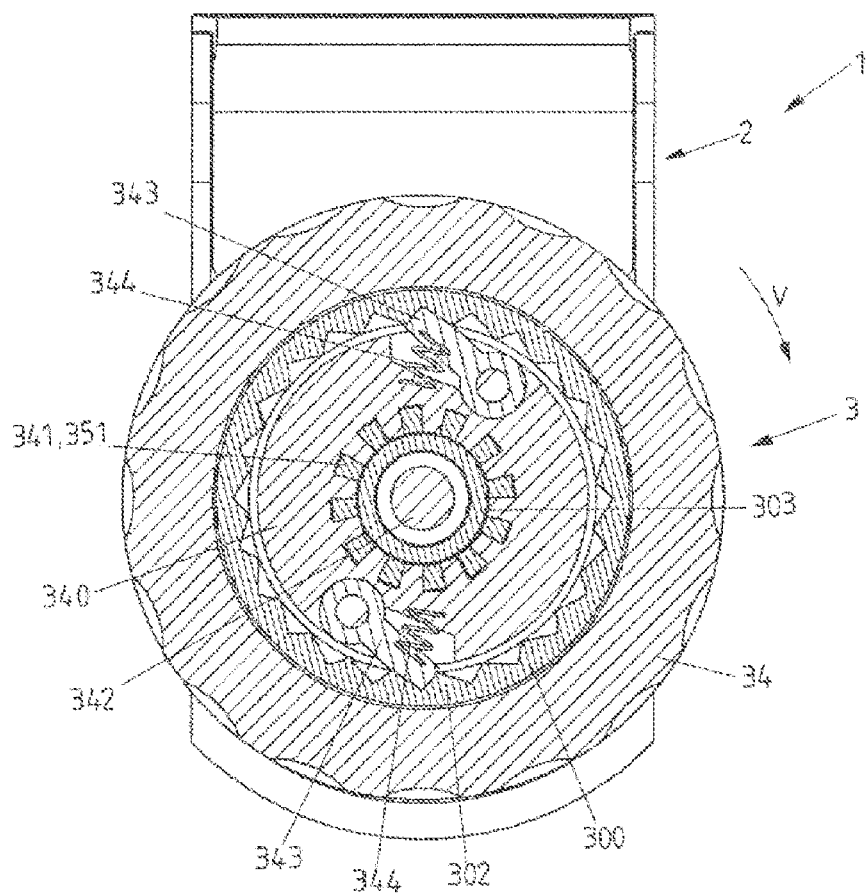

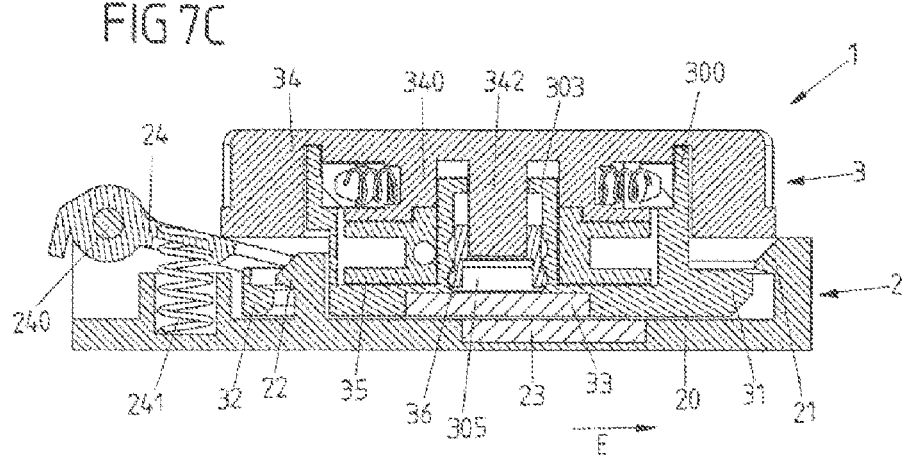
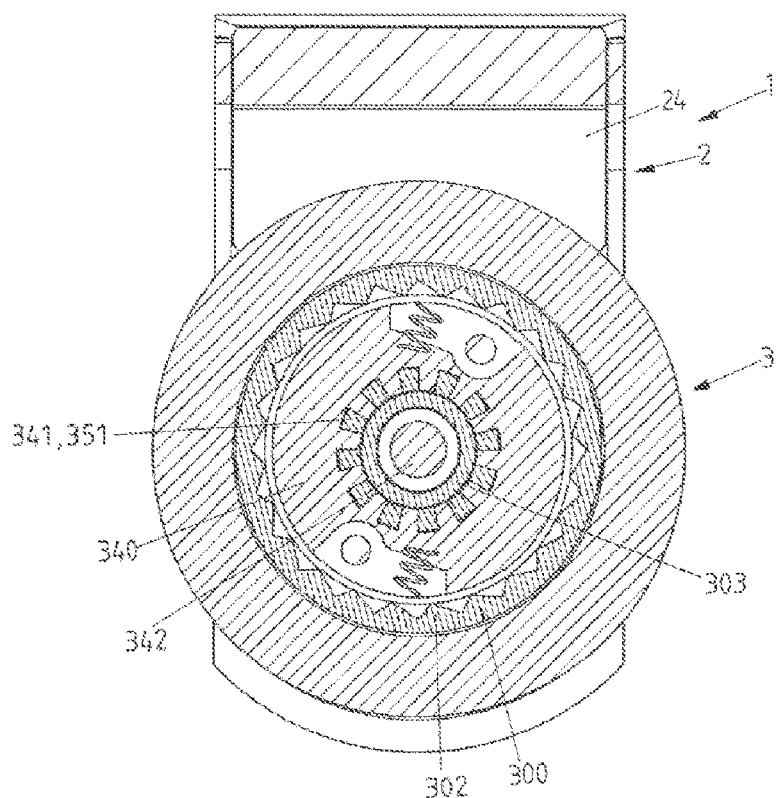

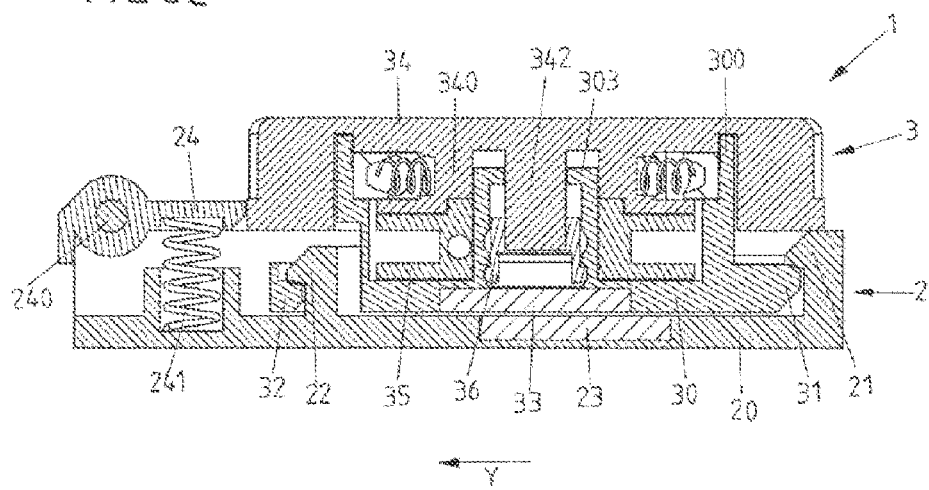
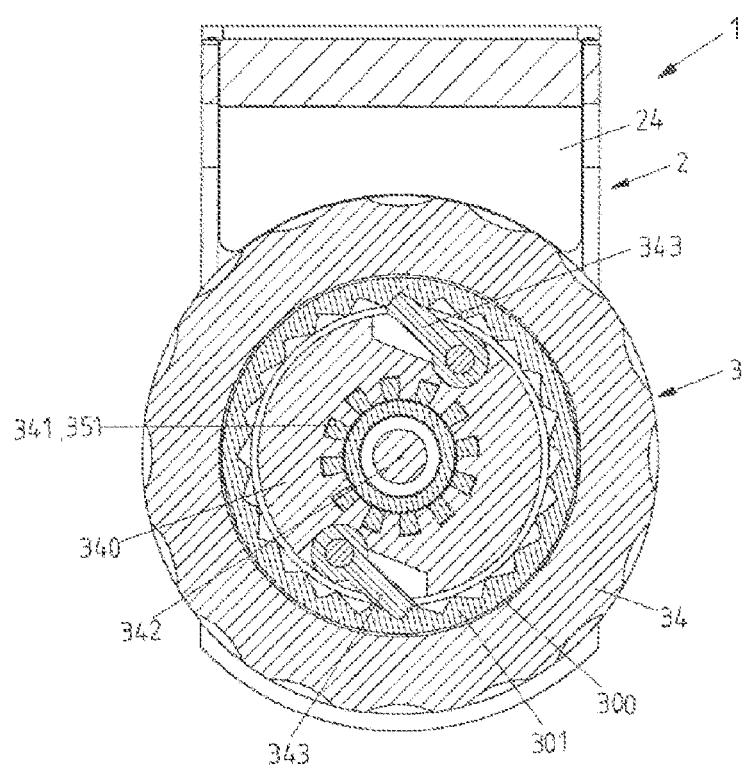

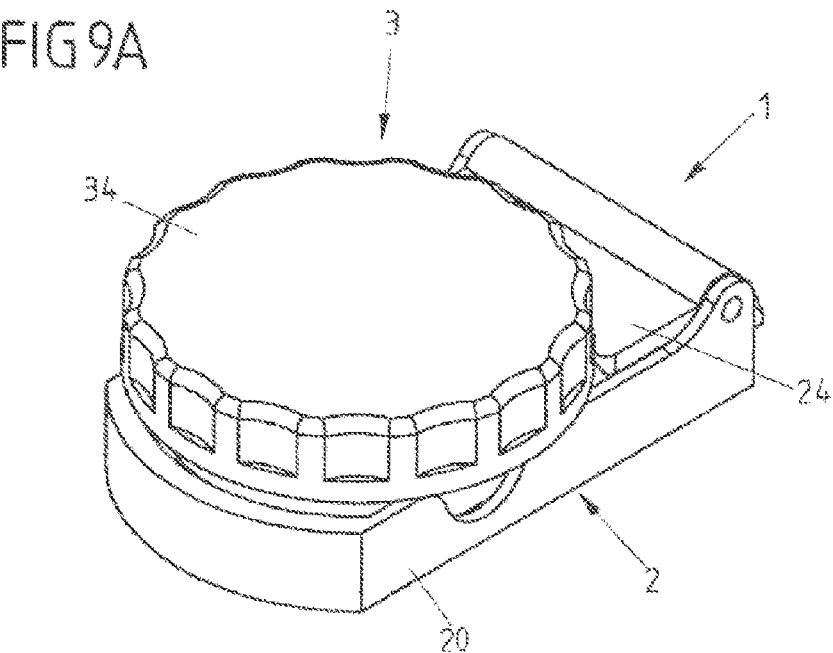
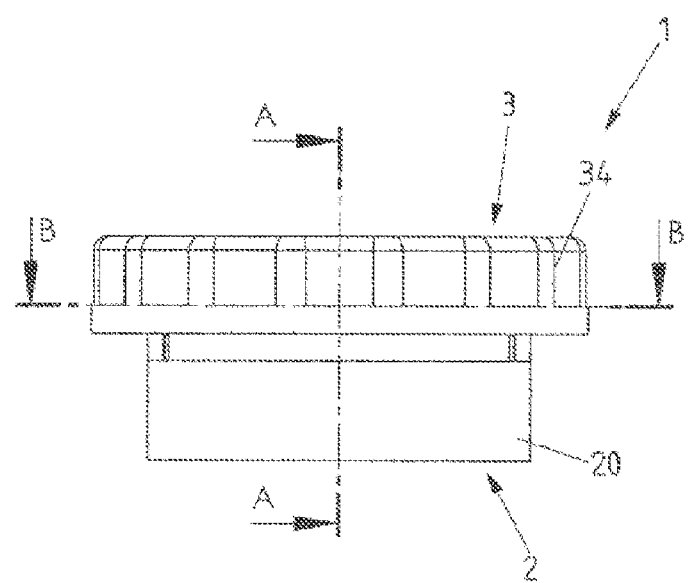

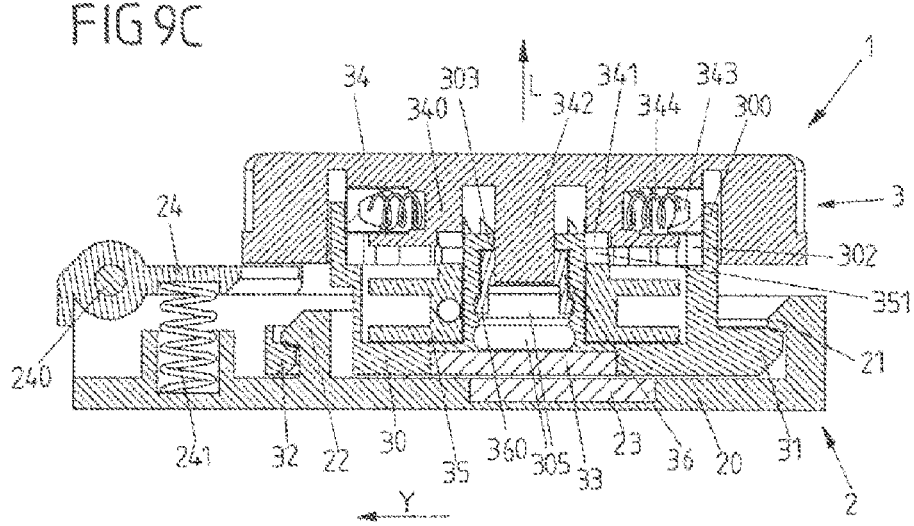
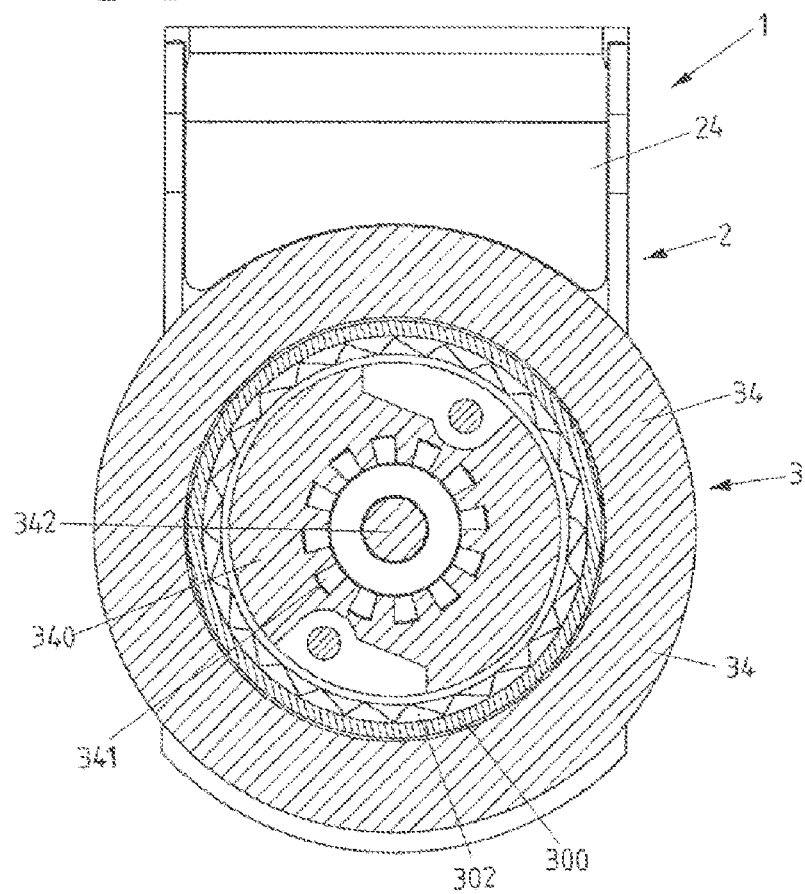

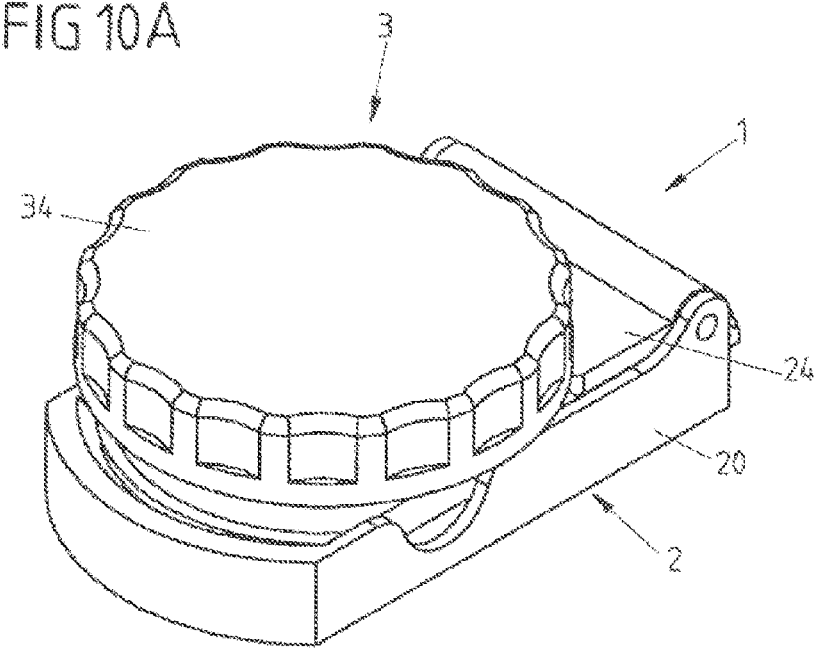
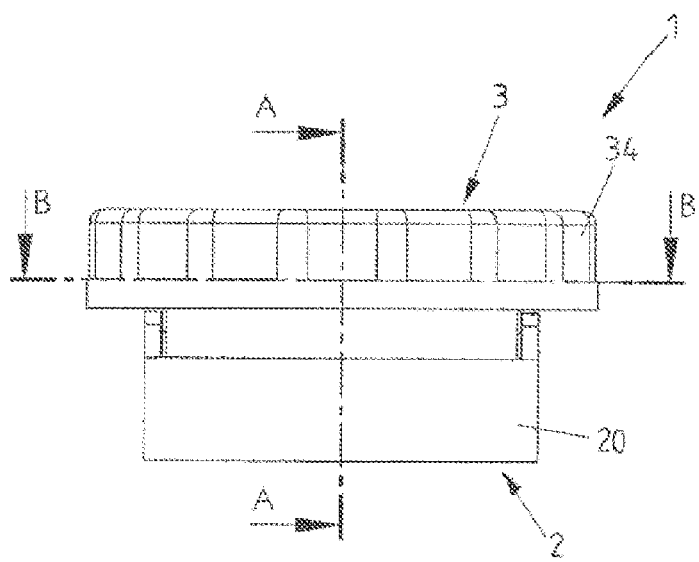

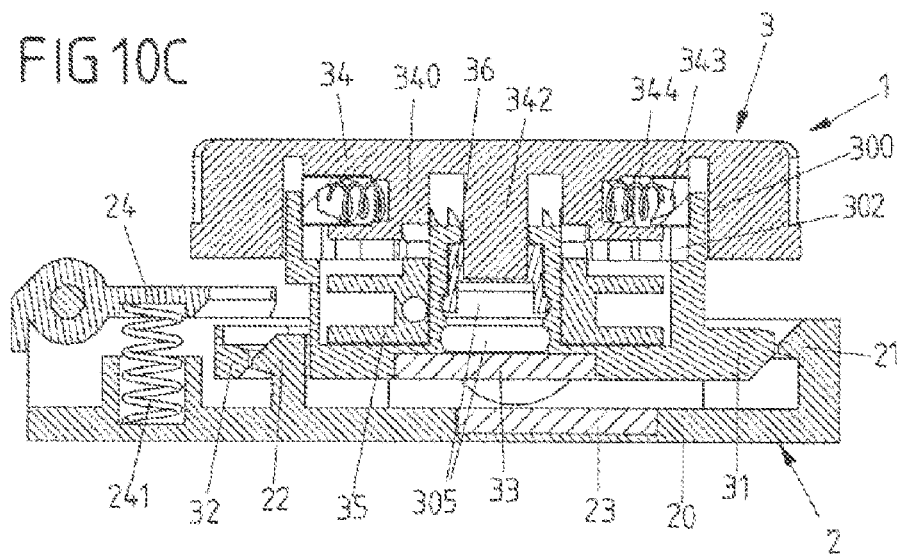
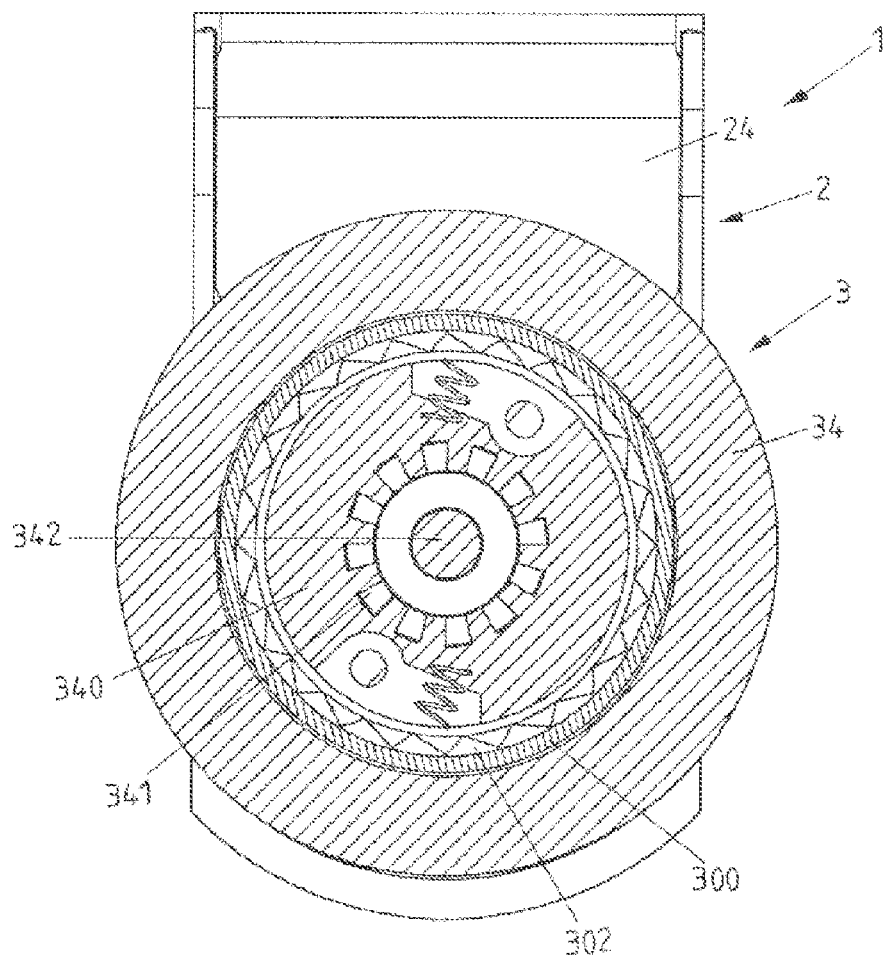

FIG 11A
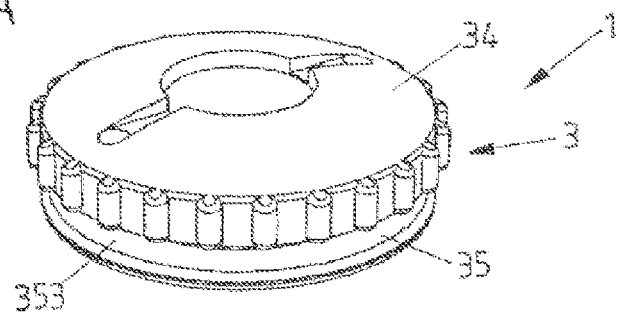
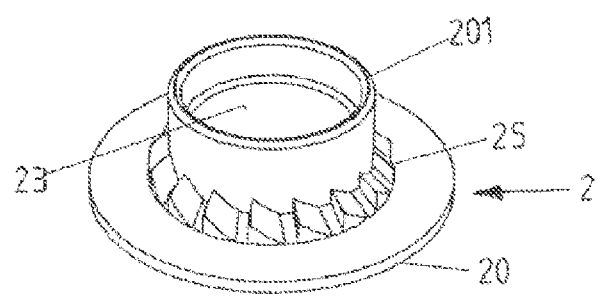
FIG 11B
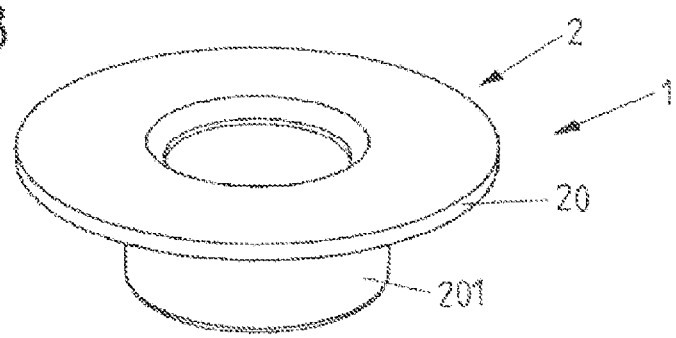
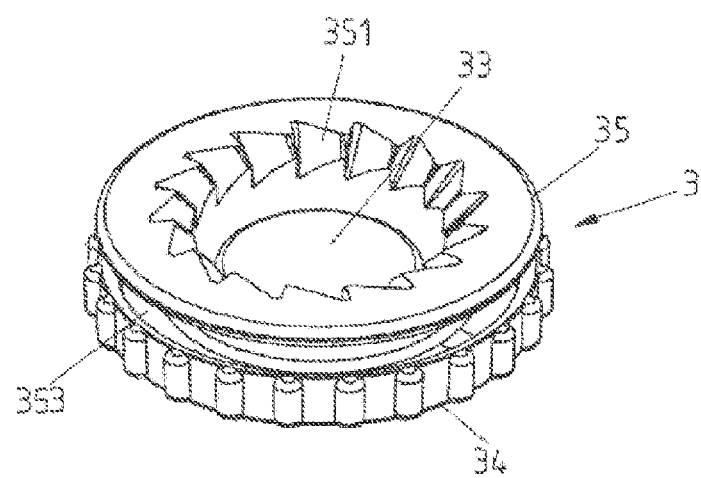

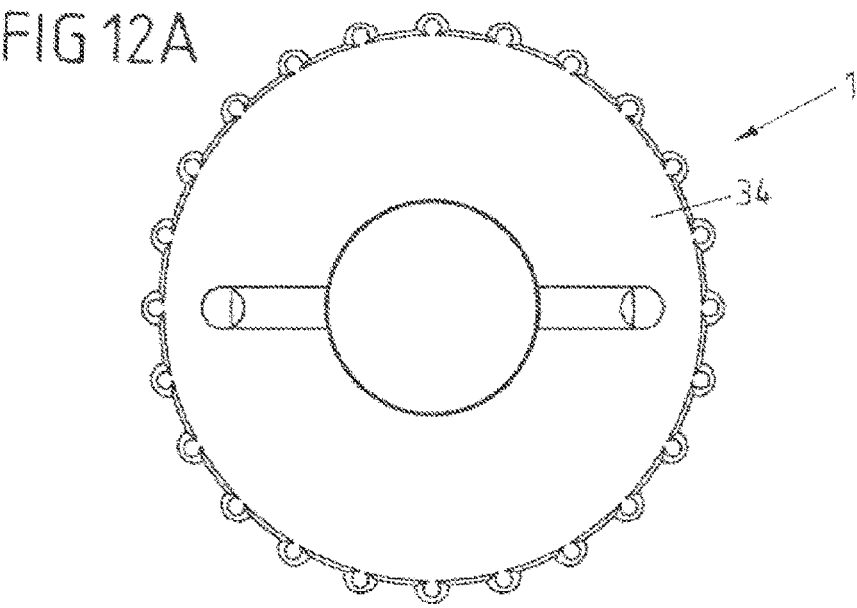
FIG 12A
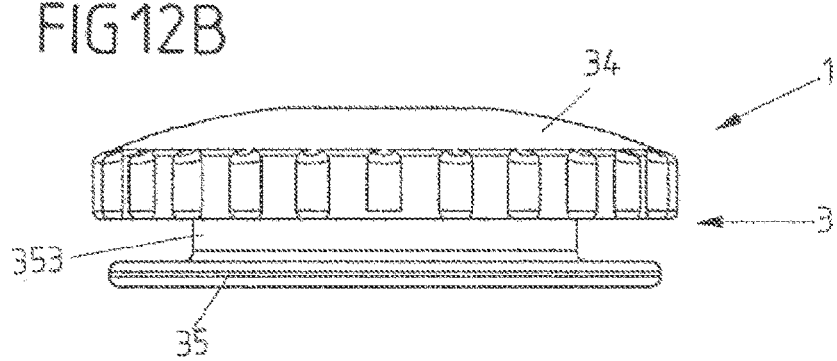
FIG 12B
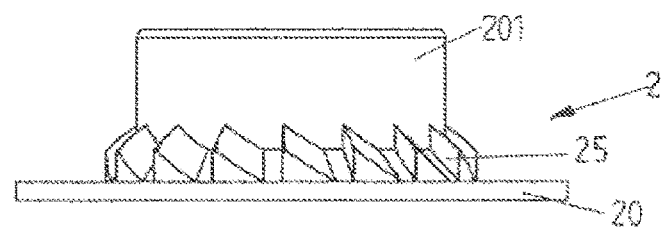

FIG 13B
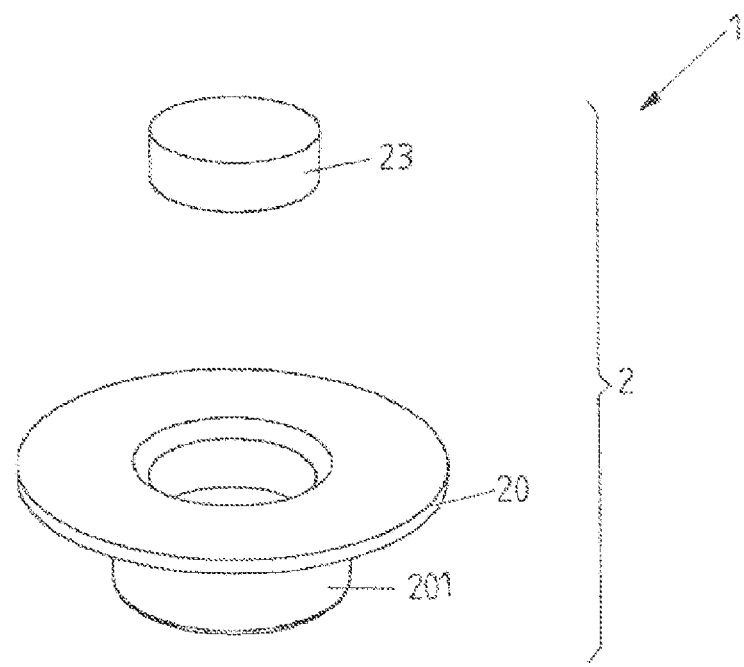
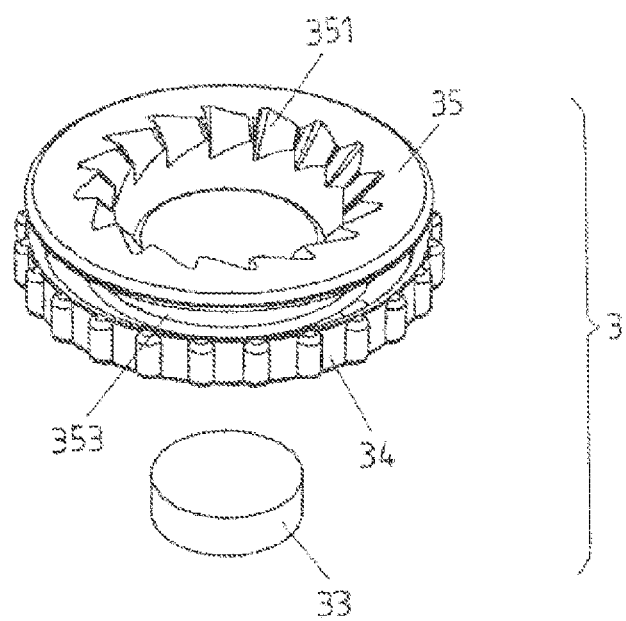

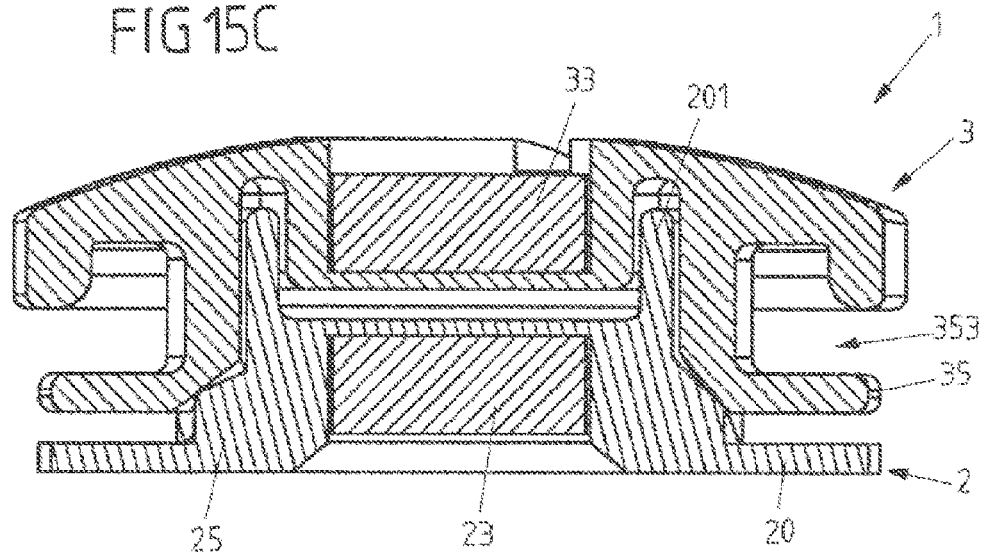
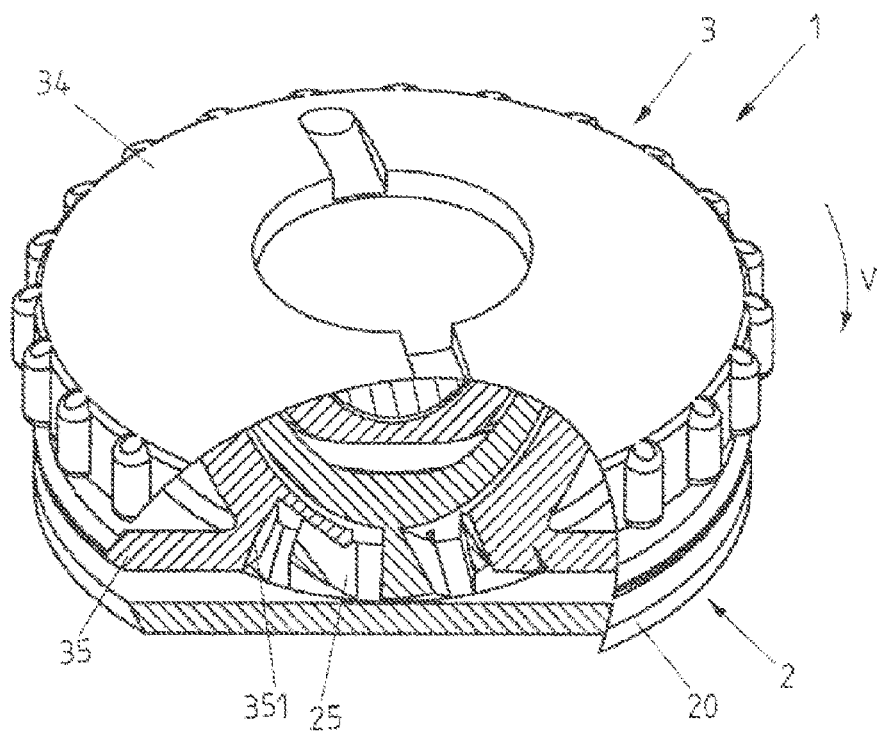

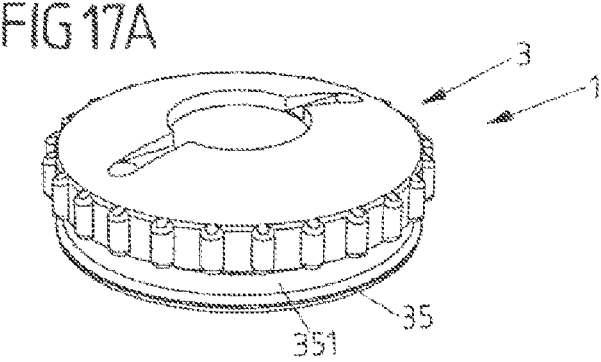
FIG 17A
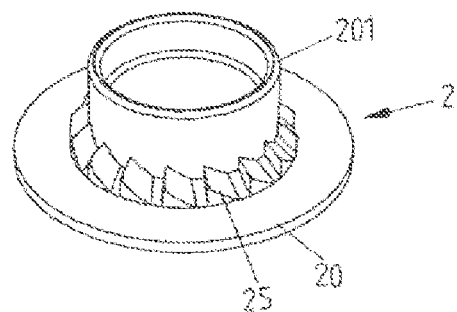
FIG 17B
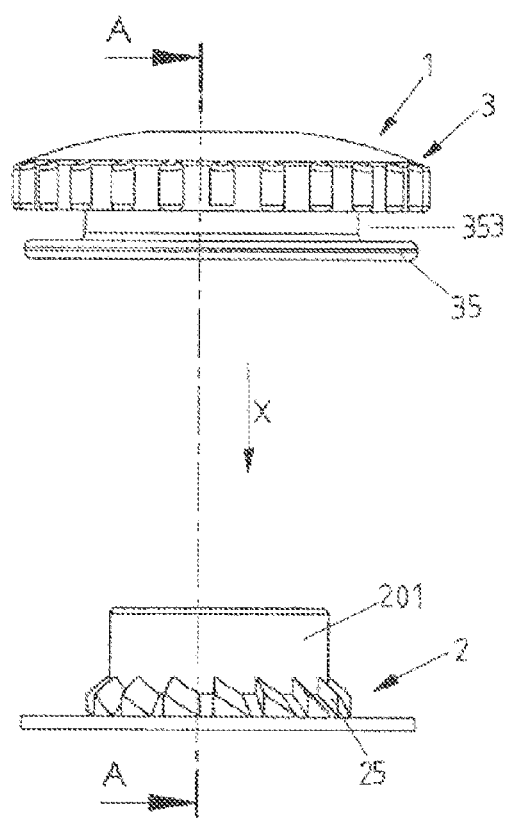

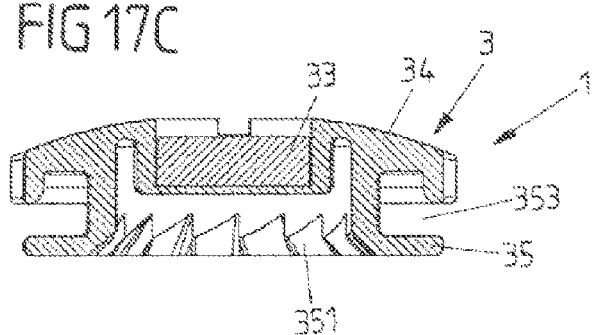
FIG 17C
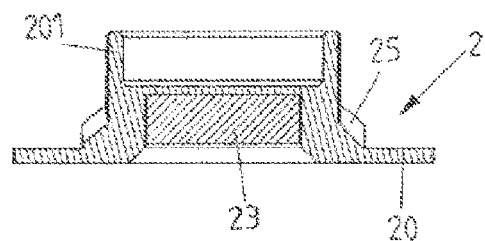
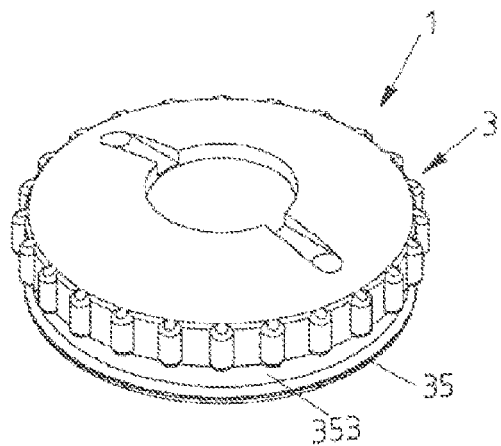
FIG 17D
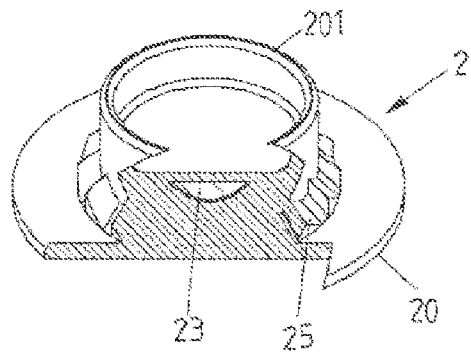

FIG 18A
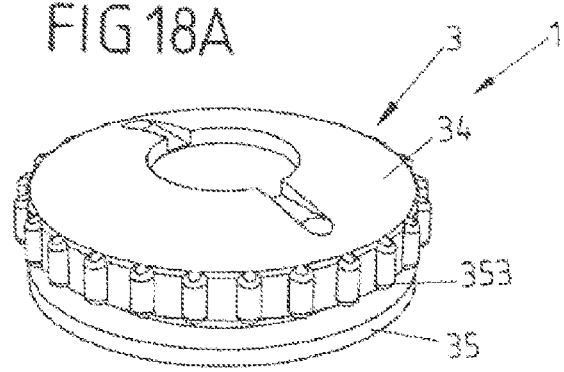
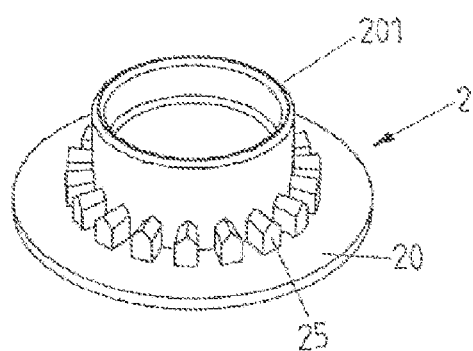
FIG 18B
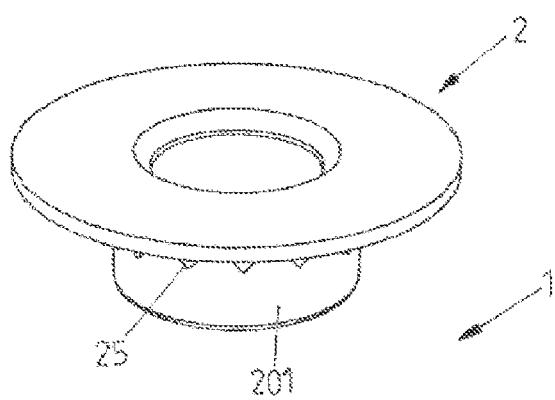
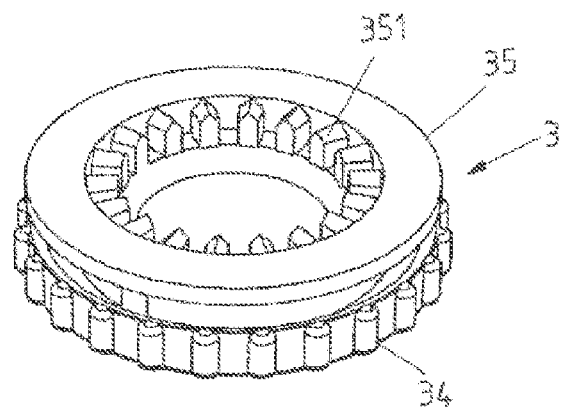

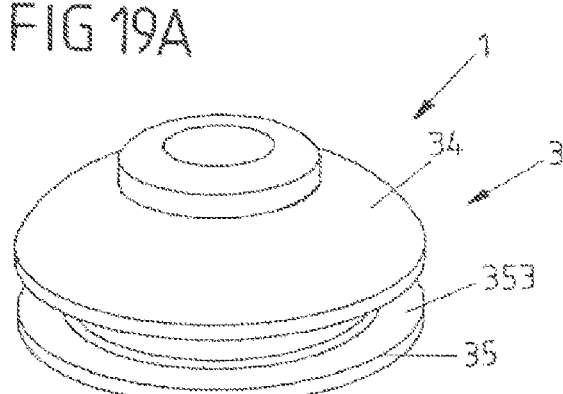
FIG 19A
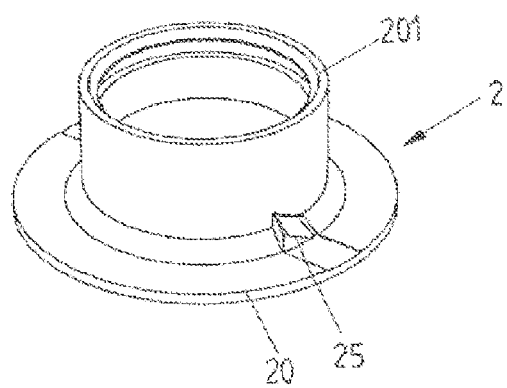
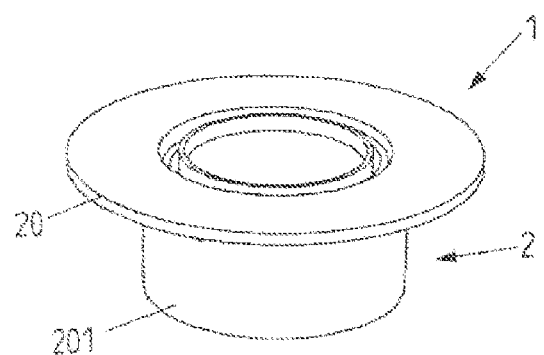
FIG 19B
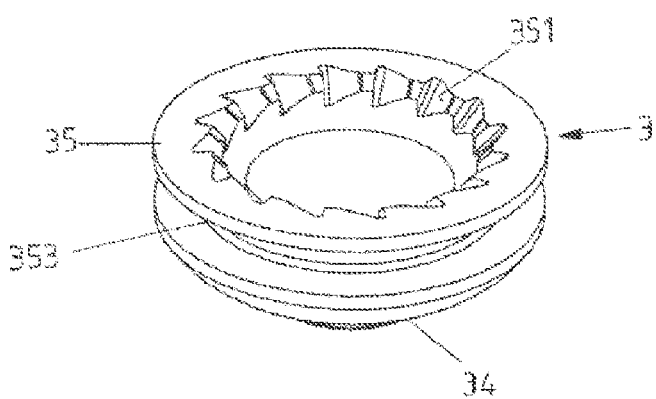

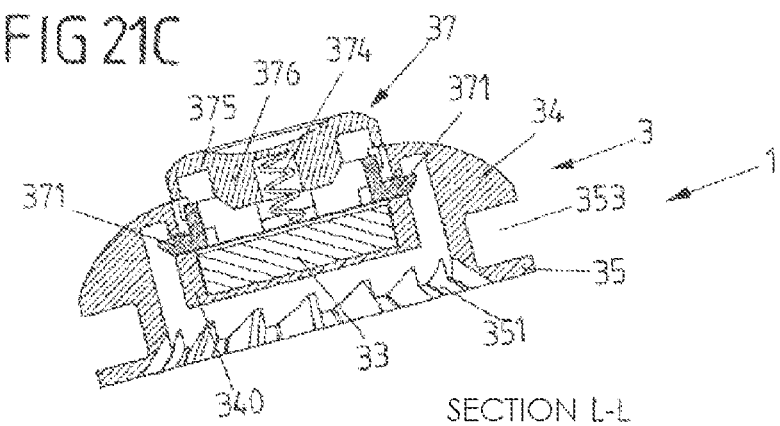
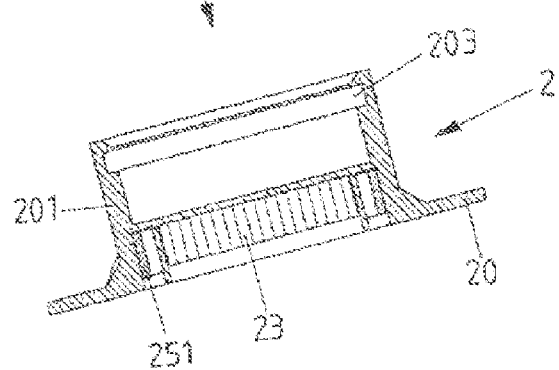
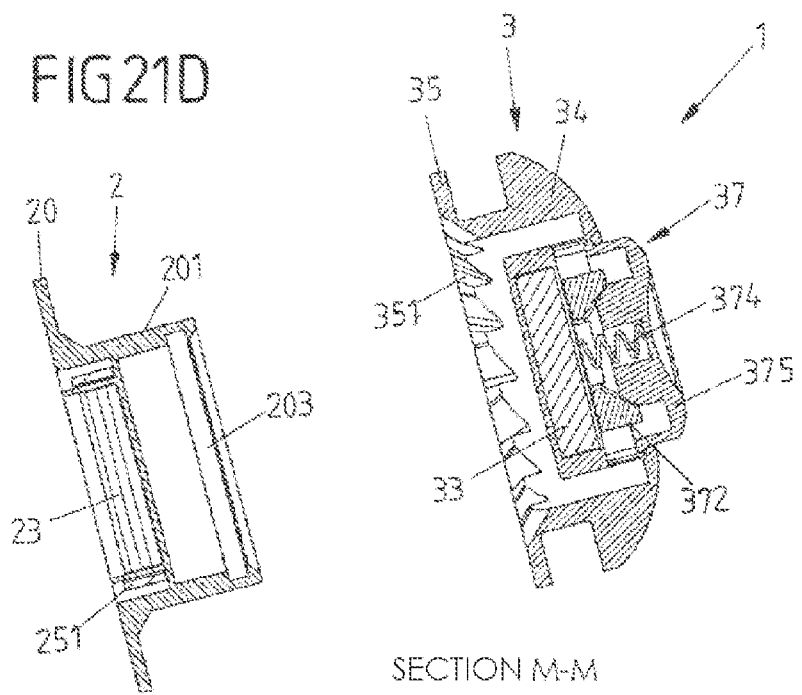

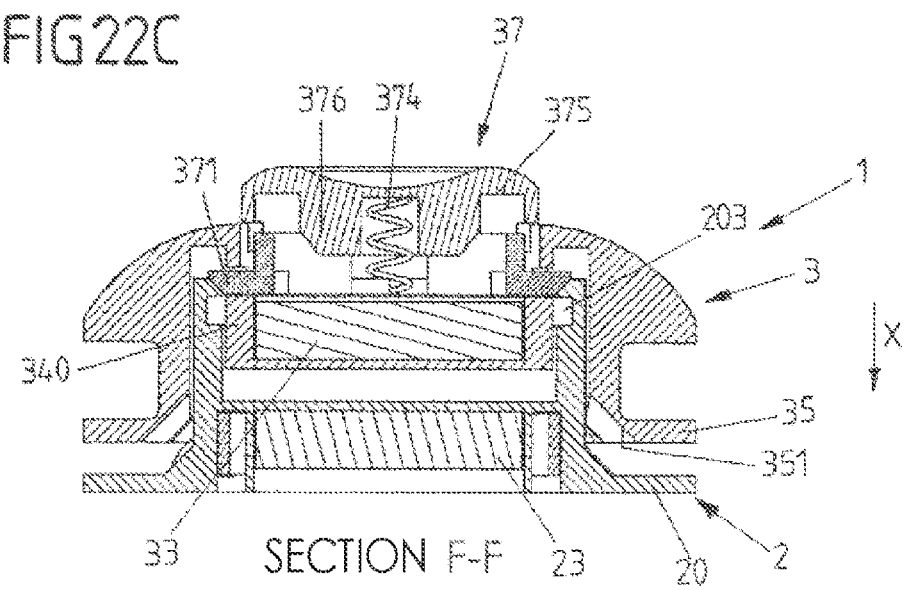
FIG 22C SECTION F-F
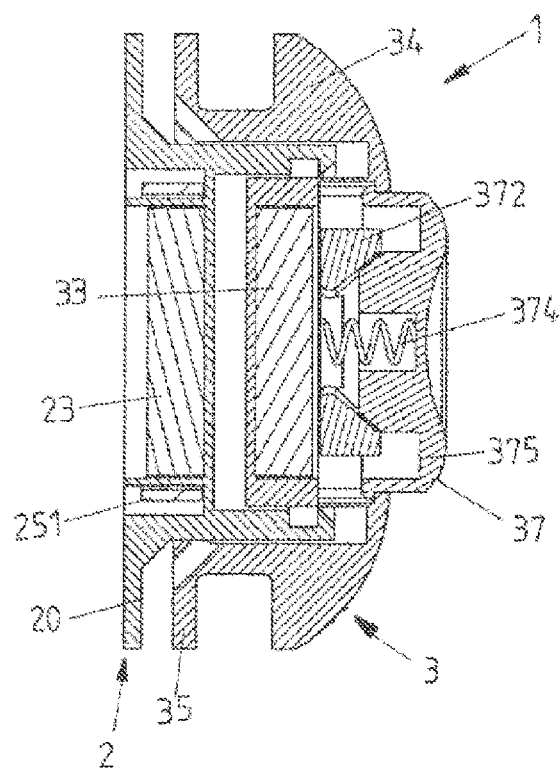
FIG 22D SECTION G-G

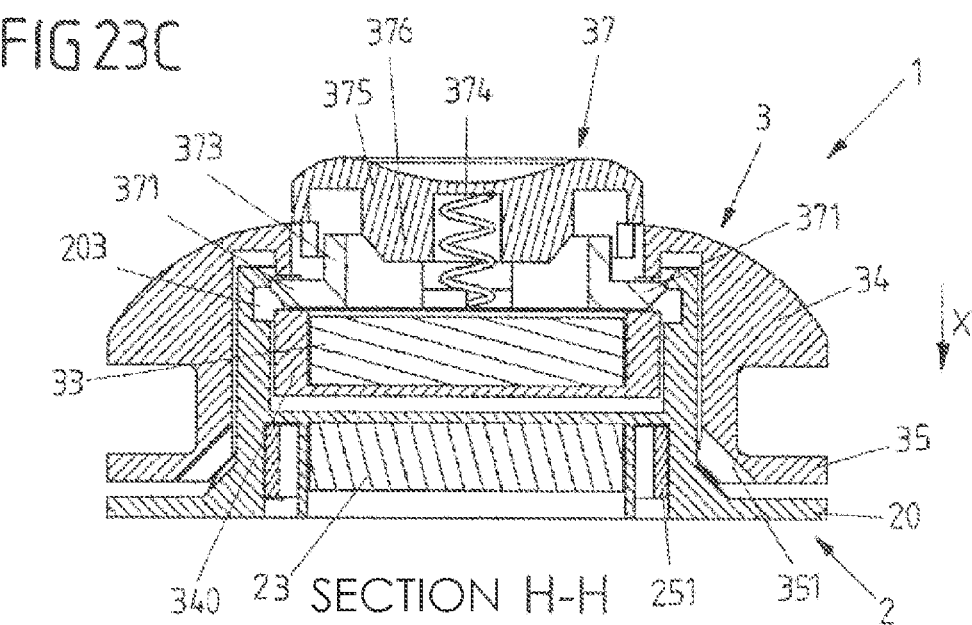
FIG 23C SECTION H-H
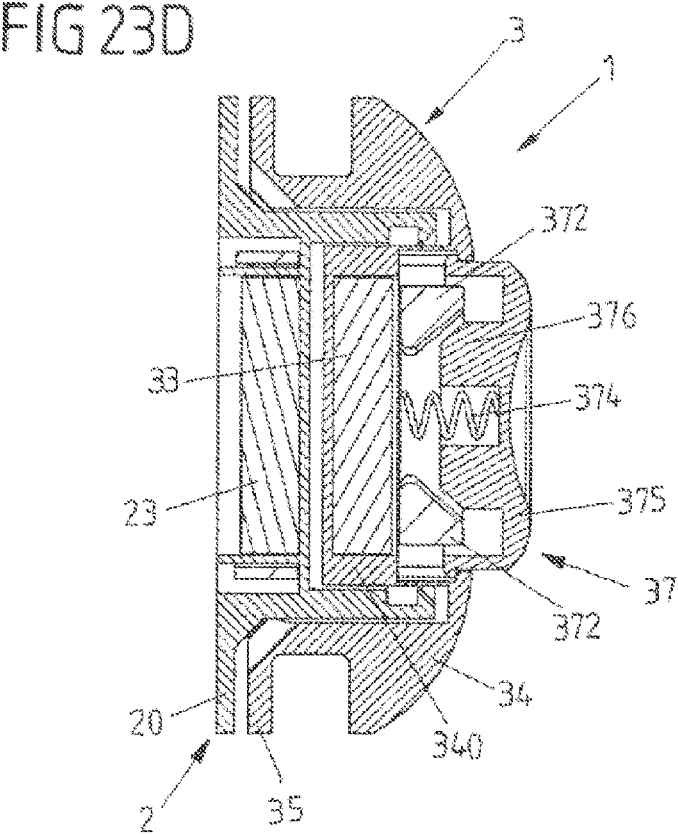
FIG 23D SECTION I-I

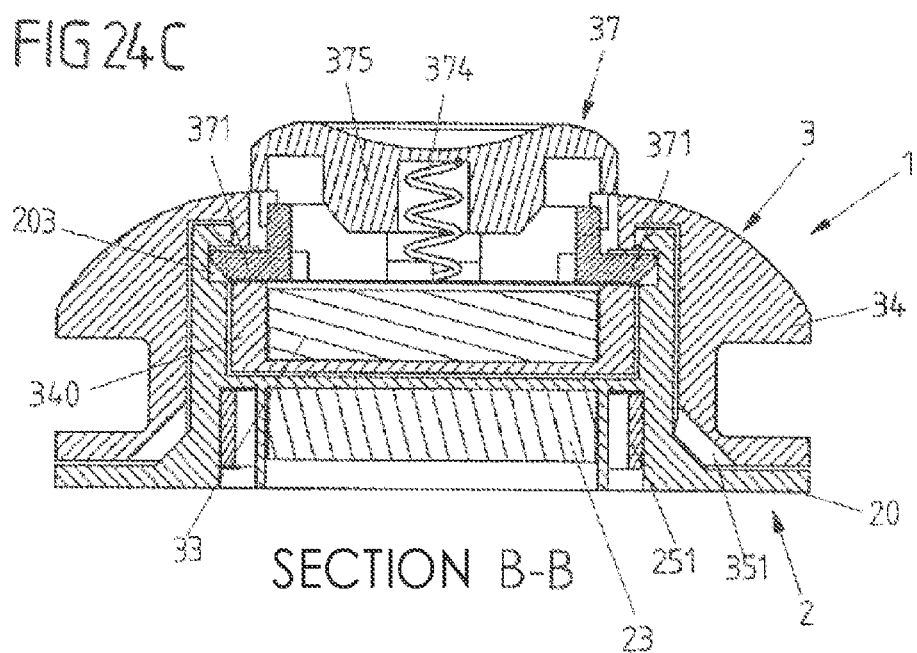
FIG 24C SECTION B-B
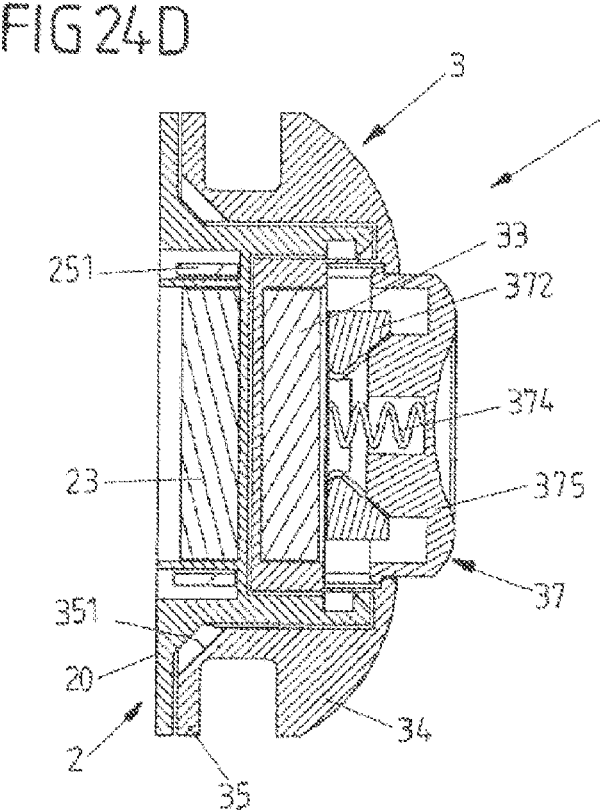
FIG 24D SECTION C-C

SECTION D-D

SECTION E-E

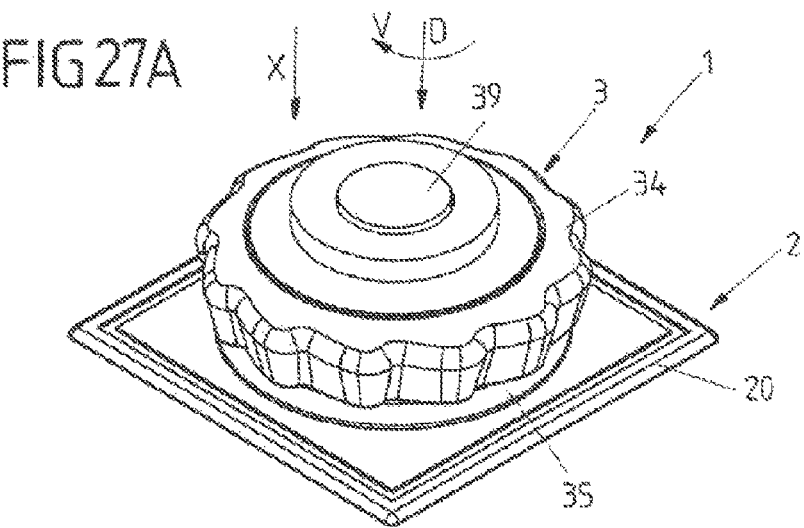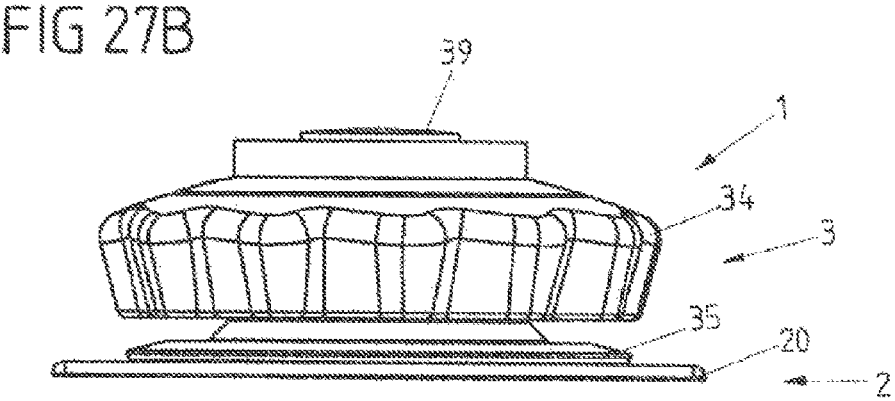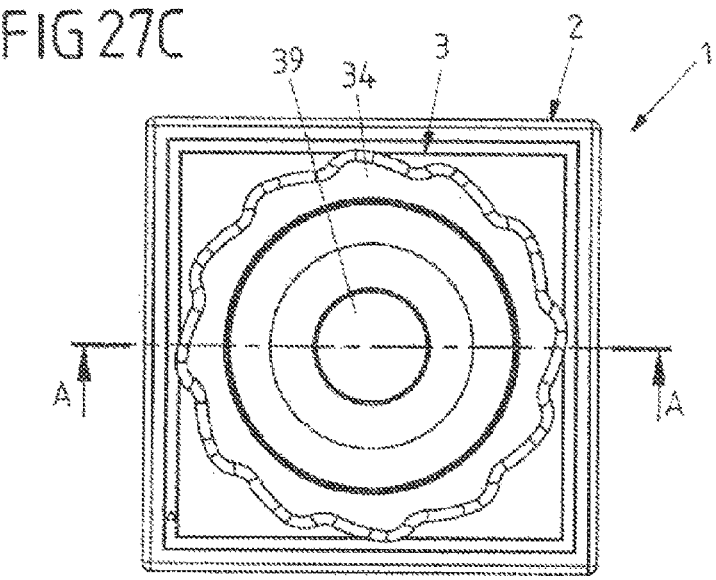

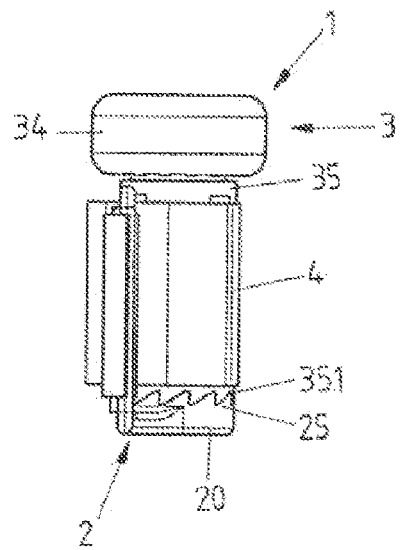
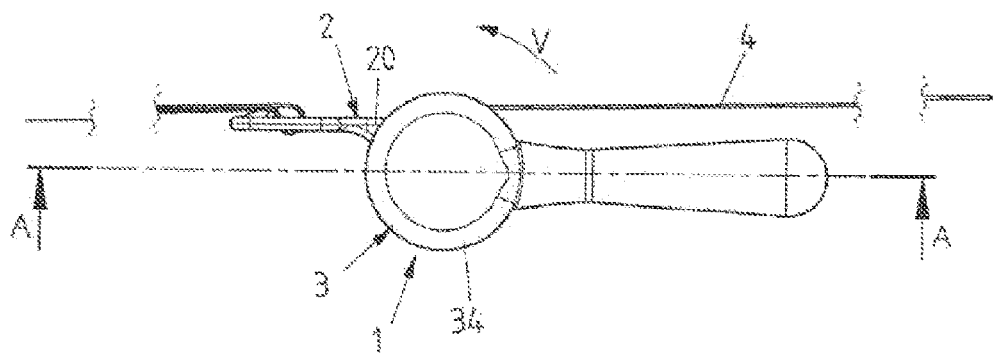
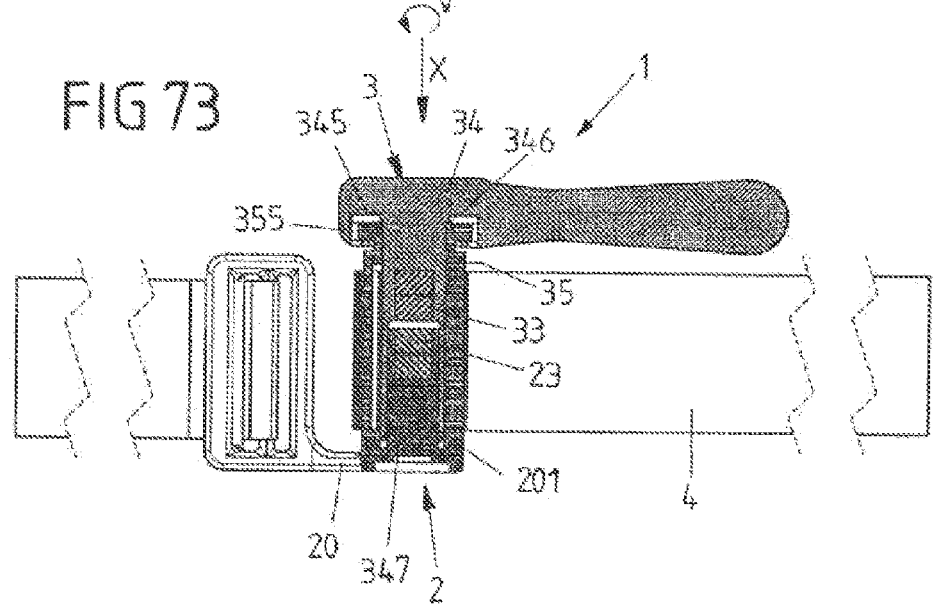

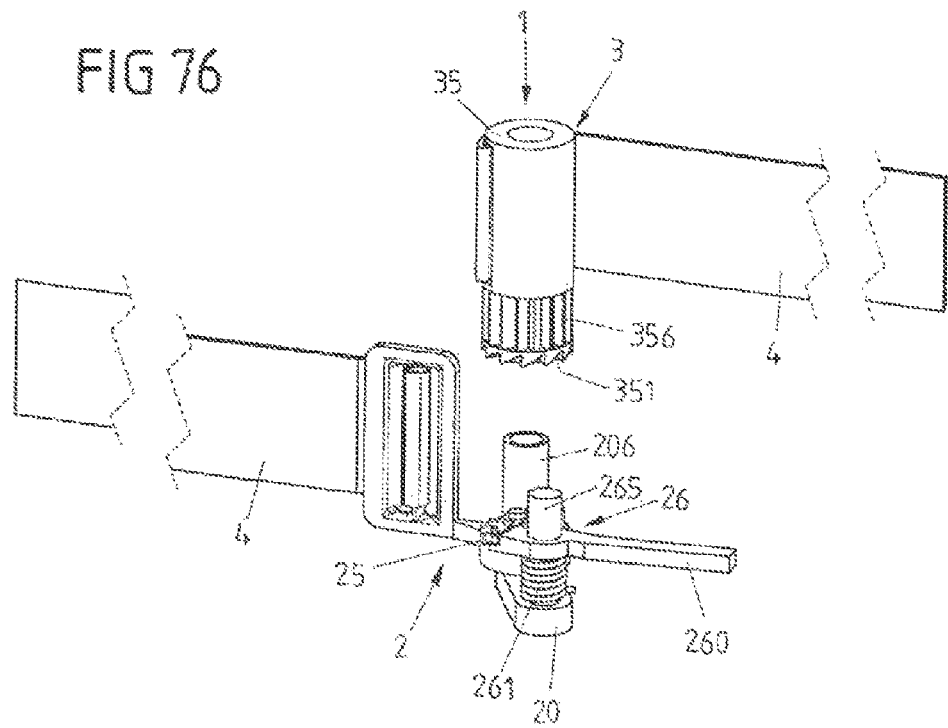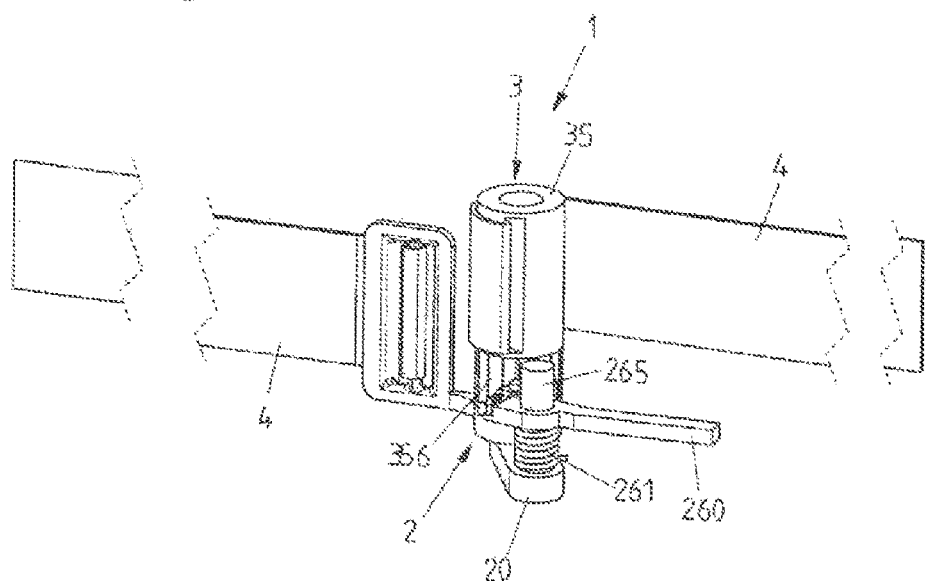

(A)

(A)

CLOSING DEVICE HAVING A WINDING ELEMENT

CROSS-REFERENCE TO RELATED APPLICATIONS

This application is a continuation of U.S. patent application Ser. No. 16/461,136, filed May 15, 2019, which issued as U.S. Pat. No. 11,344,086 on May 31, 2022, which is the United States national phase of International Application No. PCT/EP2018/054968 filed Feb. 28, 2018, and claims priority to German Patent Application Nos. 10 2017 203 263.4 filed Feb. 28, 2017, 10 2017 220 304.8 filed Nov. 14, 2017, and 10 2018 201 019.6 filed Jan. 23, 2018, the disclosures of which are hereby incorporated by reference in their entirety.

BACKGROUND OF THE INVENTION

Field of the Invention

The disclosure relates to a fastener device.

Technical Considerations

A fastener device of said type comprises a first fastener part and a second fastener part which can be mounted on one another along a closing direction, are held against one another in a closed position, and are releasable from one another in order to open the fastener device.

A fastener device of said type serves generally for connecting two parts together. For example, a fastener device of said type may provide a fastener for a container, for example a bag or a rucksack. A fastener device of said type may however also serve for example as a fastener for a shoe, for example a sports shoe. Very generally, the fastener device may serve for connecting any two assemblies with load-bearing action.

It may be desirable here that a fastener device of said type cannot only be used for detachably connecting two parts together but also permits tightening. For example, in the case of a fastener for a rucksack or in the case of a fastener for a shoe, it may be desirable for parts to be able to be firstly mounted on one another but secondly also tightened relative to one another.

A tightening device with a tension element that can be wound up on a winding element is described for example in WO 2015/006616 A1.

SUMMARY OF THE INVENTION

It is an object underlying the proposed solution to provide a fastener device which permits firstly detachable connection of assemblies to one another but secondly also tightening of the assemblies relative to one another.

Said object is achieved by means of a fastener device having features as described herein.

Accordingly, the second fastener part has a winding element on which a tension element can be arranged and which is rotatable relative to the first fastener part in order to wind up the tension element on the winding element in a winding direction.

With the proposed fastener device, a fastener for detachably connecting two parts together and a tightening device are combined with one another. Firstly, the fastener device has two fastener parts which can be mounted on one another along a closing direction and are held against one another in a closed position, such that assemblies assigned to the fastener parts are connected together by means of the fastener parts and by virtue of said fastener parts being held against one another, and the assemblies can also be released from one another again by virtue of the fastener parts being separated from one another. Secondly, the second fastener part has a winding element on which a tension element can be arranged. The winding element may have the form of a cylindrical roller and may bear a winding channel in which the tension element can be received. By rotating the winding element, the tension element can thus be wound up and thus tightened.

Whereas the first fastener part may be arranged on a first assembly, the second fastener part may be connected to a second assembly via the tension element, wherein, by virtue of the tension element being wound up on the winding element, the first assembly and the second assembly can be tightened relative to one another.

The tension element may be a flexible element which is suitable (exclusively) for transmitting tensile forces. The tension element may be a cable, a strap, a band, a belt, a chain or a (an electrically conductive) cable.

The tension element may be secured with two ends on the winding element, such that, by rotation of the winding element, the tension element can be wound with its two ends onto the winding element. It is however also conceivable and possible for only one end of the tension element to be secured on the winding element, in order for only said one end to be wound up by rotation of the winding element. It is furthermore also conceivable and possible for an inner portion of the tension element to be arranged on the winding element in order for the tension element to be wound up by rotation of the winding element. It is also conceivable for multiple different tension elements to be arranged on the winding element and to be able to be wound up by means of the winding element.

The winding element is rotatable relative to the first fastener part in a winding direction in order to wind up the tension element. Here, the winding direction is preferably directed around the closing direction, such that the winding element is rotatable relative to the first fastener part around the closing direction. The fastener parts can thus be mounted on one another along the closing direction, and the winding element can be rotated about the closing direction, in order to brace the assemblies assigned to the fastener parts with respect to one another.

In one refinement, the winding element, in the closed position, may be rotatable relative to the first fastener part. Here, the winding element, in the closed position, is preferably rotatable relative to the first fastener part in the winding direction but not counter to the winding direction. This makes it possible for the tension element to be wound up onto the winding element when the fastener parts have been mounted on one another. After the tension element has been wound onto the winding element, the winding element remains in its assumed position. A backward movement counter to the winding direction for unwinding of the tension element is locked.

In another refinement, it may be provided, by contrast, that, when the fastener parts have been mounted on one another, a rotation of the winding element relative to the first fastener part is no longer possible. In this case, therefore, a rotational movement both in the winding direction and counter to the winding direction is locked when the fastener parts have been mounted on one another.

In one embodiment, the winding element has a toothing means which, in the closed position, engages with a toothing means of the first fastener part. Such a toothing means may be formed by a sawtooth-like toothing running in encircling fashion along the winding direction. Such a toothing means may however also be formed by individual toothing elements which do not form a continuous toothing.

By such toothing means, it is possible in particular to provide a type of freewheel which permits a rotation of the winding element relative to the first fastener part in the winding direction when the fastener parts have been mounted on one another and are thus situated in the closed position, but locks a movement counter to the winding direction. In the event of rotation of the winding element relative to the first fastener part, the toothing means of the winding element slides over the toothing means of the first fastener part, such that a detaining movement of the winding element relative to the first fastener part in the winding direction is possible. In the event of load being exerted counter to the winding direction, toothing elements of the toothing means however engage with one another such that a movement is locked and the winding element is thus held in its presently assumed position.

The toothing means may be in engagement with one another in an axial direction. In the event of a rotation of the winding element in the winding direction relative to the first fastener part, the toothing means slide over one another, for example by virtue of sawtooth-like toothing elements sliding on one another. If the first fastener part and the second fastener part are mounted so as to be rotatable relative to one another and are guided axially on one another, this may be associated with a (small) axial movement of the first fastener part relative to the second fastener part.

Provision may alternatively be made for at least one of the toothing means to have at least one toothing element which, in the event of rotation of the winding element in the winding direction, can be forced aside transversely with respect to the winding direction. In this case, it is thus the case that no axial movement occurs between the fastener parts, but rather the toothing elements of one of the toothing means are forced aside if the winding element is rotated in the winding direction relative to the first fastener part. This may be expedient in particular if the first fastener part and the second fastener part are, in the closed position, mechanically detained together and thus cannot be moved axially relative to one another.

In general, the first fastener part and the second fastener part may, in the closed position, be mechanically detained together in order to hold the fastener parts against one another counter to the closing direction. For this purpose, one of the fastener parts may have a detent means with at least one movable detent element which, in a detained position, engages into a detent recess of the other fastener part and thus holds the fastener parts against one another counter to the closing direction. By the detent means, a mechanical detent connection is thus produced between the fastener parts when the fastener parts have been mounted on one another. By the detent means, the fastener parts are held on one another counter to a load acting oppositely to the closing direction, such that a removal of the fastener parts from one another is not possible without releasing the detent connection.

The detent means preferably moves automatically into the detained position during the mounting of the fastener parts on one another. During the mounting of the fastener parts on one another, the fastener parts are thus automatically detained together, such that the hold of the fastener parts against one another in the closed position is safeguarded. Here, the winding element may possibly be rotatable relative to the first fastener part in the winding direction despite the detent connection, such that the tension element can be wound up onto the winding element when the fastener parts have been mounted on one another.

The detent means may have one or more detent elements. These may be spring-preloaded in the direction of their detained position, such that the detent elements preferably automatically engage with the associated detent recess of the other fastener part when the fastener parts are mounted on one another.

In order to be able to release the detent connection between the fastener parts and separate the fastener parts from one another in order to open the fastener device, the detent means preferably has an operating element which can be actuated in order to disengage the at least one detent element from the detent recess. The operating element may be actuated by means of a pressing action, and may have a run-on element which is designed to, when the operating element is actuated, abut against a run-on element on a preload element, which preloads the at least one detent element in the direction of the detained position, in order to thereby adjust the at least one detent element. The preload element may be formed by a spring ring on which the detent elements are formed at one side and run-on elements are formed at the other side. By virtue of the run-on element of the operating element running onto the run-on elements of the preload element, the ring-shaped preload element is deformed, such that the detent elements are moved and disengaged from the detent recess of the other fastener part.

The winding element may be formed in one piece with an engagement element of the second fastener part, such that the second fastener part with its winding element can be moved as a whole. By rotation of the second fastener part with the winding element arranged thereon, it is thus possible for the tension element to be wound up onto the winding element in order to suitably tighten the tension element. In this case, the fastener parts may be mounted rotatably on one another by virtue of a cylinder collar of one of the fastener parts engaging into the other of the fastener parts and thereby providing a mounting arrangement.

Here, the cylinder collar may be guided axially on the other fastener part, such that the fastener parts can be adjusted axially relative to one another and can be mounted on one another axially along the closing direction.

In one embodiment, the second fastener part has a housing element which, in the closed position, is arranged on the first fastener part and on which the winding element is rotatably mounted. In this case, the housing element may be provided for being mounted rotationally conjointly on the first fastener part and may be held fixedly on the first fastener part in the closed position of the fastener device. The winding element is rotatable relative to the housing element, such that, by rotation of the winding element, the tension element can be wound up in the winding directional to the winding element and thus tightened.

In one embodiment, the second fastener part has a locking assembly which, in a locked state, locks the winding element relative to the housing element such that the winding element is rotatable relative to the housing element in the winding direction but not counter to the winding direction.

The locking assembly thus serves for permitting a rotation of the winding element relative to the housing element in the winding direction but locking a backward rotation of the winding element counter to the winding direction. By means of the locking assembly, it is thus possible for the winding element to be rotated in the manner of a freewheel in the winding direction in order to wind up the tension element, wherein, after rotation, the winding element remains in its assumed position and tensile forces acting on the tension element can thus be accommodated via the locking assembly.

The locking assembly can preferably be unlocked from the locked state. This makes it possible for the winding element to be released such that the winding element can be rotated relative to the housing element also counter to the winding direction in order to unwind the tension element from the winding element. By unlocking the locking assembly, the tension element can thus be relaxed by virtue of the tension element being unwound from the winding element.

In one embodiment, provision may be made for the locking assembly to be automatically unlocked during the opening of the fastener device. If the fastener parts are separated from one another and, for this purpose, the housing element of the second fastener part is removed from the first fastener part, the locking assembly automatically passes into its unlocked state, such that the winding element is released, and thus the tension element can be unwound from the winding element.

In one embodiment, the locking assembly has an actuating element, which may be designed as a handgrip and which is arranged rotatably on the housing element. By means of the actuating element, the winding element can be rotated, wherein, for this purpose, the actuating element is operatively connected to the winding element or operatively disconnected from the winding element in a manner dependent on the state of the locking assembly.

The actuating element and the housing element may be operatively connected to one another by a freewheel means. By the freewheel means, a rotation of the actuating element relative to the housing element is possible in the winding direction, but a rotation counter to the winding direction is locked. If the actuating element is operatively connected to the winding element, it is thus possible by means of the actuating element for the winding element to be rotated in the winding direction but not counter to the winding direction.

In one embodiment, the freewheel means has a toothing on the housing element or the actuating element and has at least one adjustable locking element, for example in the form of a pawl, on the respective other element. The toothing may be formed as an internal toothing on a cylinder collar of the housing element, wherein, in this case, one or more movable (for example pivotable) locking elements may be arranged on the actuating element. In the event of a rotation of the actuating element in the winding direction, the locking elements slide over the toothing, such that a rotation of the actuating element in the winding direction is possible, but an opposite rotation counter to the winding direction is locked owing to the engagement of the locking elements into the toothing, and the actuating element thus cannot be rotated relative to the housing element counter to the winding direction.

It is conceivable and possible here for the actuating element to be able to be unlocked for example by means of an axial adjustment relative to the housing element by virtue of the locking elements being disengaged from the toothing.

In order to produce the operative connection between the actuating element and the winding element, the actuating element may have a first toothing means, whereas the winding element bears a second toothing means. The toothing means may each be of sawtooth-like form, wherein the engagement is such that, in the event of a rotation of the actuating element in the winding direction, the winding element is driven along and is thus likewise rotated relative to the housing element in the winding direction. In the event of the winding element being loaded by tensile forces, introduced via the tension element, which lead to a torque load counter to the winding direction, the winding element is, if the toothing means are in engagement with one another, held in position relative to the housing element by means of the actuating element, such that the tension element cannot be unwound from the winding element.

In order to release the winding element in order to unwind the tension element, the actuating element may be axially adjustable relative to the housing element, such that the toothing means on the actuating element, on the one hand, and on the winding element, on the other hand, disengage, and the winding element is thus no longer held in position by means of the actuating element. The winding element can thus be rotated relative to the howing element counter to the winding direction, and the tension element can thus be unwound from the winding element.

When the fastener parts have been mounted on one another, the housing element is held on the first fastener part. Here, the housing element may, in the closed position, be mechanically fixedly connected to the first fastener part, by virtue of the housing element being detained with the first fastener part.

In one embodiment, the first fastener part may have at least one first undercut element, whereas the housing element of the second fastener part comprises at least one second undercut element. The undercut elements engage with one another during the mounting of the fastener parts on one another, such that the fastener parts are, in the closed position, held against one another counter to the closing direction.

The undercut elements may be formed rigidly on a main body of the first fastener part and on the housing element of the second fastener part. After the fastener parts have been mounted on one another in the closing direction, the undercut elements can be placed in engagement with one another in an engagement direction transversely with respect to the closing direction, such that the undercut elements engage into one another and produce a connection between the fastener parts, which connection can be subjected to load counter to the closing direction.

In one refinement, the first fastener part has at least two first undercut elements which are arranged, offset with respect to one another transversely with respect to the closing direction, on a main body of the first fastener part. Likewise, the housing element of the second fastener part may have at least two second undercut elements, which are arranged, offset with respect to one another transversely with respect to the closing direction, on the housing element of the second fastener part and which, in the closed position, are assigned to, and engage with, the first undercut elements of the first fastener part. By means of an arrangement of multiple undercut elements on each fastener part, it is possible for a high-strength, mechanically load-bearing connection to be created between the fastener parts in the closed position.

The first undercut elements of the first fastener part may be situated diametrically oppositely with respect to the axis of rotation of the winding element, and the second undercut elements of the housing element of the second fastener part may likewise be situated diametrically oppositely with respect to the axis of rotation of the winding element. Thus, undercut elements are arranged on both sides of the winding element, such that forces which act between the fastener parts in the closed position can be accommodated and dissipated in an effective manner.

The undercut elements may each have an arcuate shape or a V shape. An arcuate shape is to be understood here to mean any curved form which may also in certain portions have portions extending in a straight manner, and which is thus curved only in certain portions. A V shape may be formed by two undercut elements which are arranged at an angle with respect to one another and thus form a V shape.

In one embodiment, one of the fastener parts has a blocking element which serves for safeguarding the engagement between the at least one first undercut element and the at least one second undercut element in the closed position of the fastener parts. Such a blocking element may be arranged on the first fastener part and, in the closed position, imparts a blocking action between the fastener parts such that the engagement between the undercut elements is safeguarded and the undercut elements in particular cannot disengage from one another counter to the engagement direction.

The blocking element may, in a blocking position, face toward a component of the other fastener part, such that, by means thereof, the undercut elements are held in engagement. If the fastener parts are loaded counter to the engagement direction, the blocking element prevents the undercut elements from disengaging from one another, such that, in this way, the hold of the fastener parts against one another is safeguarded.

The blocking element is preferably spring-preloaded in the direction of its blocking position. During the closing of the fastener device, the blocking element thus automatically passes into its blocking position, such that, in the closed position, the fastener parts are safeguarded in terms of their connection to one another.

The blocking element may, for the purposes of opening, be adjustable out of its blocking position. By means of manual action on the blocking element, the blocking of the fastener parts relative to one another may thus be eliminated, such that the fastener parts can be released from one another by separation of the undercut elements.

Provision may alternatively also be made for the component of the other fastener part, toward which the blocking element faces in the blocking position, to be adjusted such that, by means thereof, the blocking action of the blocking element is eliminated. If the blocking element is arranged on the first fastener part, the component may be the actuating element of the second fastener part, which can be adjusted axially relative to the housing element in order to thereby firstly eliminate the operative connection between the actuating element and the winding element and secondly move the actuating element out of its opposite position, with blocking action, in relation to the blocking element.

A fastener device of the type described above may be designed as a purely mechanical fastener device, in the case of which the fastener parts are mounted on one another and are mechanically held against one another in the closed position. By means of such mechanical hold, it is possible here for shear forces in a plane transverse with respect to the closing direction to be accommodated, and additionally possibly also forces counter to the closing direction in the case of a mechanical detent connection between the fastener parts.

In one advantageous embodiment, the fastener device is however of magnetic design. For this purpose, the first fastener part and the second fastener part each have at least one magnet element which, during the mounting of the fastener parts on one another, are situated opposite one another with magnetically attractive action in order to close the fastener device and thus magnetically assist the closing of the fastener device.

Here, a magnet element may be formed by a permanent magnet or else by a magnetic armature, composed for example of a ferromagnetic material. One of the fastener parts may have a permanent magnet which interacts, with magnetically attractive action, with a magnetic armature of the other fastener part. It is however also conceivable for both fastener parts to each have a permanent magnet, or else an arrangement of multiple permanent magnets, which, during the mounting of the fastener parts on one another, are situated with opposite poles opposite one another and thus assist the mounting process by magnetic attraction.

The actuation of the actuating element may be performed manually by rotating the actuating element. Embodiments are however also conceivable and possible in which an electric motor is provided for driving the actuating element. Such an electric motor may be arranged positionally fixedly on an assembly connected to the first fastener part, and may engage by means of a suitable gearing element, for example a drive worm, with a toothing of the actuating element when the fastener device is situated in its closed position. The actuating element can thus be rotated by means of the electric motor.

It is alternatively conceivable and possible for the toothing means of the first fastener part to be driven by electric motor means in order to rotate the winding element by rotation of the toothing means of the first fastener part.

In one embodiment, in each case one or more electrical contact elements may be arranged on the first fastener part and on the second fastener part such that electrical contact is produced between the fastener parts during the closing of the fastener device.

In a further embodiment, the fastener device may have a winder exit element, may be in the form of an eyelet, which may be arranged on the second fastener part and designed as a component which is additional to the winding element and to the actuating element. The winder exit element may be freely rotatable relative to the winding element and/or the actuating element and guides the tension element in relation to the winding element, such that the tension element runs into the winding element in a defined manner. This prevents uncontrolled unwinding of the tension element from the winding element and in particular knotting of the tension element during the unwinding process.

The fastener device described here permits a releasable connection of fastener parts in combination with a tightening facility for a tension element. This makes it possible, for example, for the tension element to be preloaded under tension with the fastener parts separated in order for the fastener device to then be closed and, in the closed position of the fastener device, for the tension element to be wound up and retightened by rotation of the winding element. In the case of a shoe, it is possible in this way for the tension element (in the form of a shoelace) to be manually pretightened by pulling on the tension element with the fastener device separated and then retightened with the fastener device closed.

Furthermore, the separation of the fastener parts makes it possible for the tension element connected to the winding element to be laid around an article in order for one assembly to be fixed to another by means of the fastener device. With the fastener device open, the tension element can be laid around a mast or a frame, for example a bicycle frame, in order for the fastener device to then be closed and the tension element tightened, such that an assembly can be fixed to the mast or to the frame in this way.

A fastener device of the type described here may be used in a wide variety of ways. A fastener device of the type described here may be used on bags or other containers such as rucksacks, boxes or containers, on shoes (in particular sports shoes such as walking shoes, ski boots or the like), on helmets, in particular sports helmets, or on medical aids such as for example medical support splints or the like.

By means of a fastener device of the type described here, it may be possible for straps on sacks or bags to be tightened (so-called compression straps). A strap or a hip strap of a rucksack or school satchel can be closed and tightened by means of such a fastener device. Also, such a fastener device may be used on a cable drum for winding up an electrical cable, for example a headphone or charging cable.

In the case of a helmet, it is possible by means of a fastener device of the type described here for a strap to be tightened or for an article to be secured on the helmet, for example protective goggles (such as ski goggles) or the like.

A fastener device of said type may also serve for the stowage and securing of accessories or bags in or on vehicles (bicycles, passenger motor vehicles, heavy goods vehicles, ships, aircraft etc.), for example as a tightening device on a bicycle luggage carrier.

Specifically, a fastener device of said type may be used on a holder, which can be tightened around a bicycle frame, for the purposes of fixing an assembly, for example a drinking bottle or a container, to the bicycle frame.

Furthermore, a fastener device of said type may be used for tensioning tarpaulins and sheets of any type, for example for tensioning tent tarpaulins or for tensioning a sunblind.

Military applications are also conceivable and possible. Accordingly, a fastener device may be used for the tensioning and stowage of weapons and munitions.

A fastener device of the described type may also be used in a tourniquet ligature system for ligating heavily bleeding wounds on a patient.

BRIEF DESCRIPTION OF THE DRAWINGS

The concept on which the solution is based will be discussed in more detail below on the basis of the embodiments illustrated in the figures, in which:

FIG. 2A shows an exploded view of the fastener device;

FIG. 3A shows the fastener device prior to the mounting of the fastener parts on one another;

FIG. 3B shows the fastener device in a side view;

FIG. 3C shows a sectional view along the line A-A as per FIG. 3B;

FIG. 3D shows a sectional view along the line B-B as per FIG. 3B;

FIG. 4C shows a sectional view along the line A-A as per FIG. 4B;

FIG. 4D shows a sectional view along the line B-B as per FIG. 4B;

FIG. 5C shows a sectional view along the line A-A as per FIG. 5B;

FIG. 5D shows a sectional view along the line B-B as per FIG. 5B;

FIG. 6C shows a sectional view along the line A-A as per FIG. 6B;

FIG. 6D shows a sectional view along the line B-B as per FIG. 6B;

FIG. 7C shows a sectional view along the line A-A as per FIG. 7B;

FIG. 7D shows a sectional view along the line B-B as per FIG. 7B;

FIG. 8C shows a sectional view along the line A-A as per FIG. 8B;

FIG. 8D shows a sectional view along the line B-B as per FIG. 8B;

FIG. 9A shows a view of the fastener device during the opening process;

FIG. 9B shows a side view of the arrangement as per FIG. 9A;

FIG. 9C shows a sectional view along the line A-A as per FIG. 9B;

FIG. 9D shows a sectional view along the line B-B as per FIG. 9B;

FIG. 10A shows a view of the fastener device during the further opening process;

FIG. 10B shows a side view of the arrangement as per FIG. 10A;

FIG. 10C shows a sectional view along the line A-A as per FIG. 10B;

FIG. 10D shows a sectional view along the line B-B as per FIG. 10B;

FIG. 11A shows a view of another embodiment of a fastener device;

FIG. 11B shows another view of the fastener device;

FIG. 12A shows a plan view of the fastener device;

FIG. 12B shows a side view of the fastener device in the case of fastener parts separated from one another;

FIG. 13B shows another exploded view of the fastener device;

FIG. 15C shows a sectional view along the line A-A as per FIG. 15B;

FIG. 15D shows a partially sectional view of the fastener device;

FIG. 17A shows a view of the fastener device in the case of fastener parts separated from one another;

FIG. 17B shows a side view of the arrangement as per FIG. 17A;

FIG. 17C shows a sectional view along the line A-A as per FIG. 17B;

FIG. 17D shows a partially sectional view of the fastener device;

FIG. 18A shows a view of another embodiment of a fastener device;

FIG. 18B shows another view of the fastener device;

FIG. 19A shows a view of yet another embodiment of a fastener device;

FIG. 19B shows another view of the fastener device;

FIG. 21C shows a sectional view along the line L-L as per FIG. 21B;

FIG. 21D shows a sectional view along the line M-M as per FIG. 21B;

FIG. 22C shows a sectional view along the line F-F as per FIG. 22B;

FIG. 22D shows a sectional view along the line G-G as per FIG. 22B;

FIG. 23C shows a sectional view along the line H-H as per FIG. 23B;

FIG. 23D shows a sectional view along the line I-I as per FIG. 23B;

FIG. 24C shows a sectional view along the line B-B as per FIG. 24B;

FIG. 24D shows a sectional view along the line C-C as per FIG. 24B;

FIG. 27A shows a perspective view of a further embodiment of a fastener device, in a closed position of the fastener device;

FIG. 27B shows a side view of the arrangement as per FIG. 27A;

FIG. 27C shows a plan view of the fastener device;

FIG. 46 shows a view of the embodiment as per FIG. 45, in the case of a closed article of clothing;

FIG. 47 shows a view of another embodiment of an application of the fastener device for closing an article of clothing;

FIG. 48 shows a view of an embodiment of an application of the fastener device for closing and tightening a medical aid;

FIG. 49 shows a view of the embodiment as per FIG. 48, in a closed and tightened state;

FIG. 50 shows a view of another embodiment of an application of the fastener device for closing and tightening a medical aid;

FIG. 51 shows a view of the embodiment as per FIG. 50 in the closed state;

FIG. 52 shows a view of an embodiment of an application of the fastener device for closing and tightening another medical aid;

FIG. 53 shows a view of an embodiment of an application of the fastener device for closing and tightening a belt of a helmet;

FIG. 54 shows a view of the embodiment as per FIG. 53 in the case of a closed belt;

FIG. 55 shows a view of an embodiment of an application of the fastener device for closing and tightening a strap of a helmet;

FIG. 56 shows a view of the embodiment as per FIG. 55, in the case of a closed strap;

FIG. 57 shows a view of an embodiment of an application of the fastener device for hanging a lamp;

Figure 58:
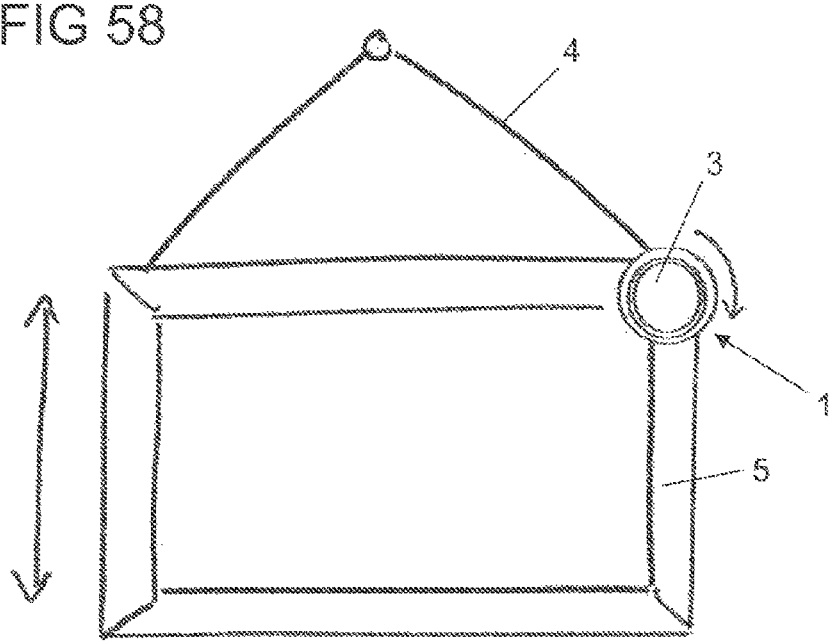
Figure 59:
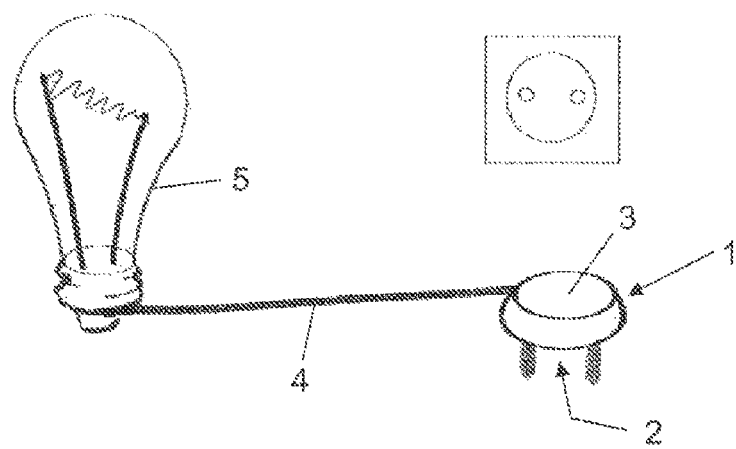
Figure 60:
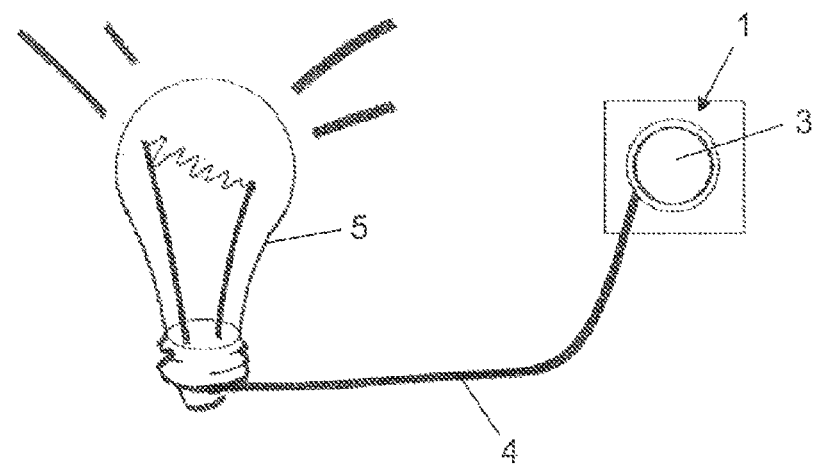
Figure 61:
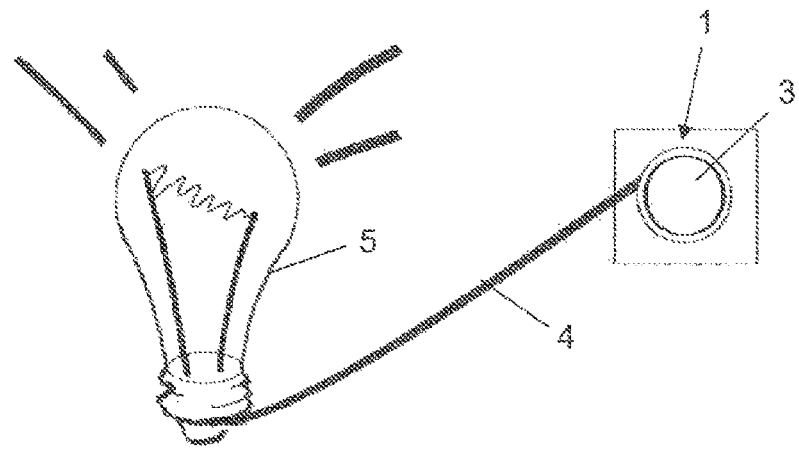
Figure 62:
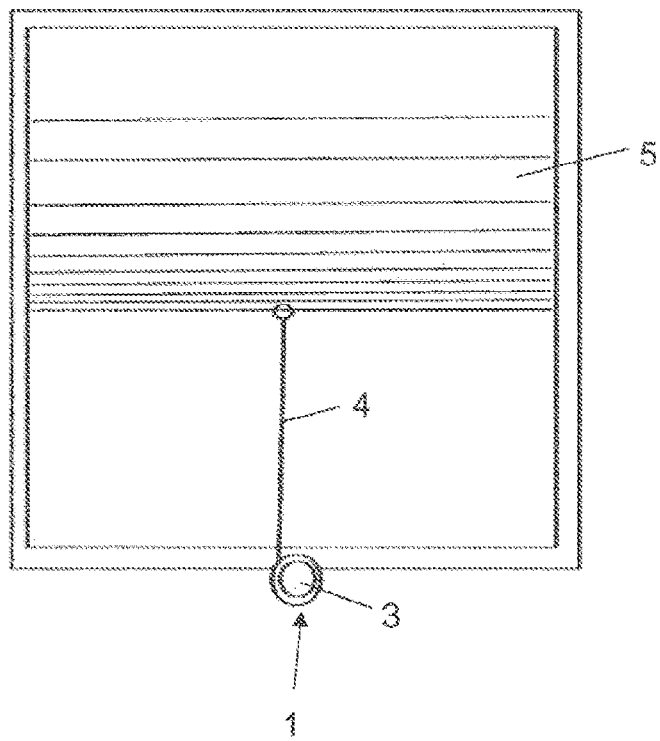
Figure 63:
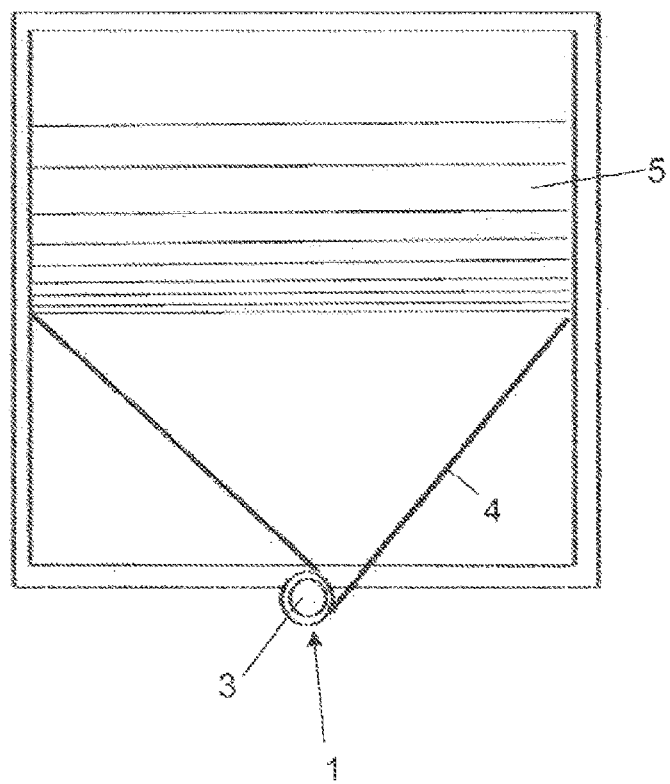
Figure 64:
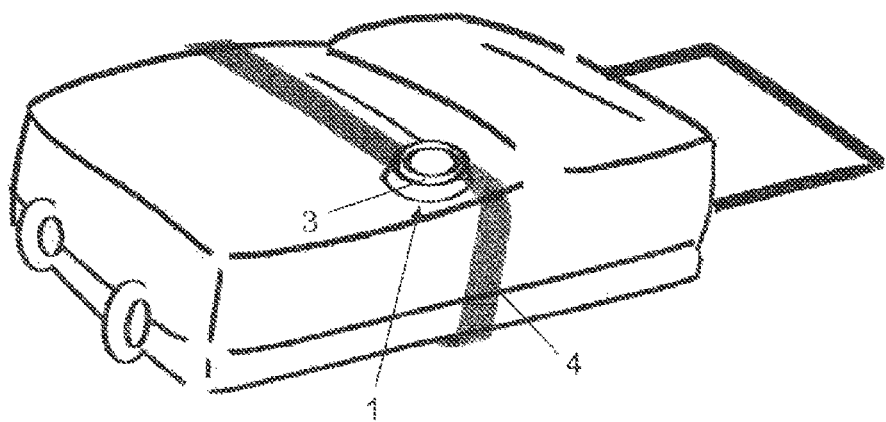
Figure 65:
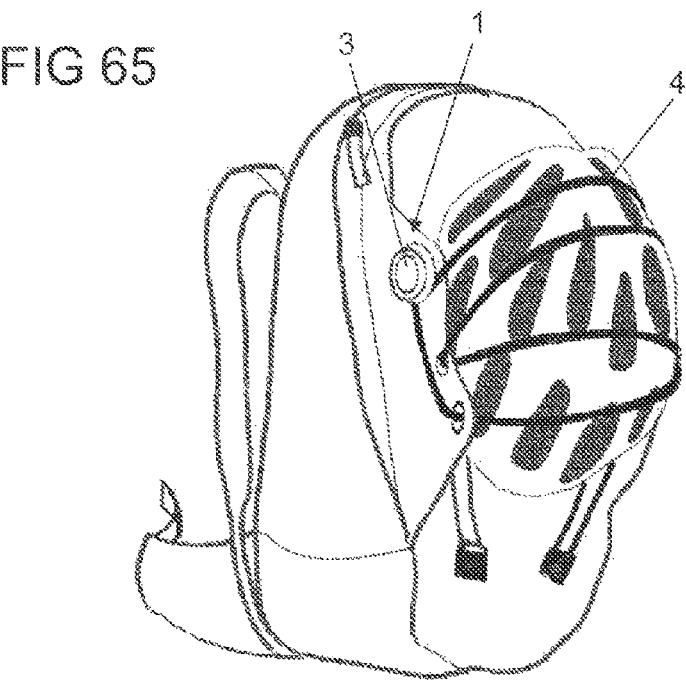
Figure 66:
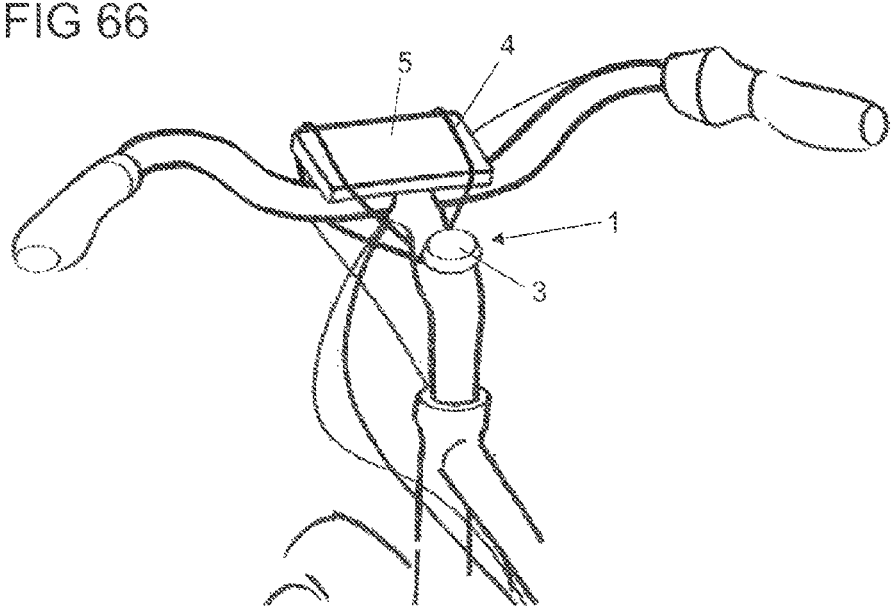
Figure 67:
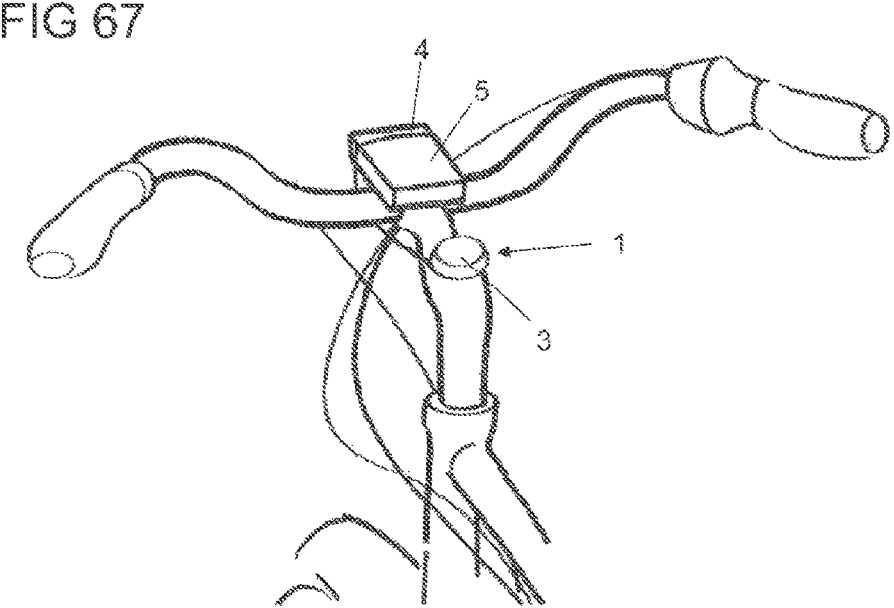
Figure 68:
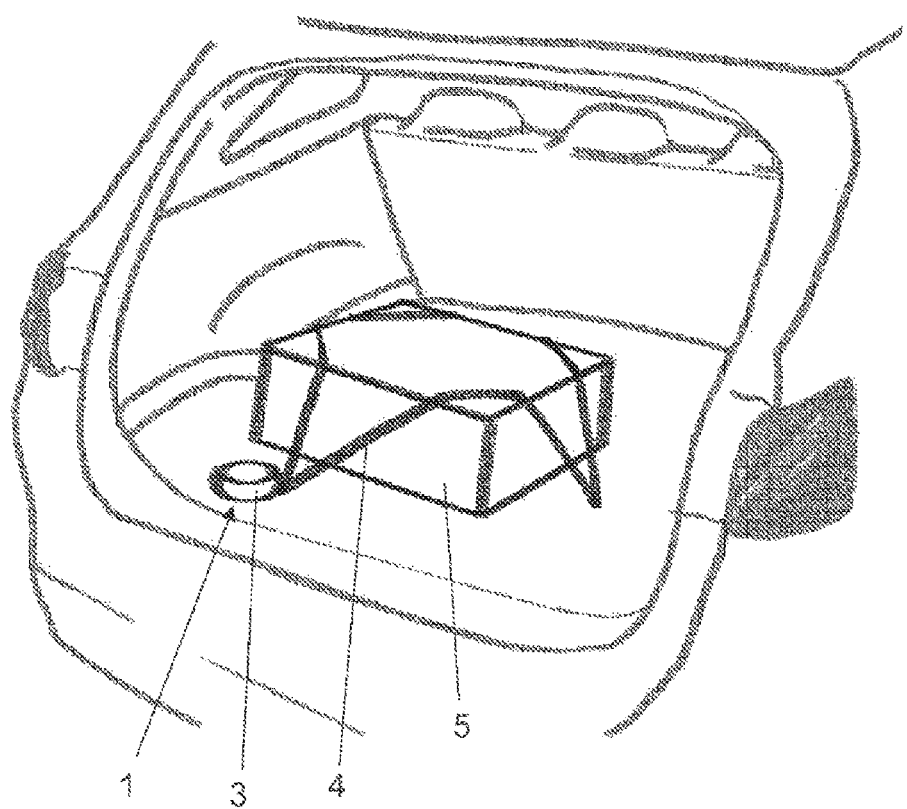
Figure 69:
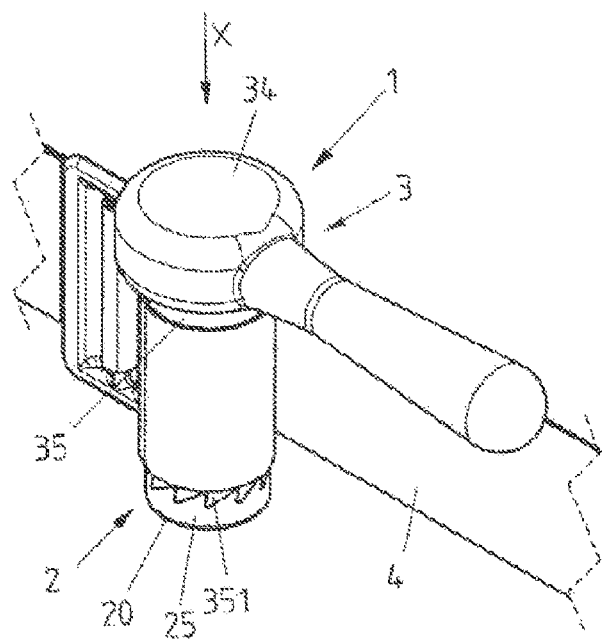
Figure 70:
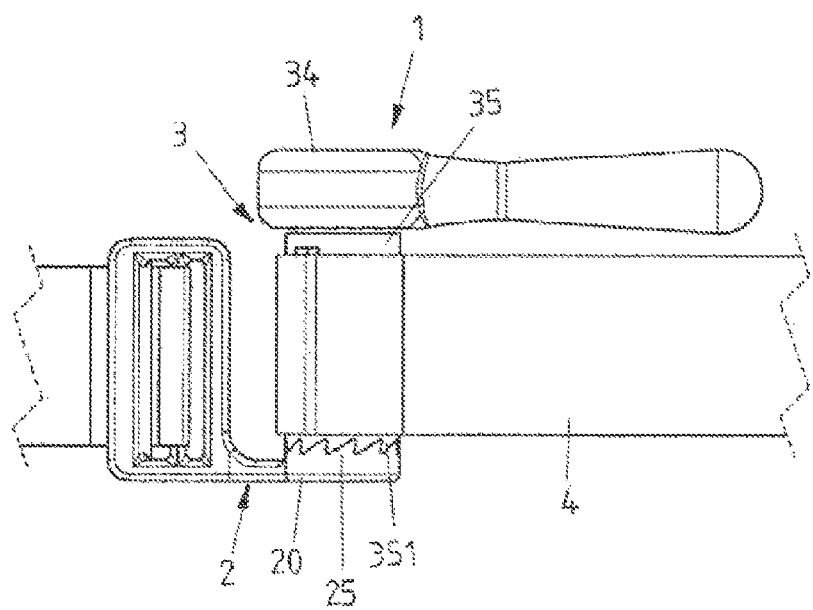
Figure 74A:
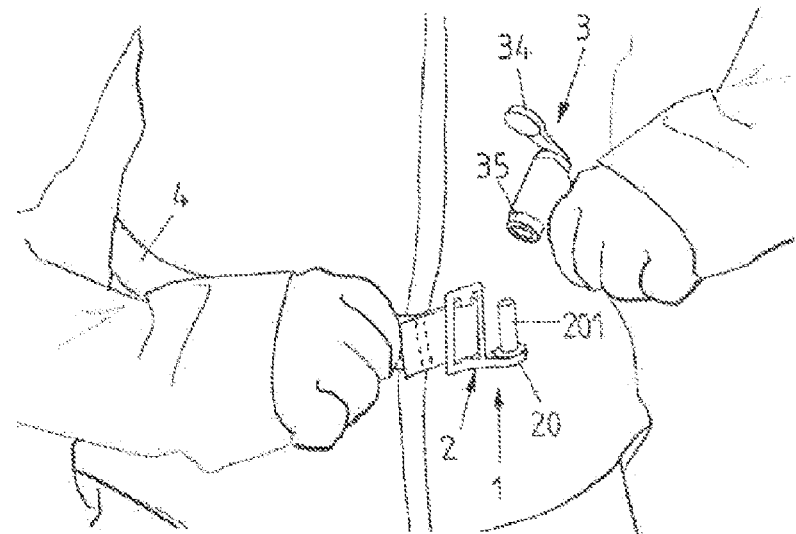
Figure 74B:
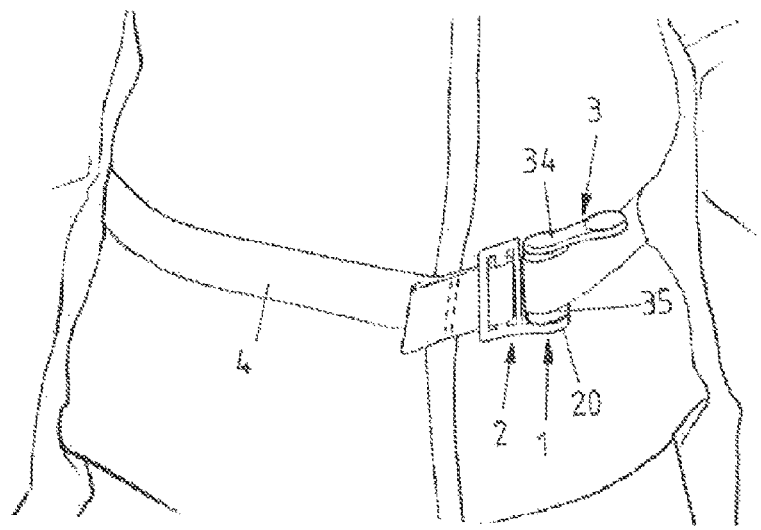
Figure 75:
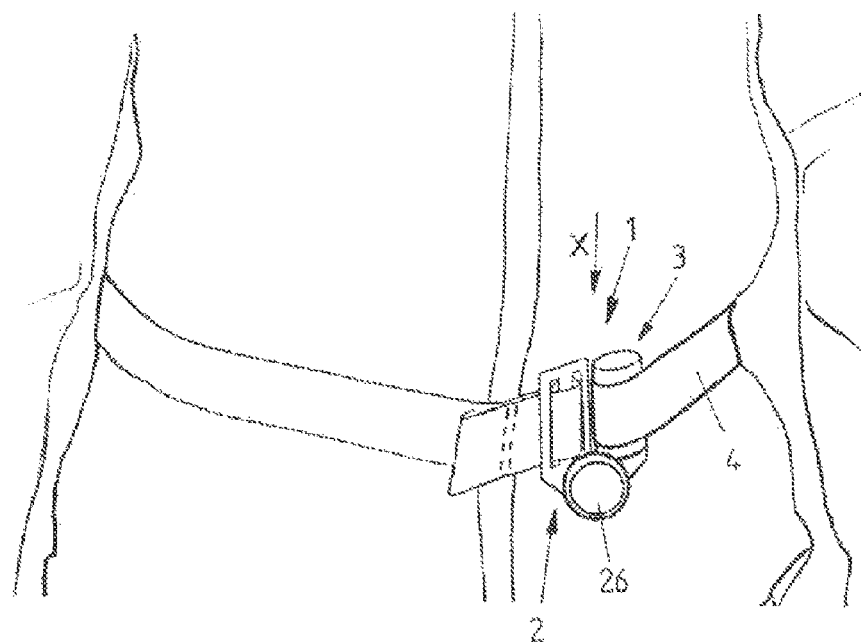
Figure 78A:
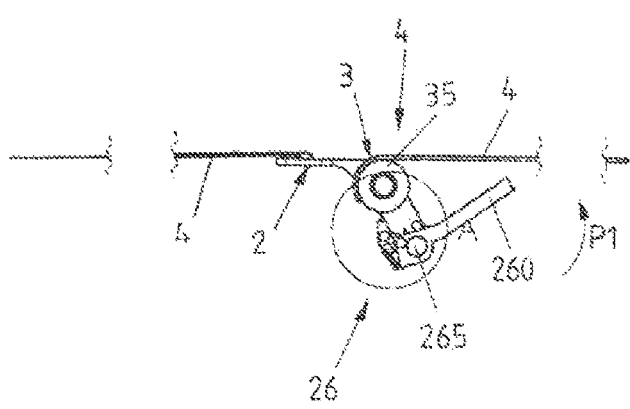
Figure 78B:
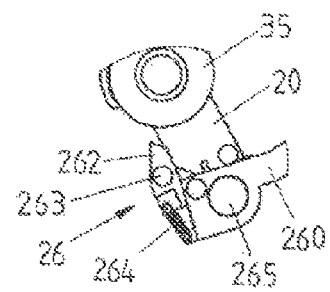
Figure 79A:
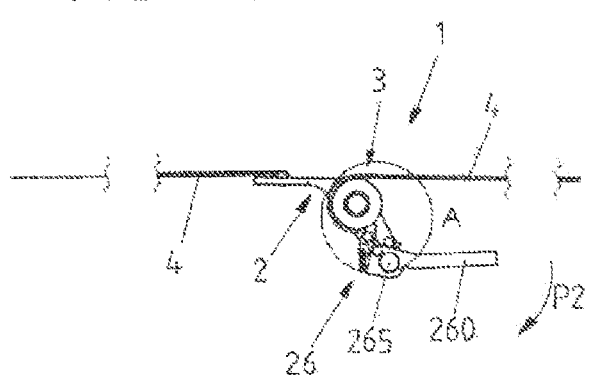
Figure 79B:
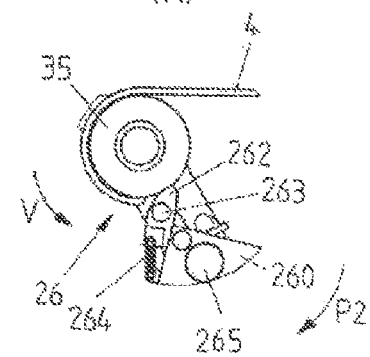

FIG. 58 shows a view of an embodiment of an application of the fastener device for hanging a picture;

FIG. 59 shows a view of an embodiment of an application of the fastener device for connecting a lamp to a plug socket;

FIG. 60 shows a view of the embodiment as per FIG. 59, connected to a plug socket;

FIG. 61 shows a view of the embodiment as per FIG. 60, in the case of a tensioned cable;

FIG. 62 shows a view of an embodiment of an application of the fastener device for tensioning a roller blind;

FIG. 63 shows a view of another embodiment of an application of the fastener device for tensioning a roller blind;

FIG. 64 shows a view of an embodiment of an application of the fastener device for tightening a strap on an article of luggage;

FIG. 65 shows a view of an embodiment of an application of the fastener device for tightening a tension element on a rucksack;

FIG. 66 shows a view of an embodiment of an application of the fastener device for securing an article on a bicycle;

FIG. 67 shows a view of another embodiment of an application of the fastener device for securing an article on a bicycle;

FIG. 68 shows a view of an embodiment of an application of the fastener device for fixing an article in the luggage compartment of a motor vehicle;

FIG. 69 shows a view of a further embodiment of a fastener device with a tension element in the form of a strap;

FIG. 70 shows a frontal view of the fastener device as per FIG. 69;

FIG. 71 shows a side view of the fastener device;

FIG. 72 shows a plan view of the fastener device;

FIG. 73 shows a sectional view along the line A-A as per FIG. 72;

FIG. 74A shows a view of the fastener device for connecting two strap ends together;

FIG. 74B shows a view of the fastener device in the closed state;

FIG. 75 shows a view of another embodiment of a fastener device;

FIG. 76 shows a view of a further embodiment of a fastener device for connecting two strap ends together;

FIG. 77 shows a view of the fastener device in a closed position;

FIG. 78A shows a plan view of the fastener device, with a tightening lever in a position for the mounting of the fastener parts on one another;

FIG. 78B shows an enlarged view in the detail A as per FIG. 78A;

FIG. 79A shows a plan view of the fastener device during the tightening of a tension element; and FIG. 79B shows an enlarged view in the detail A as per FIG. 79A.

DESCRIPTION OF THE INVENTION

FIGS. 1A, 1B to 10A-10D show a first embodiment of a fastener device 1, which has a first fastener part 2 and a second fastener part 3. The fastener parts 2, 3 can be mounted on one another along a closing direction X and are held against one another in a closed position such that, in the closed position, a mechanically fixed connection is created between the fastener parts 2, 3.

Figure 1A:
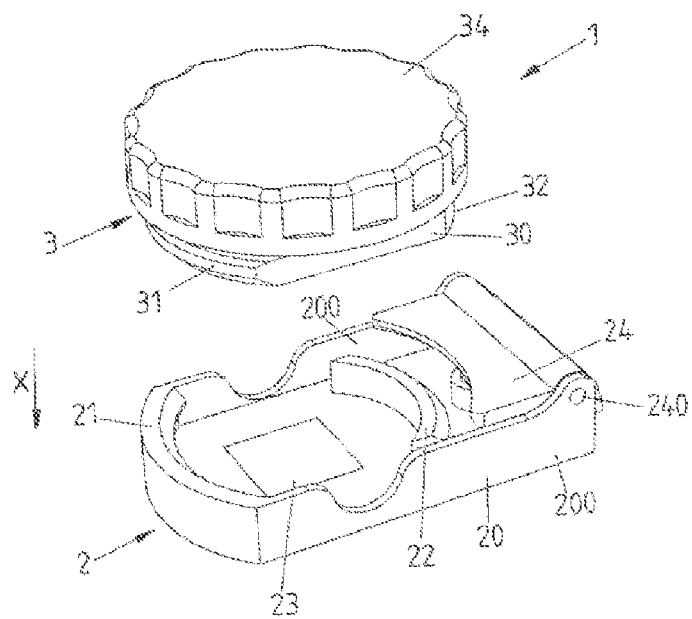
FIG. 1A shows a view of a first embodiment of a fastener device.
Figure 1B:
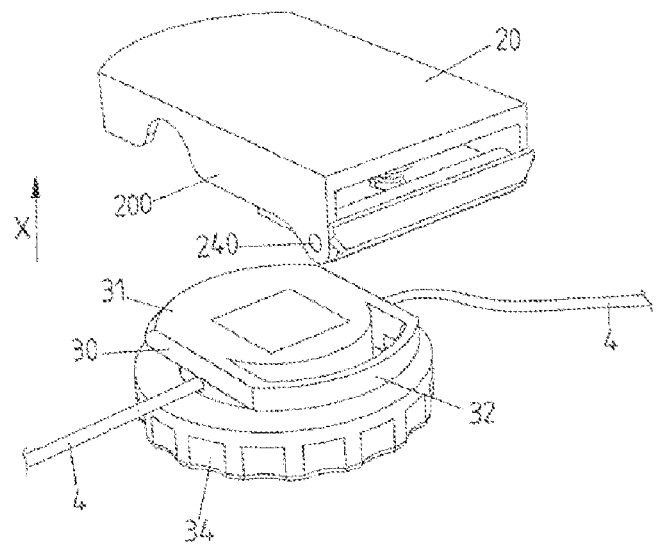
FIG. 1B shows another perspective view of the fastener device.
Figure 2B:
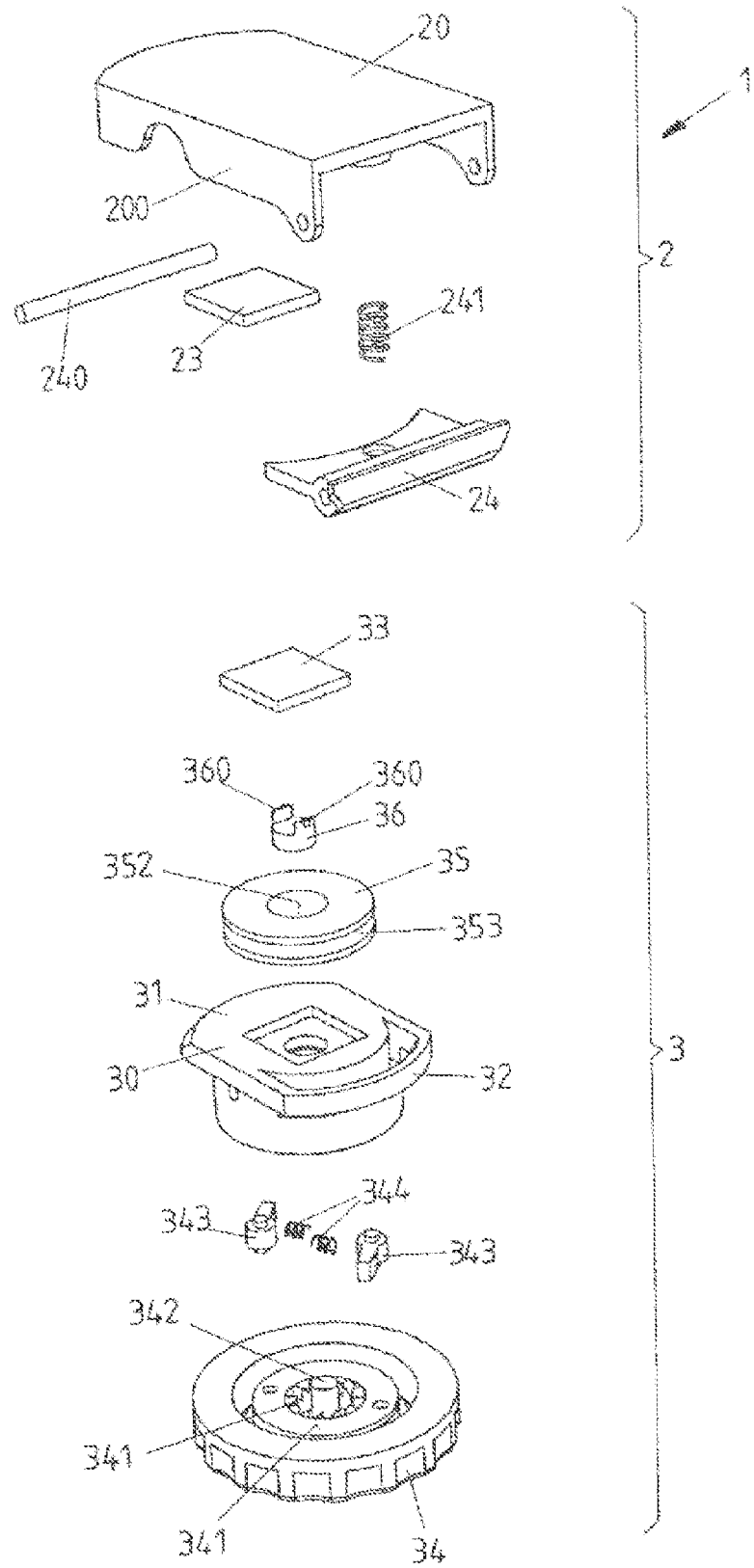
FIG. 2B shows another exploded view of the fastener device.

The first fastener part 2 has, as can be seen in particular from the exploded views as per FIGS. 2A and 2B, a main body 20 on which there are arranged two rigid undercut elements 21, 22 which are each of arcuate design. Also arranged on the main body 20 is a blocking element 24 which, by means of an axle element 240, is mounted pivotably between side walls 200 of the main body 20 and is spring-preloaded by means of a spring element 241 into a blocking position, as will be discussed in more detail below.

The second fastener part 3 has a housing element 30 on which there are arranged two rigid undercut elements 31, 32 which are assigned to the undercut elements 21, 22 of the first fastener part 2 and which, in the closed position, mechanically engage with said undercut elements 21, 22.

On the housing element 30, there is formed a cylinder collar 300 which encloses an interior space 301 in which a winding element 35 is mounted so as to be rotatable about a bearing dome 303. An actuating element 34 in the form of a grip element engages with a body 340 into the interior space 301 and engages with a peg 342 through an opening 304 of the bearing dome 303, and is connected, within the bearing dome 303, to a detent element 36 (see for example the sectional view as per FIG. 3C).

Formed in an encircling manner at the inside on the cylinder collar 300 is a toothing 302 which interacts with locking elements 343 which are preloaded by means of spring elements 344 and mounted movably within the body 340 of the actuating element 34 (see for example the sectional view as per FIG. 3C). As will be discussed in yet more detail further below, the toothing 302 forms, together with the locking elements 343, a freewheel which permits a rotation of the actuating element 34 relative to the housing element 30 in a winding direction V but blocks an opposite rotational movement counter to the winding direction V.

The actuating element 34 has, on an end-side portion of the body 340 facing toward the winding element 35, a toothing 342 which is assigned to a toothing 351 of the winding element 35 and by means of which the actuating element 34 can be placed in operative connection with the winding element 35. If an operative connection exists between the actuating element 34 and the winding element 35, it is possible by means of a rotation of the actuating element 34 for the winding element 35 to be rotated, such that a tension element 4 (see FIG. 1B) can be wound into a channel 353 on a winding body 350 of the winding element 35 in order for the tension element 4 which is led into the interior space 301 via openings 305 to be wound onto the winding body 350.

The first fastener part 2 has a first magnet element 23 secured on the main body 20. The second fastener part 3 has a second magnet element 33 which is arranged on the housing element 30 and which magnetically interacts with the first magnet element 23 of the first fastener part 2. The magnet elements 23, 33 may each be formed by a permanent magnet and situated with opposite poles opposite one another and thus interact with magnetically attractive action during the mounting of the fastener parts 2, 3. Alternatively, one of the magnet elements 23, 33 may be realized by a permanent magnet, whereas the other of the magnet elements 33, 23 is formed by a magnetic armature, composed for example of a ferromagnetic material, and there is thus magnetic attraction between the magnet elements 23, 33.

FIGS. 3A-3D to 10A-10D show the fastener device 1 in different positions.

FIGS. 3A-3D show the fastener device 1 in an opened position with fastener parts 2, 3 separated from one another. As can be seen from the sectional view in FIG. 3C, in the position illustrated, the actuating element 34 is in engagement, by means of its toothing 341, with the associated toothing 351 of the winding element 35, such that there is an operative connection between the actuating element 34 and the winding element 35. In this axial position, the actuating element 34 (which is axially adjustable relative to the housing element 30) is held within the bearing dome 303 of the housing element 30 by detent engagement of detent projections 360 of the detent element 36 into a detent groove 305.

If the actuating element 34 is rotated in a winding direction V relative to the housing element 30, the winding element 35 is jointly rotated owing to the operative connection between the actuating element 34 and the winding element 35, such that a tension element 4 arranged on the winding element 35 is wound up onto the winding body 350 of the winding element 35. A rotation of the actuating element 34 is possible here because, during the rotation of the actuating element 34 in the winding direction V, the detent elements 343 slide over the internal toothing 302 on the cylinder collar 300 of the housing element 30, and therefore a rotation of the actuating element 34 in the winding direction V is not locked.

After a rotation, both the actuating element 34 and also the winding element 35 operatively connected thereto remain in the assumed position. Tensile forces acting on the tension element 4 can, by the winding element 35 and the actuating element 34, be introduced into the housing element 30, and accommodated there, via the locking elements 343 which now have a locking action.

Figure 4A:
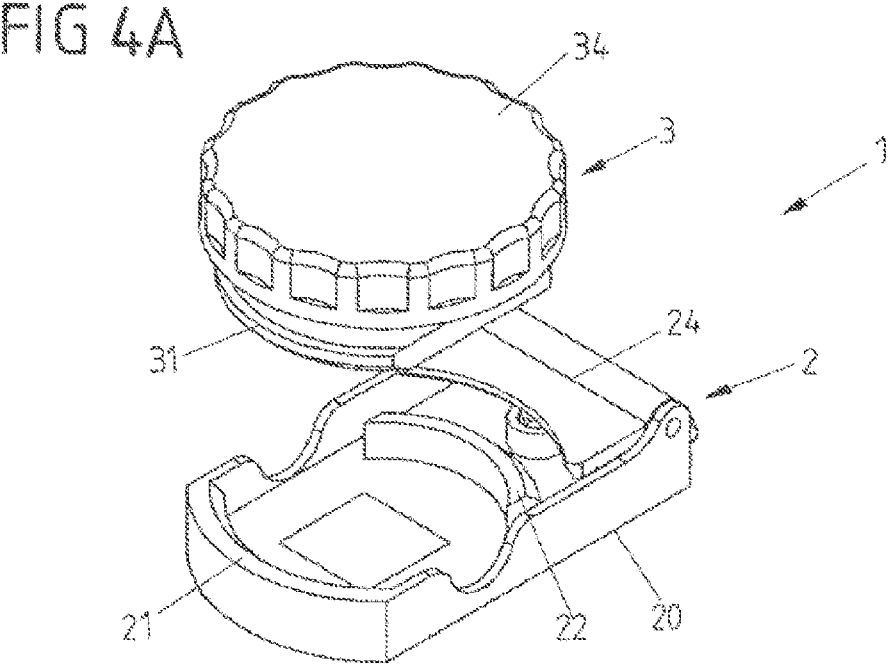
FIG. 4A shows a view of the fastener device prior to mounting of the fastener parts on one another, in the case of an unlocked winding element.
Figure 4B:
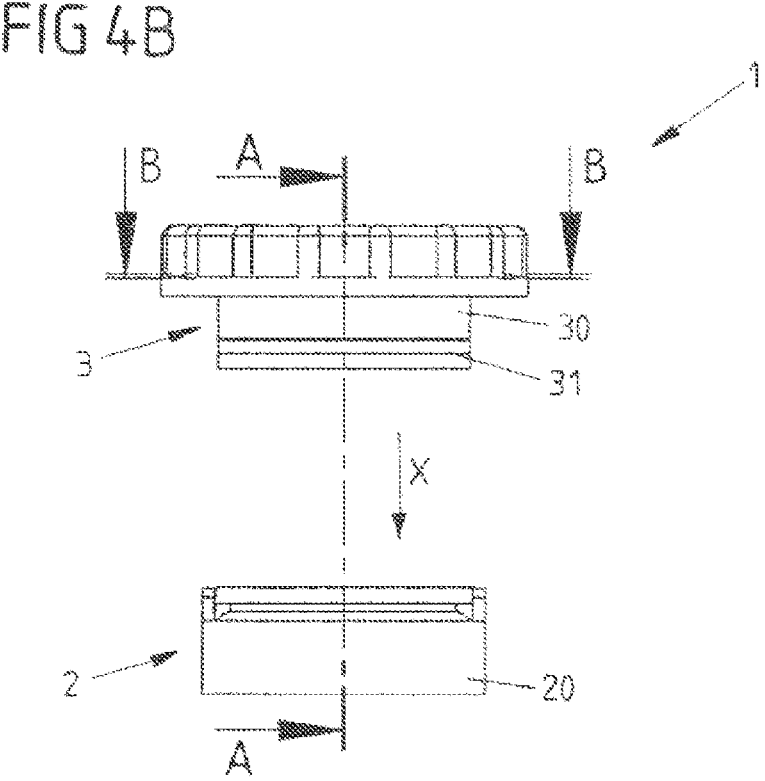
FIG. 4B shows a side view of the fastener device.
Figure 5A:
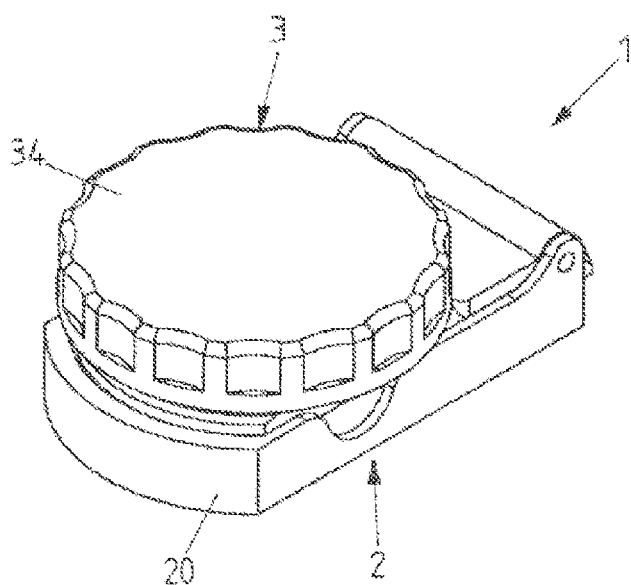
FIG. 5A shows a view of the fastener device during the mounting of the fastener parts on one another.
Figure 5B:
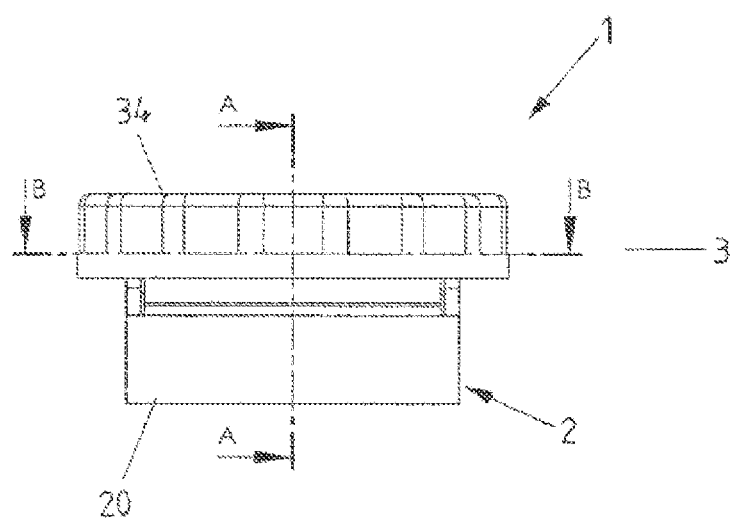
FIG. 5B shows a side view of the arrangement as per FIG. 5A.
Figure 6A:
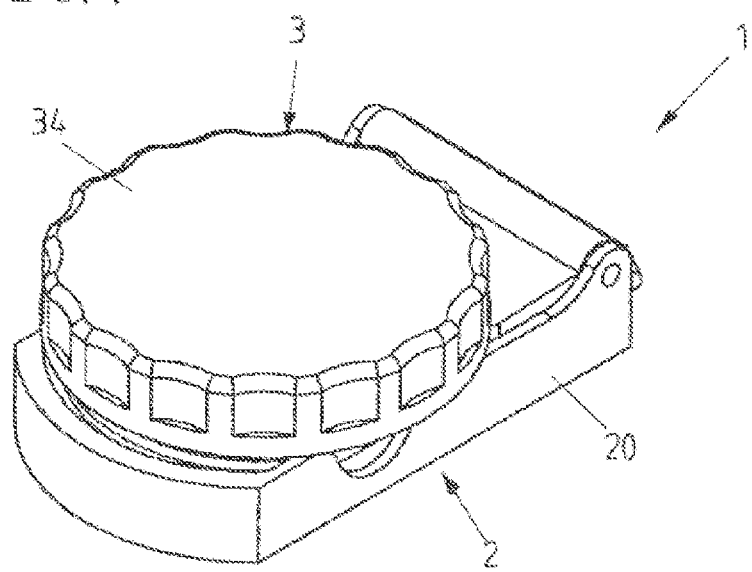
FIG. 6A shows a view of the fastener device during the further mounting of the fastener parts on one another.
Figure 6B:
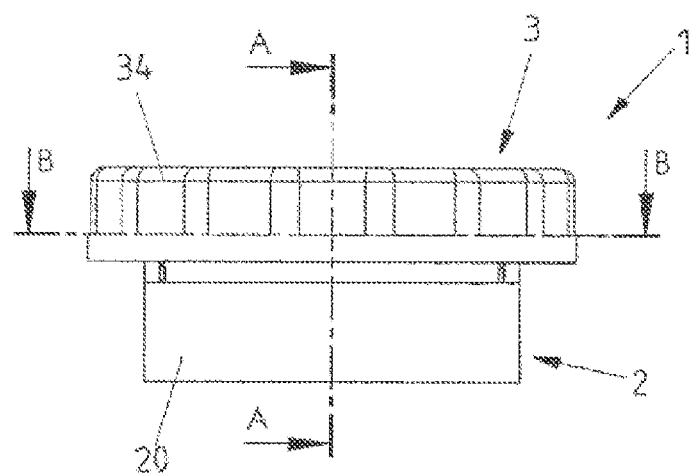
FIG. 6B shows a side view of the arrangement as per FIG. 6A.

In order to release the stress on the tension element 4, the actuating element 34 can be adjusted axially relative to the bearing dome 303 of the housing element 30, as illustrated in FIGS. 4A-4D, whereby—as can be seen from FIG. 4C—the detent elements 360 engage with an upper detent groove 305 within the bearing dome 303 and thus now detain the actuating element 34 in an axially upper position relative to the housing element 30. By means of the axial movement of the actuating element 34, the operative connection between the toothings 341, 351 of the actuating element 34 and of the winding element 35 is eliminated, such that the actuating element 34 and the winding element 35 disengage. The winding element 35 is thus no longer locked and can be moved relative to the housing element 30 counter to the winding direction V, such that the tension element 4 can be unwound from the winding element 35.

By means of the axial movement of the actuating element 34, it is furthermore the case that the locking elements 343 on the body 340 are adjusted axially relative to the internal toothing 302 on the cylinder collar 300 of the housing element 30, such that, in this way, the locking action between the actuating element 34 and the housing element 30 is eliminated. The actuating element 34, too, can thus possibly be freely rotated (even counter to the winding direction V) relative to the housing element 30.

FIGS. 5A-5D and 6A-6D show the fastener device 1 during the mounting of the fastener parts 2, 3 on one another. During the mounting of the fastener parts 2, 3 on one another, the undercut elements 21, 22, 31, 32 on the main body 20 of the first fastener part 2 and on the housing element 30 of the second fastener part 3 run onto one another and are thus offset laterally relative to one another such that the undercut elements 21, 22, 31, 32 can be moved past one another in the closing direction X in order to be placed in engagement with one another.

The mounting of the fastener parts 2, 3 is in this case magnetically assisted by means of the action of the magnet elements 23, 33, such that the mounting can take place substantially automatically.

When the undercut elements 21, 22, 31, 32 have been moved past one another, and when the main body 20 of the first fastener part 2 and the housing element 30 of the second fastener part 3 have come into contact with one another, as illustrated in FIGS. 7A to 7D, the magnet elements 23, 33 are offset with respect to one another. A transverse force thus acts between the magnet elements 23, 33, which transverse force pulls the undercut elements 21, 22, 31, 32 into engagement with one another in an engagement direction E, as illustrated in FIGS. 8A to 8D. The fastener parts 2, 3 thus pass into the closed position illustrated in FIGS. 8A to 8D and, in the closed position, are mechanically connected to one another and held against one another.

Figure 7A:
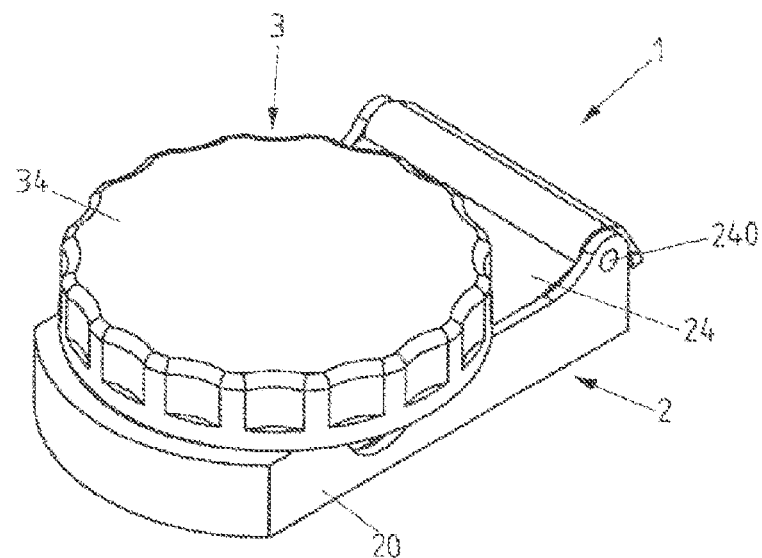
FIG. 7A shows a view of the fastener device during the further mounting of the fastener parts on one another.
Figure 7B:
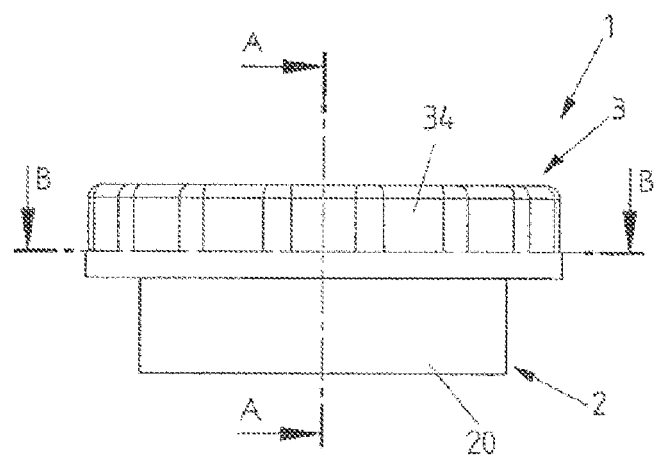
FIG. 7B shows a side view of the arrangement as per FIG. 7A.
Figure 8A:
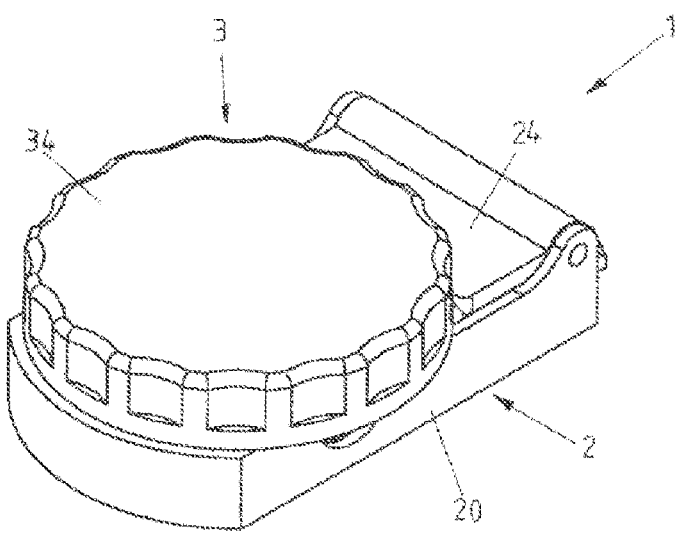
FIG. 8A shows a view of the fastener device in a closed position in the case of fastener parts mounted on one another.
Figure 8B:
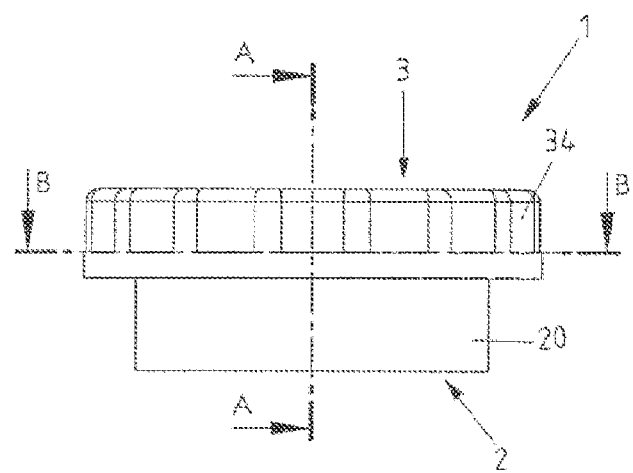
FIG. 8B shows a side view of the arrangement as per FIG. 8A.

As can be seen in particular from FIGS. 7A to 7D, during the mounting of the fastener parts 2, 3 on one another, the actuating element 34 acts on the blocking element 24 and deflects the latter counter to the spring preload of the spring element 241 (see in particular the sectional view in FIG. 7C). When the undercut elements 21, 22, 31, 32 have been placed in engagement with one another, the blocking element 24 is, owing to the spring preload of the spring element 241, moved back into its initial position and passes into a position situated opposite a circumferential edge of the actuating element 34, such that, by means thereof, a movement of the second fastener part 3 relative to the first fastener part 2 in an opening direction Y (counter to the engagement direction E) is locked and, by means thereof, the undercut elements 21, 22, 31, 32 are held in positive locking engagement with one another.

In the closed position, by rotation of the actuating element 34 in the winding direction V, the winding element 35 can be rotated and thus the tension element 4 can be wound up onto the winding element 35. The tension element 4 can thus be tightened, such that a first assembly connected to the first fastener part 2 and a second assembly, which is connected to the second fastener part 3 via the tension element 4, can be fixed to one another under tensile load.

If it is the intention to open the fastener device 1, the actuating element 34 can be adjusted axially relative to the housing element 30 of the second fastener part 3 in a release direction L, as illustrated in FIGS. 9A-9D. As a result, the actuating element 34 disengages from the winding element 35 (the toothings 341, 351 are separated from one another), such that the winding element 35 rotates freely relative to the housing element 30 and can in particular also be moved counter to the winding direction V in order to unwind the tension element 4 from the winding element 35.

By means of axial movement of the actuating element 34 in the release direction L, the actuating element 34 also passes out of its position situated opposite the blocking element 24. The undercut elements 21, 22, 31, 32 can thus be disengaged from one another, such that the fastener parts 2, 3 can be separated from one another, as illustrated in FIGS. 10A-10D.

The release of the fastener parts 2, 3 from one another can take place even with the tension element 4 in a tightened state, that is to say in the presence of an operative connection between the actuating element 34 and the winding element 35. For this purpose, the blocking element 24 can be actuated manually by being pushed downward counter to the spring preload 241, such that the opposite positioning, with blocking action, of the blocking element 24 with respect to the actuating element 34 is eliminated.

FIGS. 11A, 11B to 17A-17B show a second exemplary embodiment of a fastener device 1, in the case of which fastener parts 2, 3 can be mounted on one another along a closing direction X (see for example FIG. 13A) and are held against one another in a closed position.

Figure 13A:
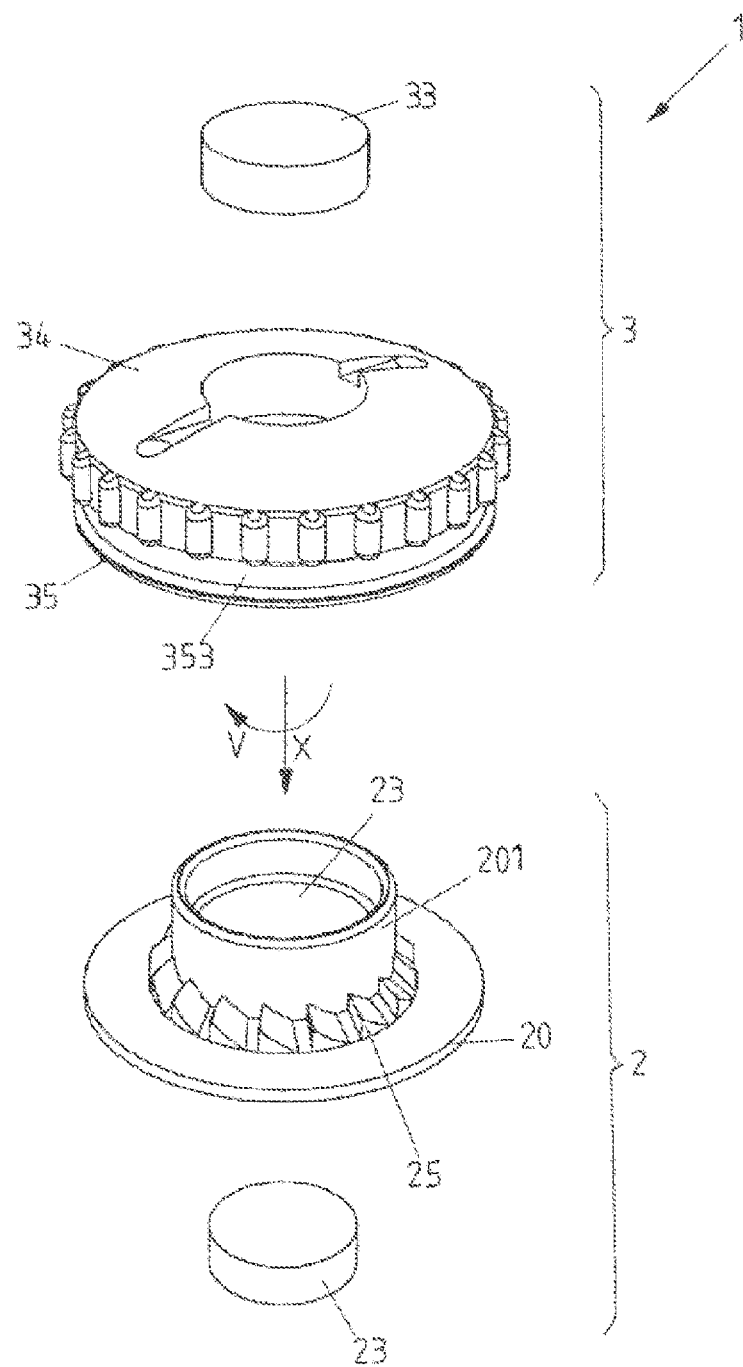
FIG. 13A shows an exploded view of the fastener device.
Figure 14A:
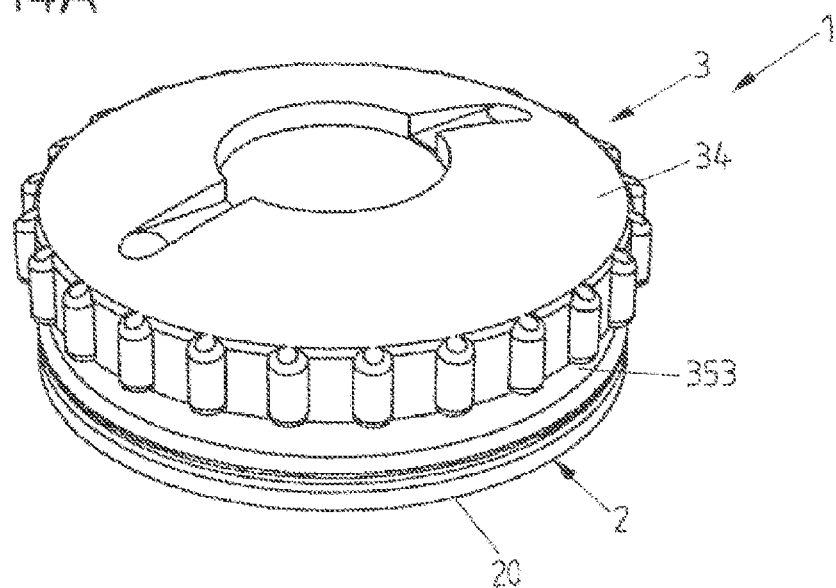
FIG. 14A shows a view of the fastener device in a closed position.
Figure 14B:
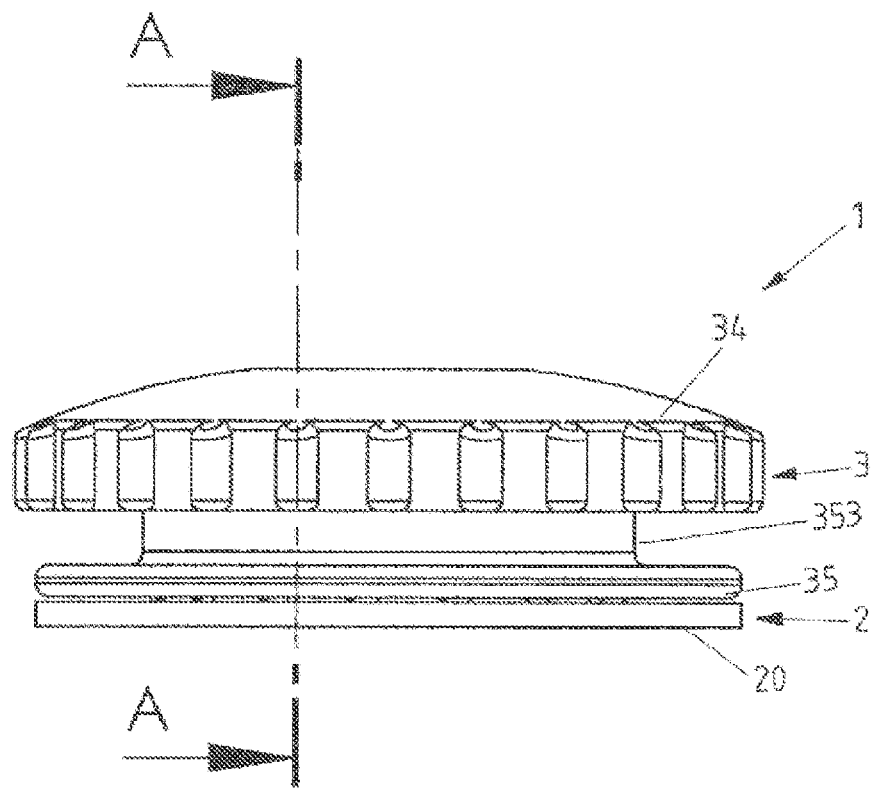
FIG. 14B shows a side view of the arrangement as per FIG. 14A.
Figure 14C:
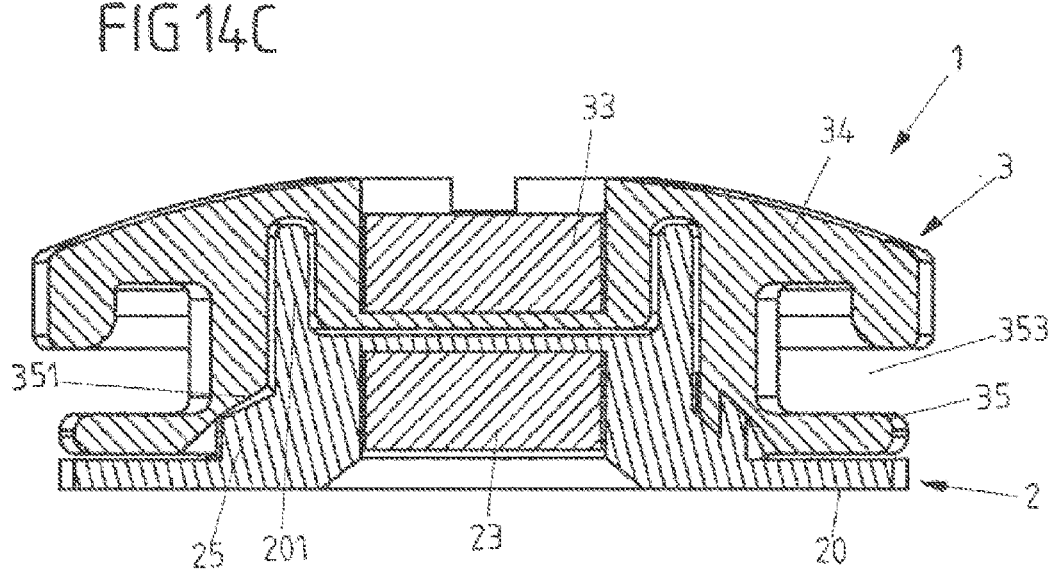
FIG. 14C shows a sectional view along the line A-A as per FIG. 14B.
Figure 14D:
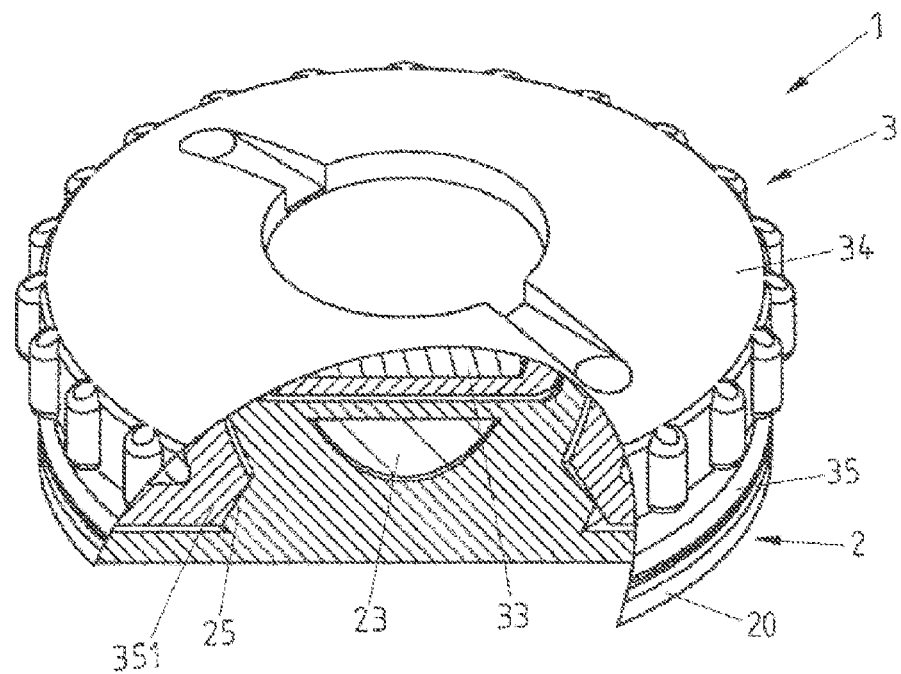
FIG. 14D shows a partially sectional view of the fastener device.
Figure 15A:
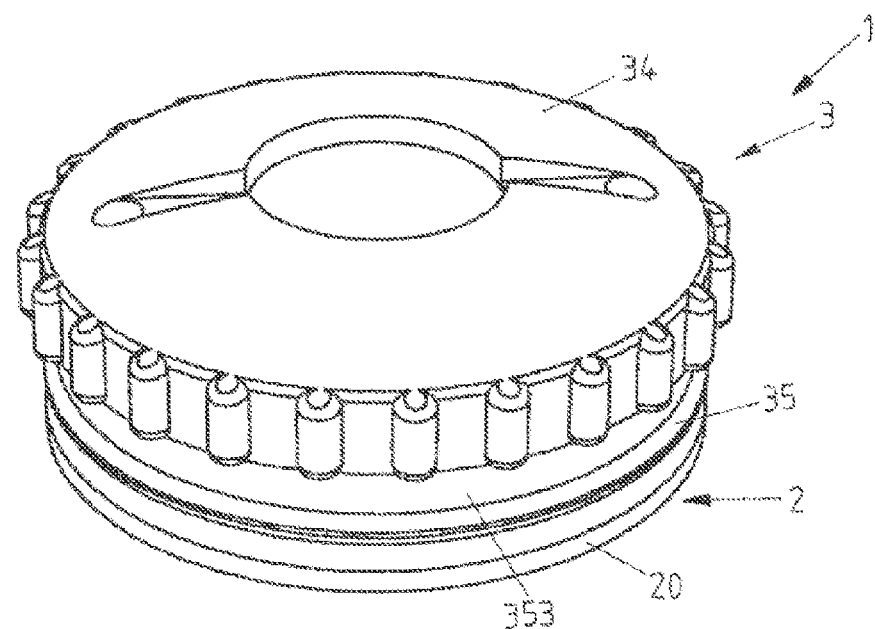
FIG. 15A shows a view of the fastener device during the rotation of a second fastener part with a winding element arranged thereon relative to a first fastener part.
Figure 15B:
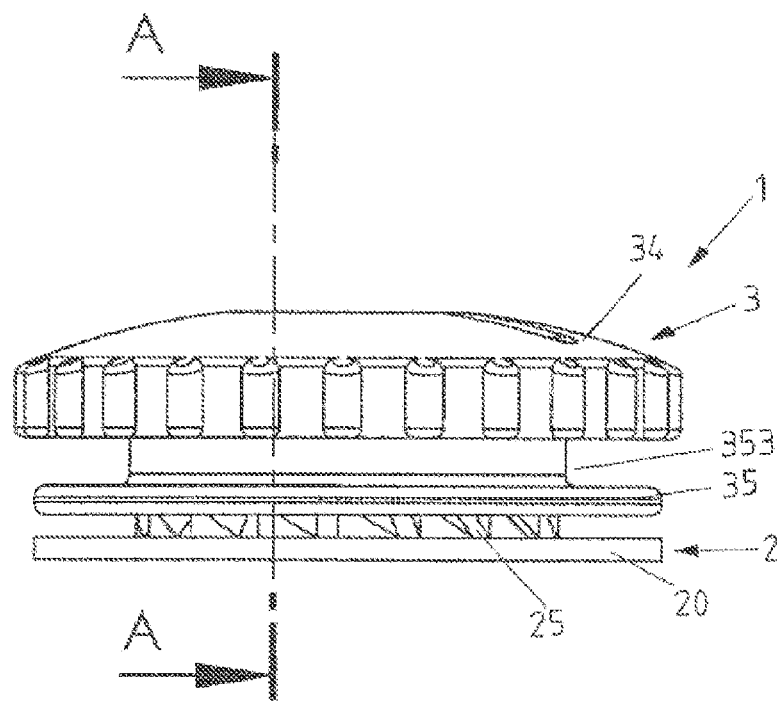
FIG. 15B shows a side view of the arrangement as per FIG. 15A.
Figure 16A:
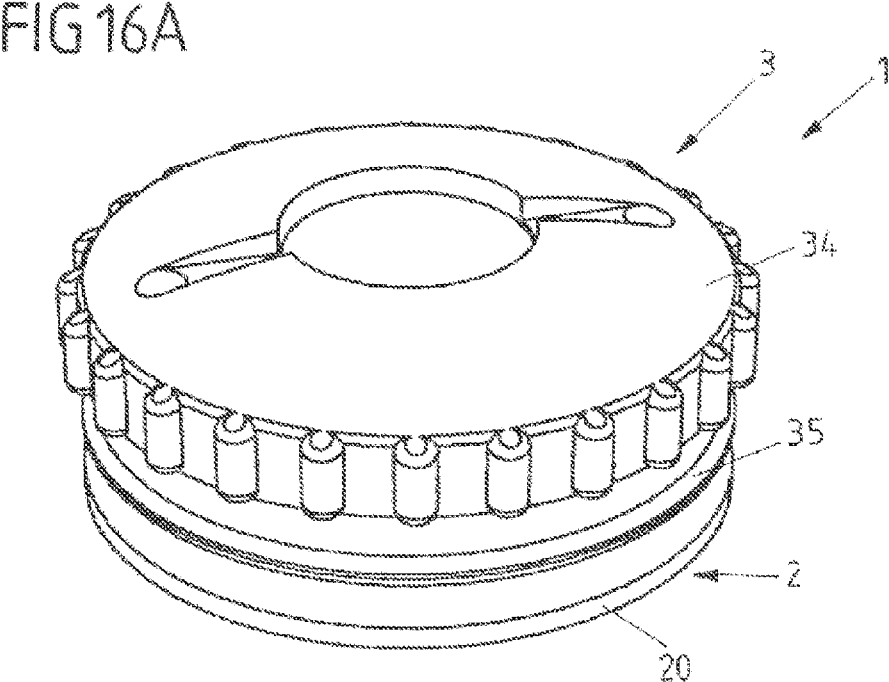
FIG. 16A shows a view of the fastener device during the further rotation of the second fastener part relative to the first fastener part.
Figure 16B:
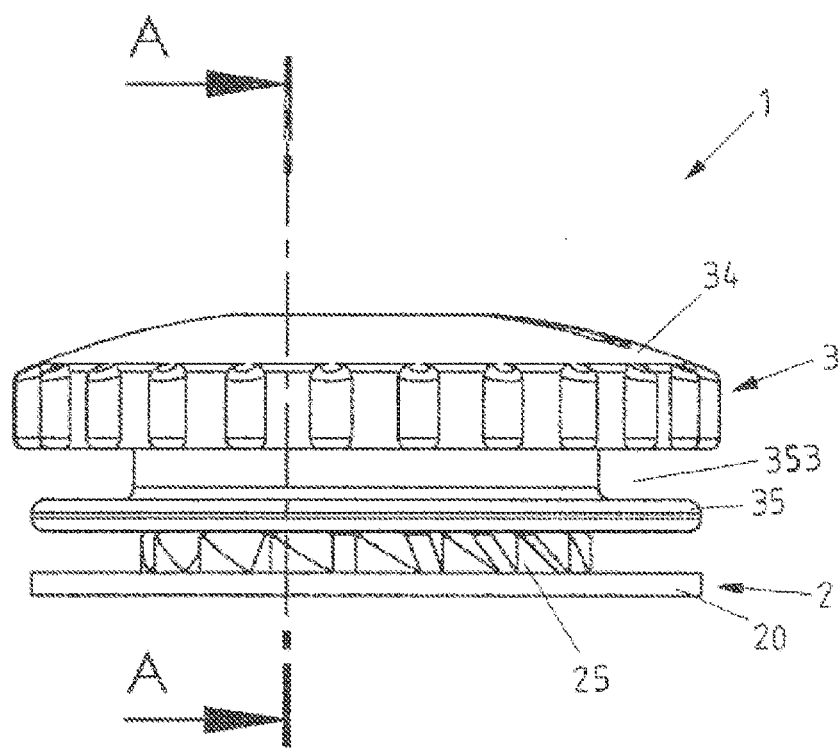
FIG. 16B shows a side view of the arrangement as per FIG. 16A.
Figure 16C:
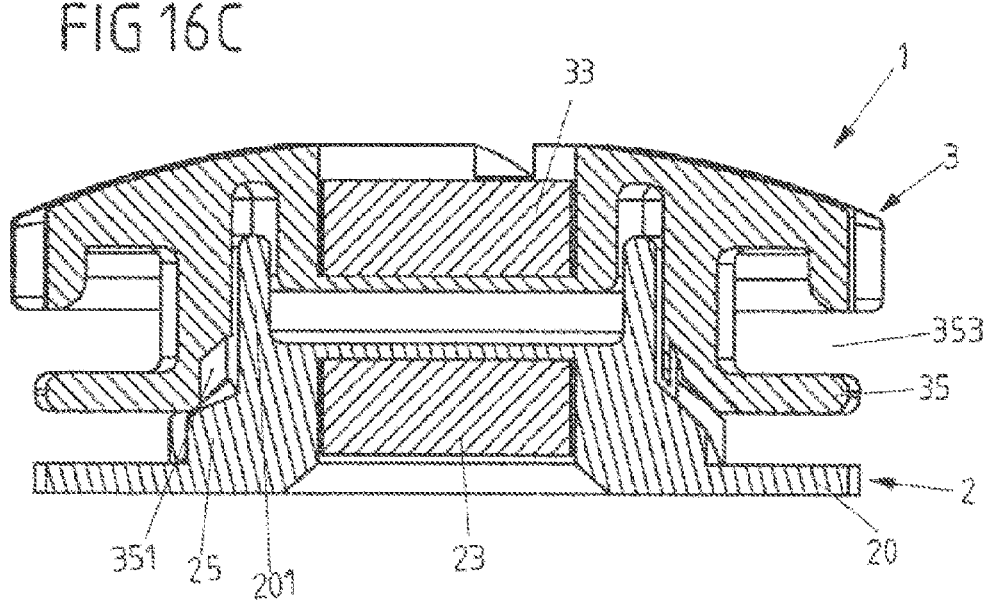
FIG. 16C shows a sectional view along the line A-A as per FIG. 16B.
Figure 16D:
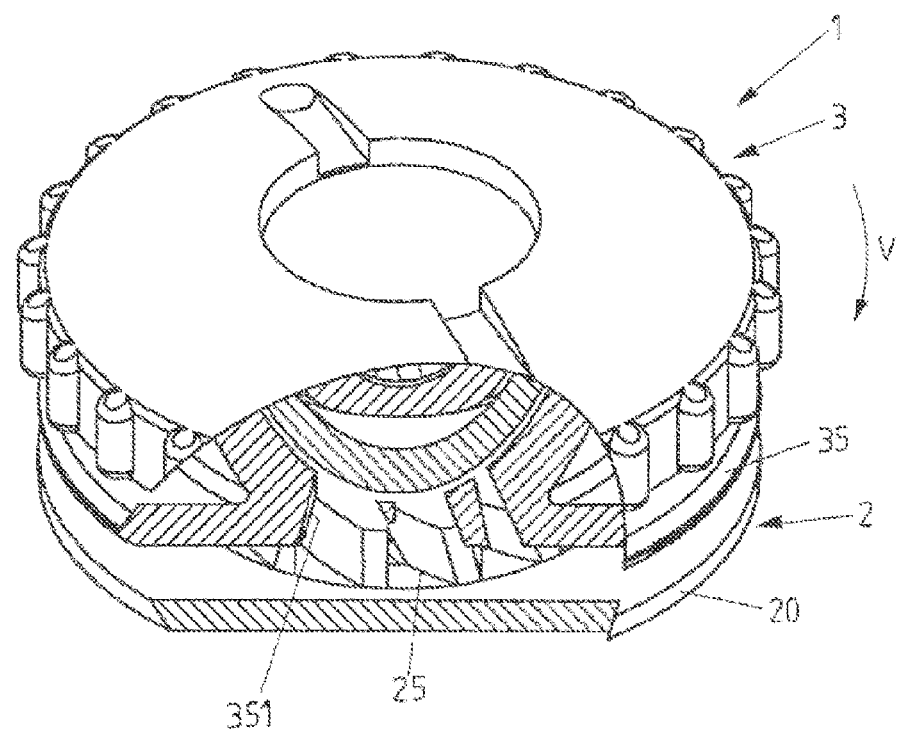
FIG. 16D shows a partially sectional view of the fastener device.
Figure 20A:
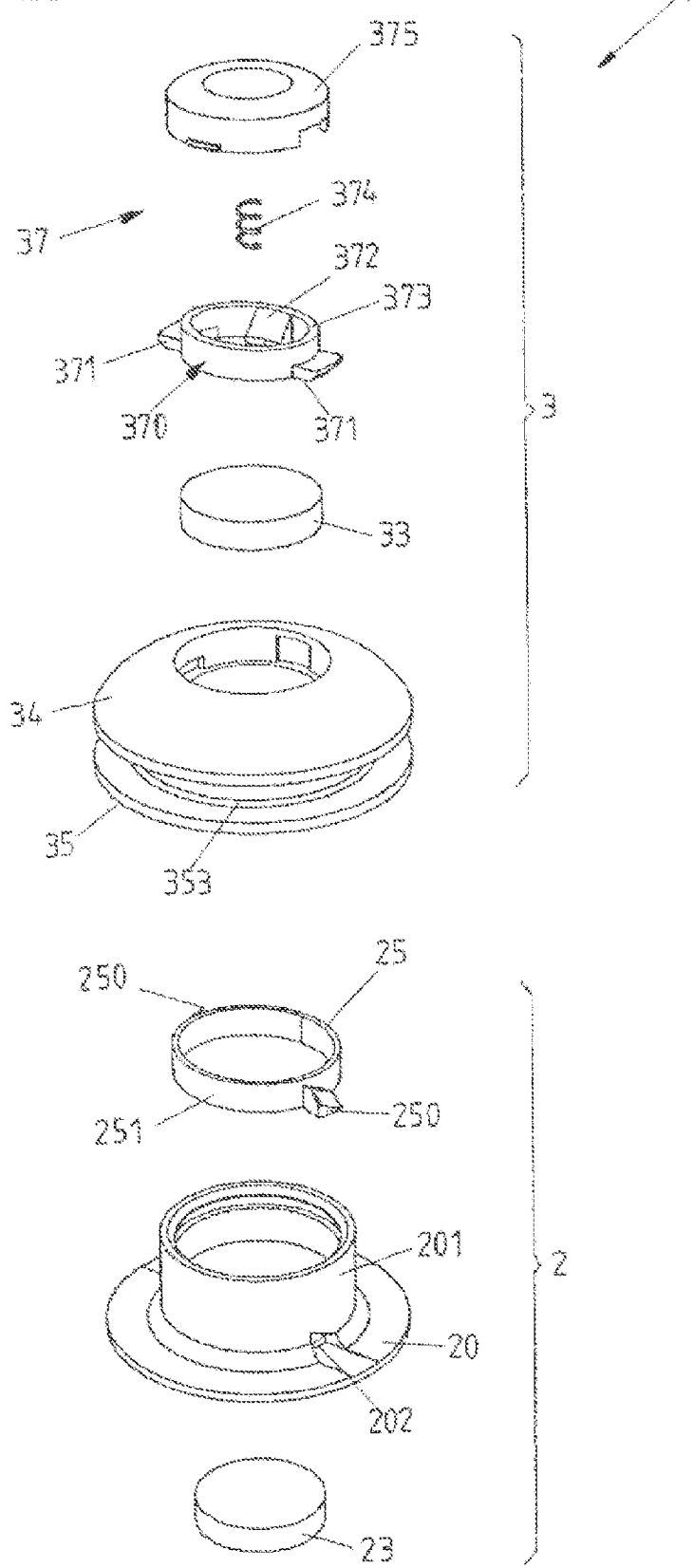
FIG. 20A shows an exploded view of the fastener device.
Figure 20B:
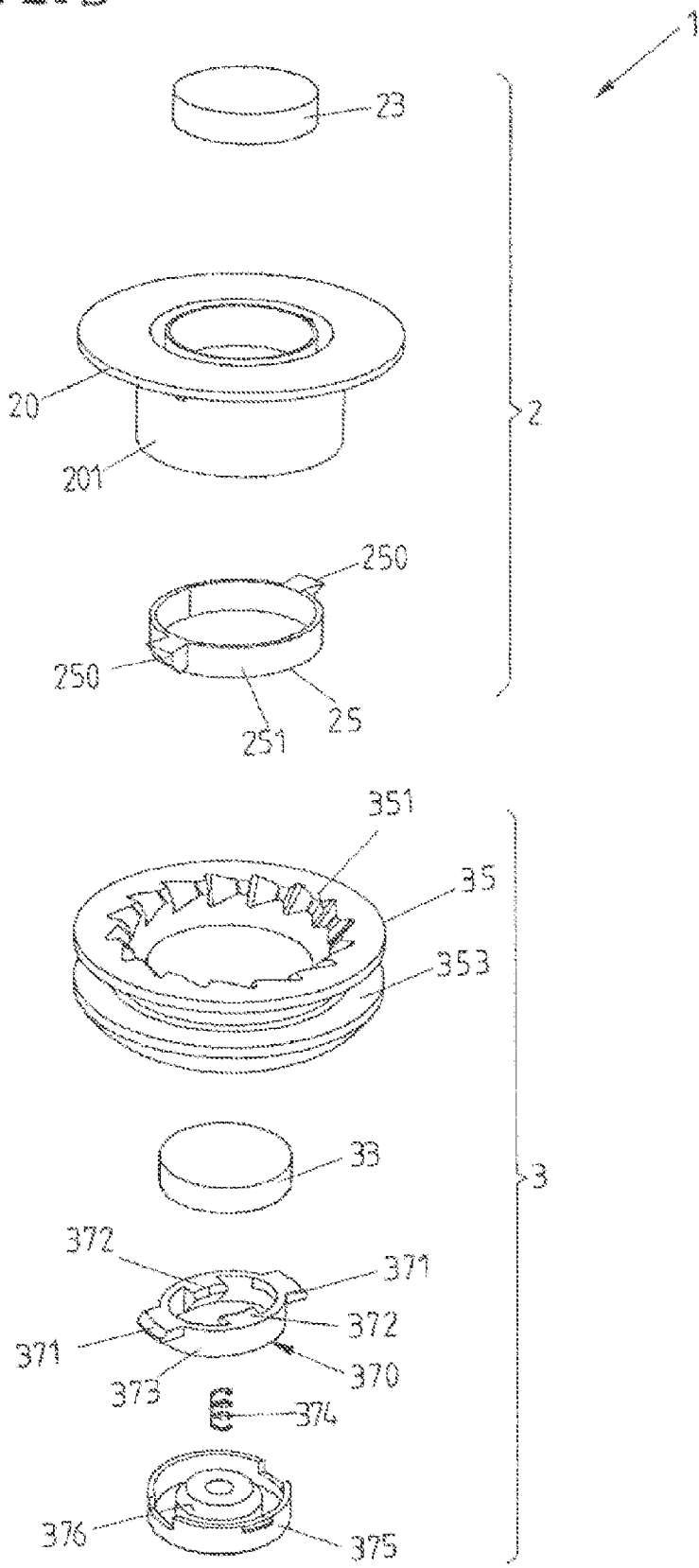
FIG. 20B shows another exploded view of the fastener device.

As can be seen from the exploded views in FIGS. 13A and 13B, the first fastener part 2 has a main body 20, on which a cylinder collar 201 is formed. Running in encircling fashion around the cylinder collar 201 is a toothing 25, the teeth of which have a sawtooth-like form. A magnet element 23 is also arranged on the main body 20.

The second fastener part 3 has an actuating element 34 to which a winding element 35 is connected fixedly, for example integrally. The winding element 35 has a channel 353 in which a tension element 4 can be received in order to be wound up on the winding element 35. On the actuating element 34, there is secured a magnet element 33 which interacts with magnetically attractive action with the magnet elements 23 on the first fastener part 2.

On a side facing toward the first fastener part 2, a toothing 351 is formed on the winding element 35. During the mounting of the fastener parts 2, 3 on one another, said toothing 351 of the winding element 35 engages with the toothing 25 on the main body 20 of the first fastener part 2, as illustrated in FIGS. 14A-14D.

When the fastener parts 2, 3 have been mounted on one another, it is furthermore the case that the cylinder collar 301 engages into the actuating element 34, and, by means thereof, is mounted rotatably and in axially movable fashion on the actuating element 34.

Both the toothing 351 of the winding element 35 and the toothing 25 of the first fastener part 2 have a sawtooth-like form. This makes it possible, as illustrated in FIGS. 15A-15D and 16A-16D, for the second fastener part 3 with the winding element 35 and the actuating element 34 to be moved in a winding direction V relative to the first fastener part 2, wherein here, the teeth of the toothings 25, 351 slide on one another and can be moved over one another, with the fastener parts 2, 3 being axially deflected relative to one another. The toothings 25, 351 thus provide a type of freewheel which, when the fastener parts 2, 3 have been mounted on one another, permits a rotation of the winding element 35 in the winding direction V, in order for a tension element 4 arranged on the winding element 35 to be tightened, but locks a movement counter to the winding direction V, such that the tension element 4 cannot be unwound with the fastener parts 2, 3 mounted on one another.

Owing to the magnetic interaction of the magnet elements 23, 33, the fastener parts 2, 3 are held against one another and, after a rotation, always pass into a position in which the toothings 25, 351 are in positively locking engagement with one another.

For the release of the fastener parts 2, 3 from one another, the fastener parts 2, 3 can be removed from one another counter to the closing direction X. In this way, the interaction between the toothings 25, 351 is also eliminated, such that the tension element 4 can be unwound from the winding element 35.

In the embodiment as per FIGS. 11A, 11B to 17A-17D, the second fastener part 3 as a whole together with the winding element 35 connected fixedly to the actuating element 34 is rotated. This yields a very simple fastener device 1.

In the embodiment as per FIGS. 11A, 11B to 17A-17D, the second fastener part 3 is, in the closed position, rotatable relative to the first fastener part 2 in the winding direction V. In an embodiment illustrated in FIGS. 18A, 18B it is the case, by contrast, that the toothings 25, 351 on the first fastener part 2, on the one hand, and on the second fastener part 3, on the other hand, are formed such that a rotation of the fastener parts 2, 3 relative to one another (in any direction) is not possible when the fastener parts 2, 3 have been mounted on one another, but is locked by means of the engagement of the toothings 25, 351.

In this embodiment, tightening of the tension element 4 by winding up onto the winding element 35 is thus possible only before the mounting of the fastener parts 2, 3 on one another. Likewise, the tension element 4 can be relaxed again only after the removal of the fastener parts 2, 3 from one another.

In an embodiment illustrated in FIGS. 19A, 19B to 26A-26D, a first fastener part 2 has a main body 20 on which there is formed a cylinder collar 201 which surrounds a toothing means 25 with toothing elements 250 which are connected to one another by means of a ring 251. In an assembled position, the toothing elements 250 project radially outward through apertures 202 in the cylinder collar 201 and can be placed in operative connection with a toothing 351 on a winding element 35 of a second fastener part 3.

The second fastener part 3 has an actuating element 34 which is fixedly connected to the winding element 35. On the actuating element 34, there is arranged a detent means 37 which has a detent element 370 with detent projections 371 connected by means of a ring-shaped preload element and which is operated by means of an operating element 375.

Figure 21A:
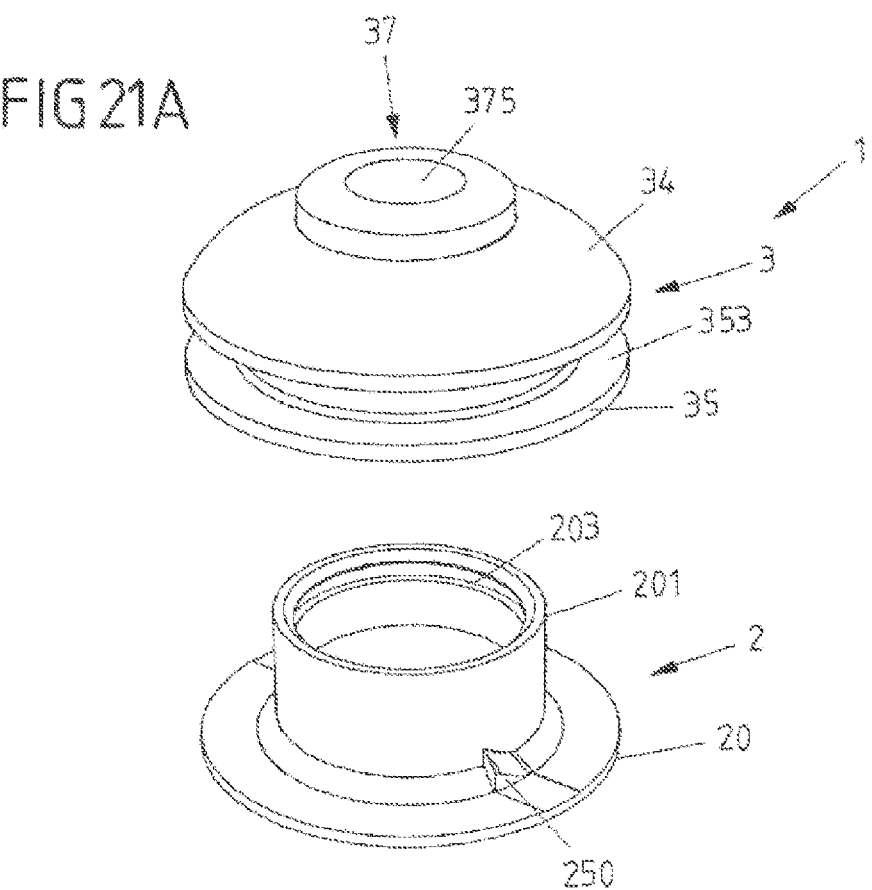
FIG. 21A shows a view of the fastener device prior to the mounting of the fastener parts on one another.
Figure 21B:
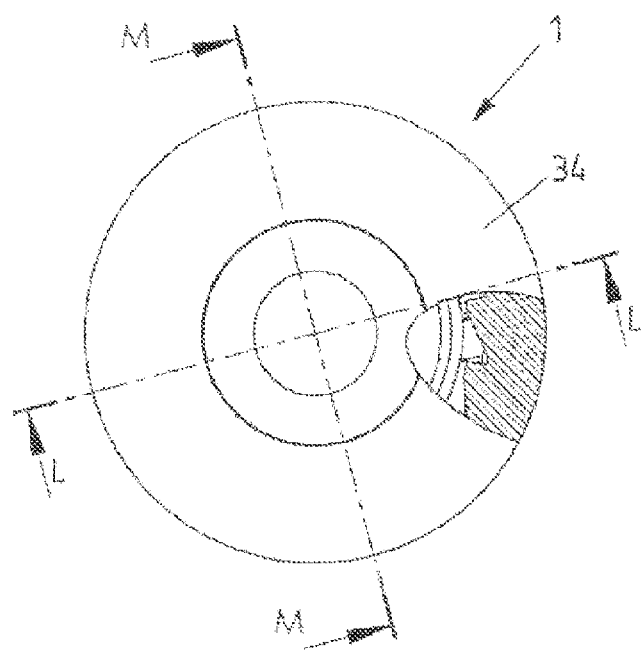
FIG. 21B shows a partially sectional plan view of the arrangement as per FIG. 21A.
Figure 22A:
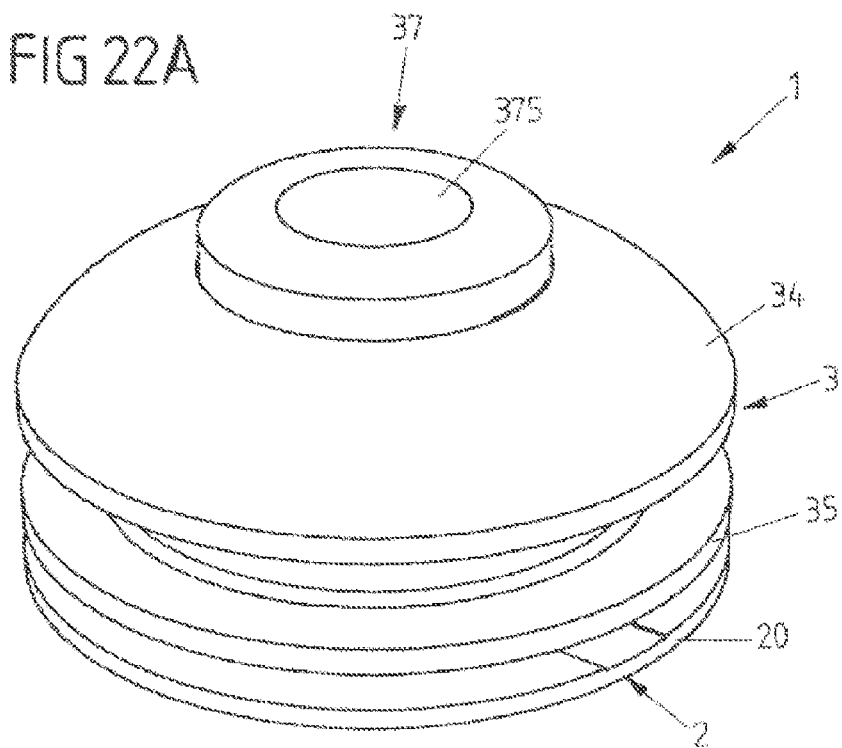
FIG. 22A shows a view of the fastener device during the closing process.
Figure 22B:
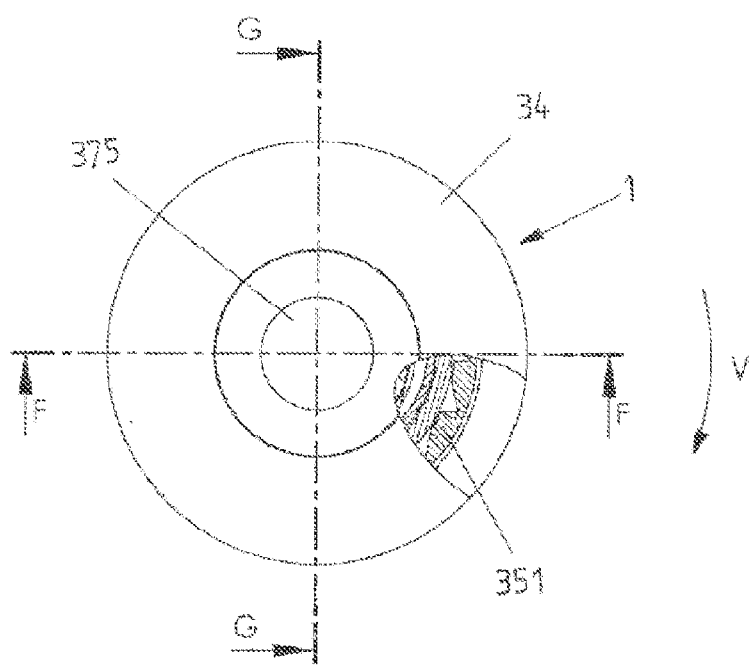
FIG. 22B shows a partially sectional plan view of the arrangement as per FIG. 22A.
Figure 23A:
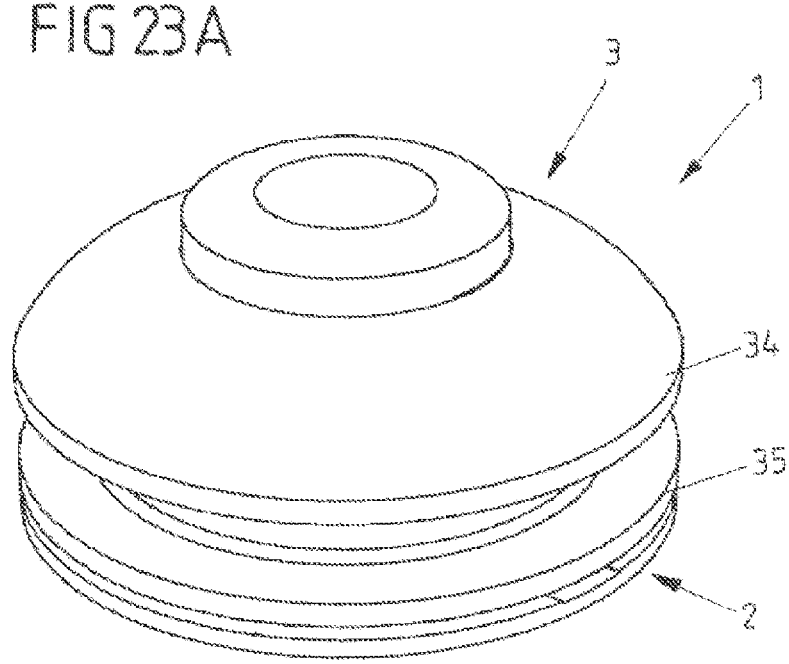
FIG. 23A shows a view of the fastener device during the further closing process.
Figure 23B:
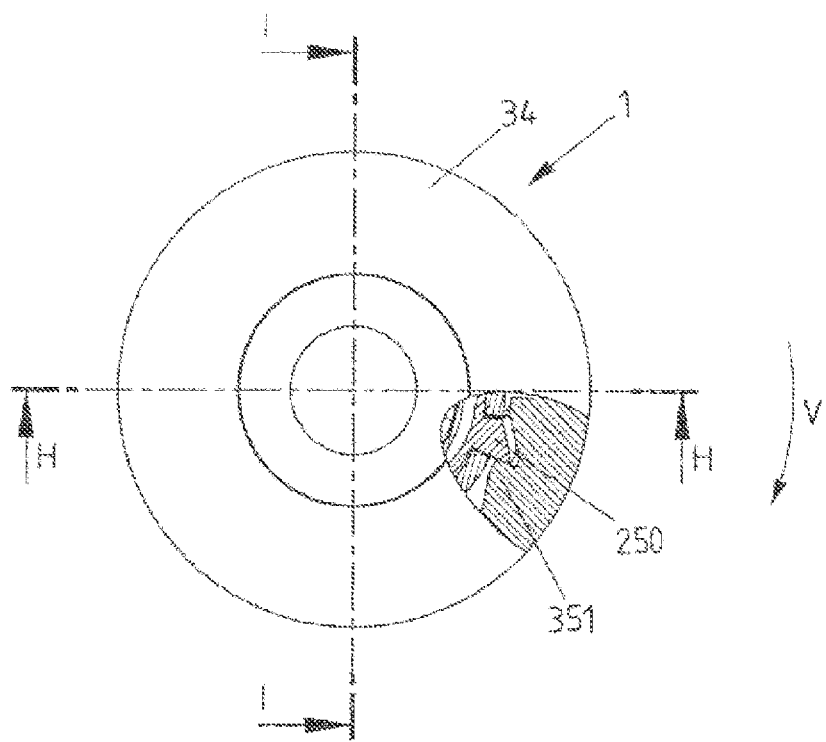
FIG. 23B shows a partially sectional plan view of the arrangement as per FIG. 23A.

As can be seen for example from the sectional view in FIG. 21C, the detent means 37 is received in a body 340 of the actuating element 34 and projects with its detent projections 371 radially from the body 340. During the mounting of the fastener parts 2, 3 on one another, as illustrated in FIGS. 22A-22D, the cylinder collar 201 of the first fastener part 2 engages axially into the actuating element 34 and engages around the body 340 of the actuating element 34, such that, as can be seen from FIGS. 23A-23D and 24A-24D, the detent projections 371 are forced aside in a radially inward direction and finally, in the closed position of the fastener device 1 as per FIGS. 24A-24D, engage with a detent recess 203 in the form of an encircling annular groove at the inside on the cylinder collar 201.

In the closed position, the fastener parts 2, 3 are thus detained together, such that the fastener parts 2, 3 are axially held in position relative to one another by the detent means 37.

Figure 24A:
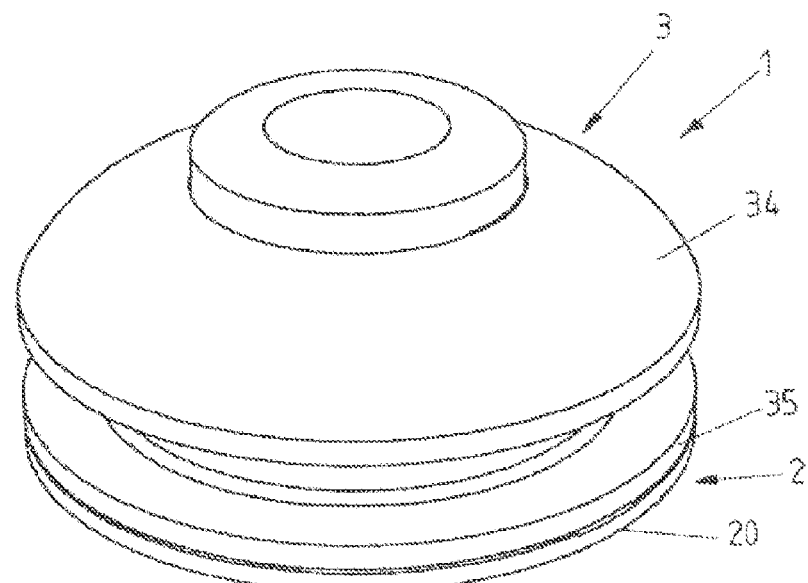
FIG. 24A shows a view of the fastener device in a closed position.
Figure 24B:
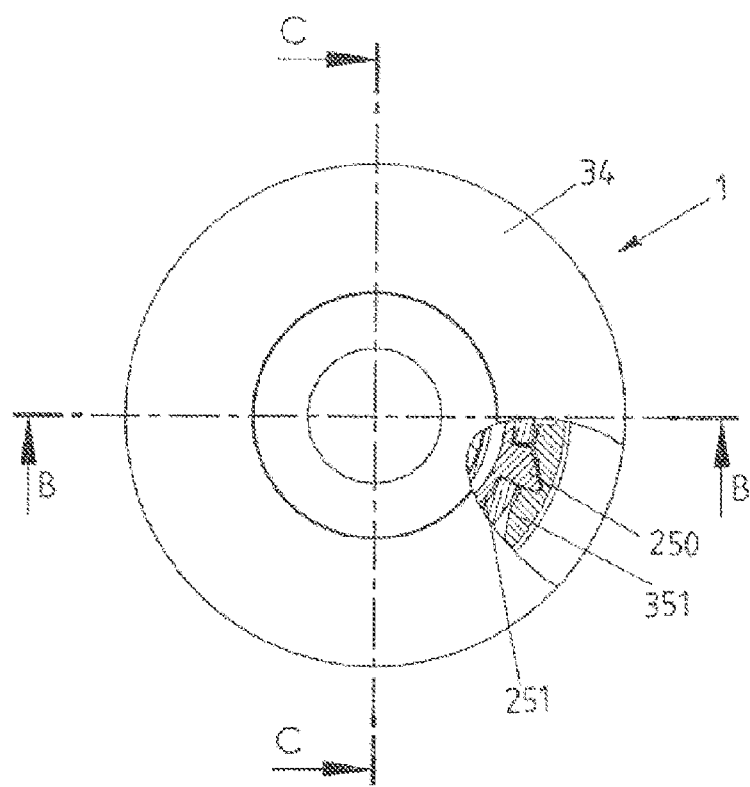
FIG. 24B shows a partially sectional plan view of the arrangement as per FIG. 24A.
Figure 25A:
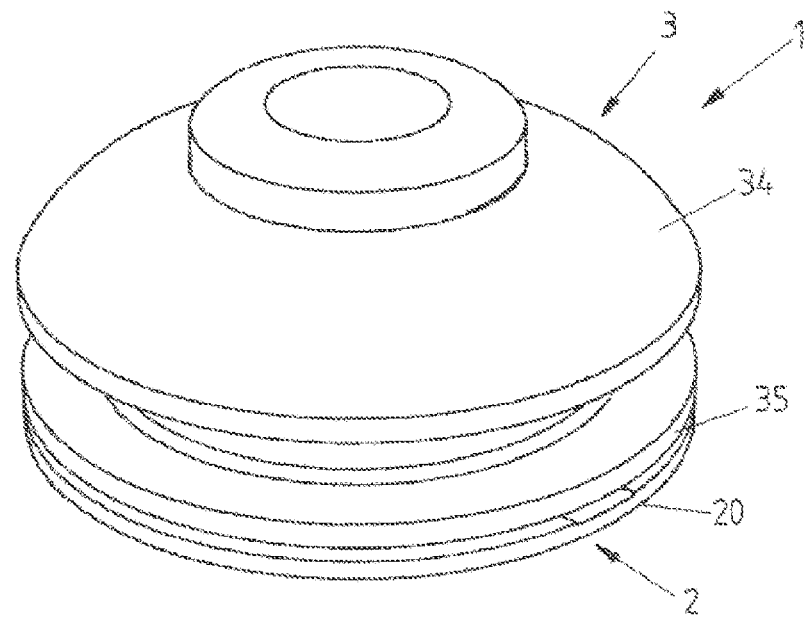
FIG. 25A shows a view of the fastener device during the rotation of the fastener parts relative to one another.
Figure 25B:
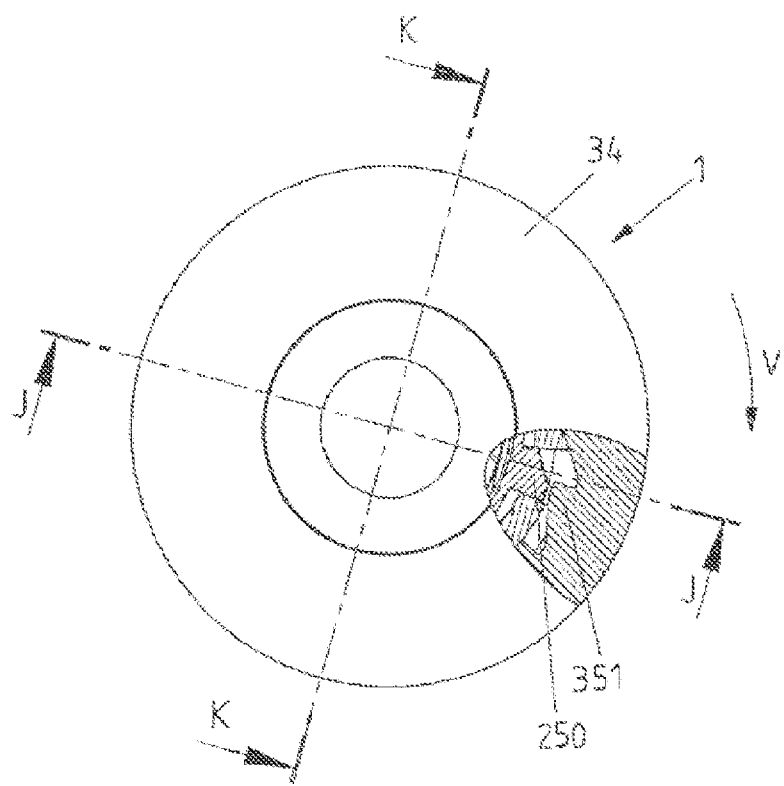
FIG. 25B shows a partially sectional plan view of the arrangement as per FIG. 25A.
Figure 25C:
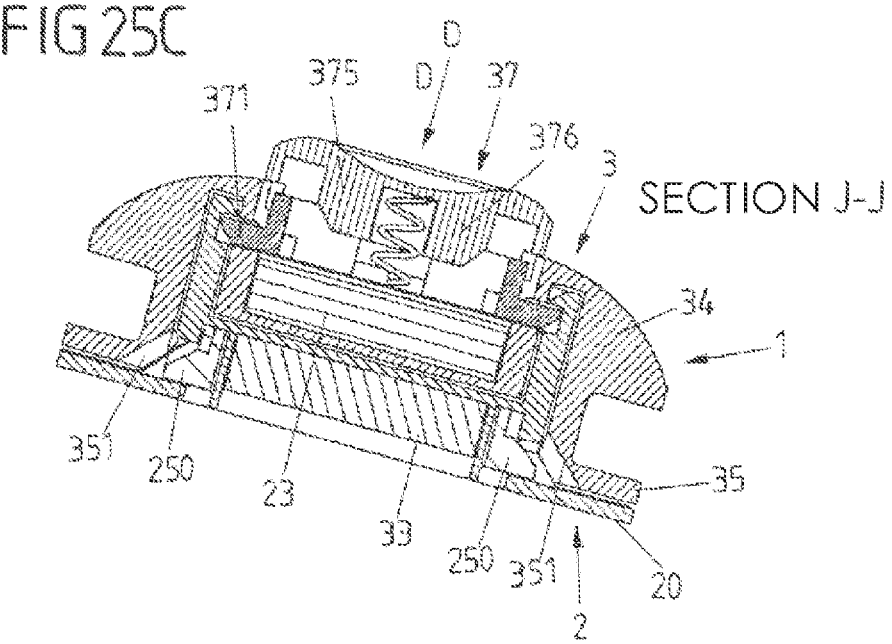
FIG. 25C shows a sectional view along the line J-J as per FIG. 25B.
Figure 25D:
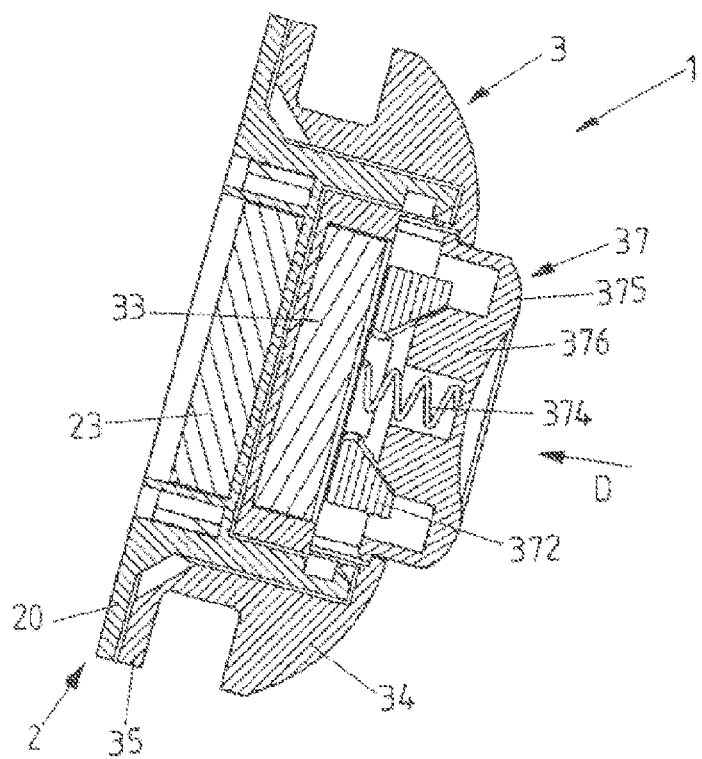
FIG. 25D shows a sectional view along the line K-K as per FIG. 25B.

During the mounting of the fastener parts 2, 3, the toothings 25, 351 engage with one another, as can be seen for example from the partially sectional view as per FIG. 24B. The actuating element 34 is in this case movable together with the winding element 35 in a winding direction V relative to the first fastener part 2, wherein, here, as can be seen from FIGS. 25A-25D, the toothing elements 250 are forced aside by the teeth of the toothing 351 of the winding element 35 and are thus pushed radially inward into the cylinder collar 201.

The winding element 35 can thus be rotated in the winding direction V in order to wind up the tension element 4. A rotational movement of the winding element 35 relative to the first fastener part 2 counter to the winding direction V is however locked owing to the engagement of the toothing elements 250 on the first fastener part 2 with the toothing 351 on the second fastener part 3, such that unwinding of the tension element 4 from the winding element 35 is not possible.

During a rotation of the winding element 35 relative to the first fastener part 2, the first fastener part 2 and the second fastener part 3 remain axially in position relative to one another owing to the detent engagement by means of the detent means 37. The rotation of the winding element 35 is in this case possible by means of the radial displacement of the toothing elements 250 of the toothing 25 of the first fastener part 2.

Figure 26A:
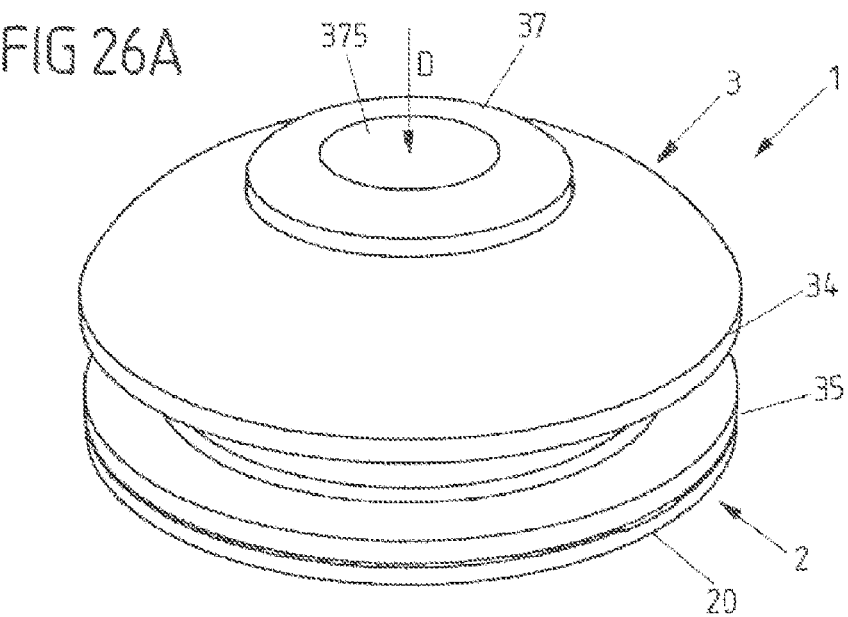
FIG. 26A shows a view of the arrangement during actuation of an operating element for the purposes of opening the fastener device.
Figure 26B:
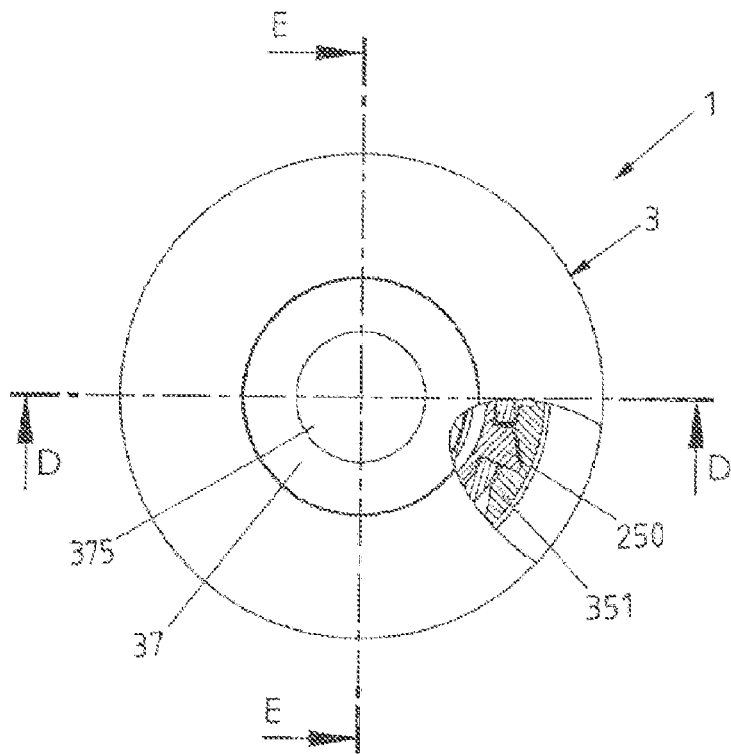
FIG. 26B shows a partially sectional plan view of the arrangement as per FIG. 26A.
Figure 26C:
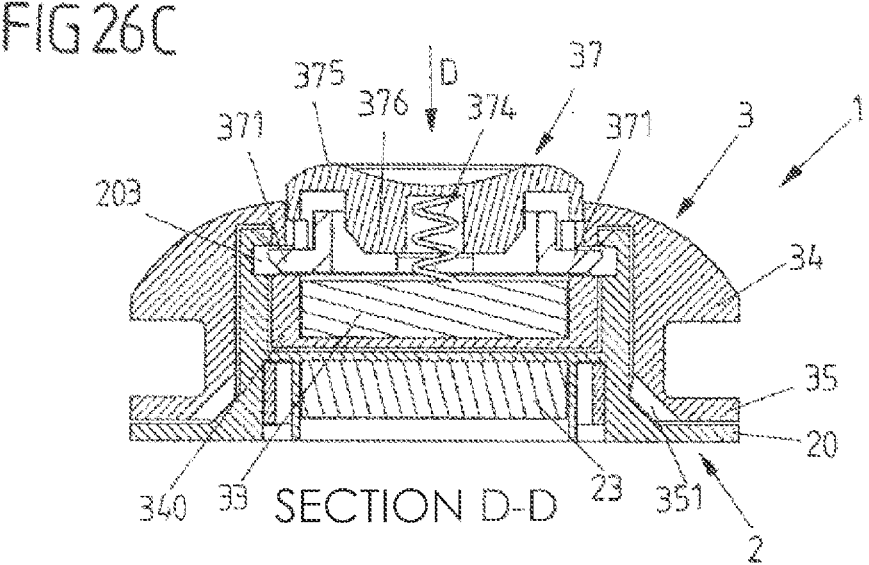
FIG. 26C shows a sectional view along the line D-D as per FIG. 26B.
Figure 26D:
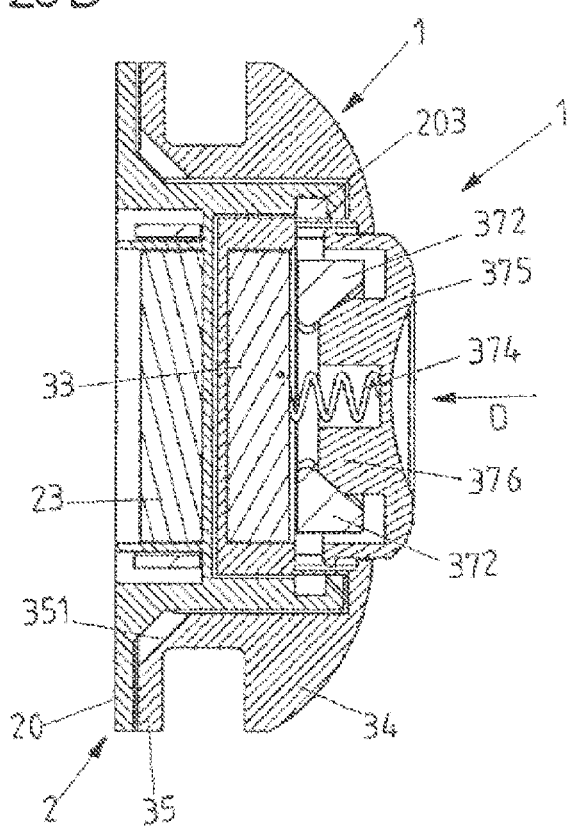
FIG. 26D shows a sectional view along the line E-E as per FIG. 26B.

To release the fastener parts 2, 3 from one another, a user can manually push on the operating element 375 on the actuating element 34 (actuating direction D in FIG. 26A). As a result, the operating element 375 runs with a run-on element 376, on which run-on bevels are formed, onto beveled run-on elements 372 which are formed on the annular preload element 373, and thus deforms the preload element 373. In this way, as can be seen from FIG. 26C, the detent projections 371 are pulled radially inward, such that the engagement between the detent elements 371 and the detent recess 203 on the cylinder collar 201 is eliminated, and the fastener parts 2, 3 can be removed from one another axially counter to the closing direction X.

It is also the case in the embodiment as per FIGS. 19A, 19B to 26A-26D that each fastener part 2, 3 has a magnet element 23, 33, which magnet elements interact with magnetically attractive action during the mounting of the fastener parts 2, 3 and thus magnetically assist mounting of the fastener parts 2, 3 on one another.

FIGS. 27A to 27D show another embodiment which, with regard to the toothings 25, 351 that act between the first fastener part 2 and the winding element 35, is of similar design to the embodiment described above on the basis of FIGS. 11A, 11B to 17A-17B, such that, in this regard, reference is made to the explanations above.

The embodiment as per FIGS. 27A to 27D has a detent means 37 which is arranged on the second fastener part 3 and which serves for detaining the fastener parts 2, 3 together in the closed position such that the second fastener part 3 is held with detent action and thus positively locking action on the first fastener part 2 counter to the closing direction X.

The use of a detent means 37 of said type permits a non-magnetic form of the fastener device 1. It is thus basically possible for magnet elements to be omitted in the fastener device 1. It is however also conceivable and possible for magnet elements to also be used in addition to the detent means 37.

The detent means 37 has an engagement element 38 which is received with an annular collar 381 in axially movable fashion in a receiving space within the actuating element 34 and which is spring-preloaded relative to the actuating element 34 by means of a spring element 384 in the form of a spiral spring. On a cylindrical body 380 which extends from the annular collar 381, receiving openings 382 are formed diametrically opposite one another, in which receiving openings there are received detent elements 385 in the form of balls which serve for engaging, in the closed position of the fastener device 1 (FIG. 27D), with detent action into a detent recess 203 in the form of an annular groove running in encircling fashion on the inner side of the cylinder collar 201 of the first fastener part 2, such that, by means thereof, as can be seen from FIG. 27D, there is detent engagement between the engagement element 38, which in the closed position engages into a of the cylinder collar 201, and the cylinder collar 201, and, by means thereof, the fastener parts 2, 3 are detained together.

Within a central opening 383 of the engagement element 38, an operating element 39 is guided axially along the closing direction X. The operating element 39 has a cylindrical design, is supported elastically on the first fastener part 2 in the closed position by means of a spring element 394 situated in an opening 393 in the form of a blind bore, and is furthermore in contact, by means of an annular collar 391 at an end side, in a travel-limiting manner with the engagement element 38 when said operating element not actuated relative to the engagement element 38.

Figure 27D:
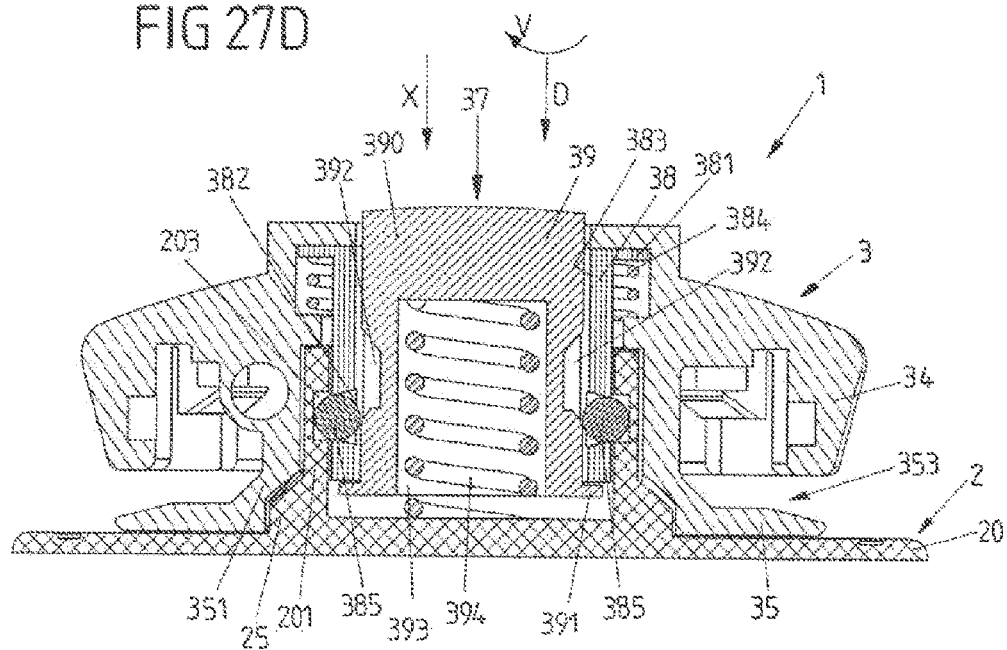
FIG. 27D shows a sectional view along the line A-A as per FIG. 27C.

As can be seen from FIG. 27D, the operating element 39 has, on its outer circumferential surface, two diametrically oppositely situated unlocking openings 392, which, in the closed position, are arranged at an axially different height in relation to the detent elements 385, such that the detent elements 385 are in contact with the outer circumferential surface of the cylindrical body 390 of the operating element 39 and, by means thereof, are held in detent engagement with the detent recess 203 on the inner side of the cylinder collar 201.

In the closed position (FIG. 27D), the actuating element 34 is, owing to the spring preload of the spring element 384, pushed in the direction of the first fastener part 2 and, owing to contact of the base surface 240 against the annular collar 354 of the winding element 35, the winding element 35 is pushed into engagement with the toothing 25 of the first fastener part 2. In the closed position, the second fastener part 3 is thus held with detent action on the first fastener part 2, with toothing engagement between the winding element 35 and the first fastener part 2.

If, in the closed position of the fastener device 1, the actuating element 34 and thus the winding element 35 together with the actuating element 34 are rotated in the winding direction V, the toothings 25, 351 slide over one another, which causes a (small) axial movement of the winding element 35 and, by means thereof, of the actuating element 34. Here, because the engagement element 38 of the detent means 37 is held axially fixed relative to the cylinder collar 201 of the first fastener part 2 by means of the detent elements 385, the axial deflection of the winding element 35 and of the actuating element 34 takes place counter to the spring preload of the spring element 384.

After rotation of the actuating element 34 and of the winding element 35, the toothings 25, 351 then engage with one another again owing to the spring preload of the spring element 384.

For the release of the fastener parts 2, 3 from one another, a user can push the operating element 39 into the engagement element 38 in an actuating direction D. In this way, the body 390 of the operating element 39 is adjusted axially along the closing direction X within the engagement element 38, such that the unlocking openings 392 move to the same axial height as the detent elements 385, and the detent elements 385 can thus deflect radially inward. In this way, the locking detent engagement between the engagement element 38 and the cylinder collar 201 is eliminated, such that the fastener parts 2, 3 can be removed from one another counter to the closing direction X.

For the closing of the fastener device 1 again, the second fastener part 3 can be mounted onto the first fastener part 2 again in the closing direction X, whereby the engagement element 38 engages with the opening of the cylinder collar 201 and the detent elements 385 engage with detent action into the detent recess 203 in the form of the encircling groove within the cylinder collar 201. In this way, the toothings 25, 351 also enter into toothing engagement with one another, and the fastener device 1 assumes the closed position illustrated in FIG. 27D.

Figure 28:
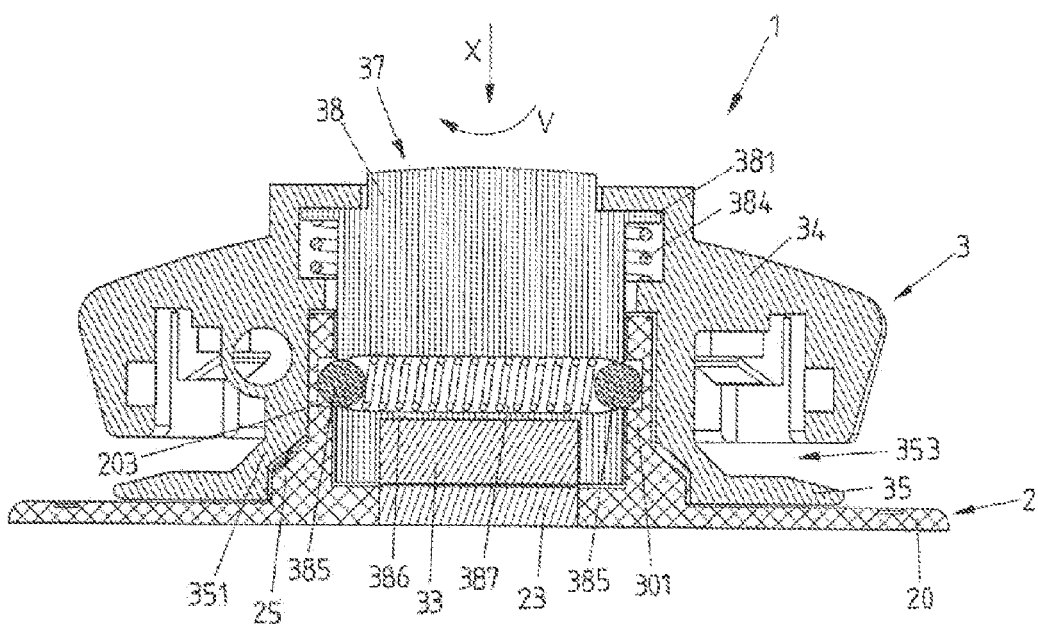
FIG. 28 shows a sectional view along the line A-A as per FIG. 27C of a modified embodiment.

FIG. 28 shows an embodiment which is modified in relation to the embodiment as per FIGS. 27A-27D and which is similar in terms of its external appearance to the embodiment as per FIGS. 27A-27D. In the embodiment as per FIG. 28, the detent means 37 has an engagement element 38 on which there is formed a continuous bore 387 which extends transversely with respect to the closing direction X and in which two spherical detent elements 385 are arranged and preloaded relative to one another by means of a spring element 386. When the fastener parts 2, 3 are mounted on one another, the engagement element 38 engages with the cylinder collar 201, and the detent elements 385 engage with detent action with the detent recess 203 on the inner side of the opening of the cylinder collar 201, as can be seen from FIG. 28.

Here, the detent engagement is maintained in the closed position owing to the spring preload by means of the spring element 386. If it is intended to release the detent engagement, then the second fastener part 3 can, with sufficient exertion of force, be pulled off the first fastener part 2 counter to the closing direction X, whereby the detent elements 385 are automatically, by running onto the upper edge of the groove-like detent recess 203, offset radially inward and thus disengaged from the detent recess 203. The detent engagement between the fastener parts 2, 3 can thus be released without separate actuation of the engagement element 38.

The embodiment as per FIG. 28 is of magnetic form by virtue of the fact that a magnet element 23 is arranged on the body 20 of the first fastener part 2 and, furthermore, a magnet element 33 is arranged on the body 380 of the engagement element 38, as can be seen from the sectional view as per FIG. 28. The fastener parts 2, 3 thus (also) magnetically interact, which facilitates the mounting of the fastener parts 2, 3.

The embodiment as per FIG. 28 may however also be of purely mechanical form without magnet elements.

In the embodiments described above, the toothing means 25, 351 on the first fastener part 2 and on the second fastener part 3 may basically be designed very differently in order, in the closed position, to produce positive locking hold (which can withstand load at least up to a certain threshold torque) between the fastener parts 2, 3.

FIGS. 29A, 29B to 33A, 33B show different embodiments of toothing means 25, 351 which differ in terms of the geometry of their teeth and which can be used in a fastener device 1 of the type described here.

Figure 29A:
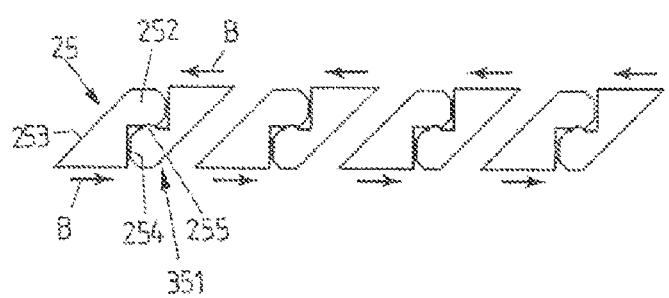
FIG. 29A shows a schematic view of an embodiment of toothing means.
Figure 29B:
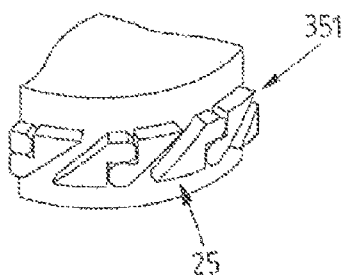
FIG. 29B shows a perspective view of the toothing means as per FIG. 29A.

Accordingly, in the embodiment as per FIGS. 29A, 29B, the teeth of each toothing means 25, 351 have a tooth flank which extends obliquely relative to the closing direction X and which is in the form of a run-on bevel 253, and an approximately vertically extending tooth flank 254 with a projection element 252 which is formed on said tooth flank and which projects along the winding direction V. In the event of a load acting in a loading direction B opposite to the winding direction V, the projection elements 252 of the teeth of the toothing means 25, 351 engage with one another, such that a movement of the toothing means 25, 351 in the loading direction B (counter to the winding direction V) is blocked. The winding element 35 thus cannot be rotated in the loading direction B counter to the winding direction V relative to the first fastener part 2 when the fastener device 1 is situated in its closed position.

In the embodiment as per FIGS. 29A, 29B, a detent lug 255 is additionally formed on the projection element 252 of each tooth (or at least some of the teeth) of the toothing means 351, which detent lug can engage with detent action with an associated detent hollow on the projection element 252 of an associated tooth of the toothing means 25 in order to additionally lock the locking engagement of the teeth of the toothing means 25, 351 in the event of load acting in the loading direction B.

Figure 30A:
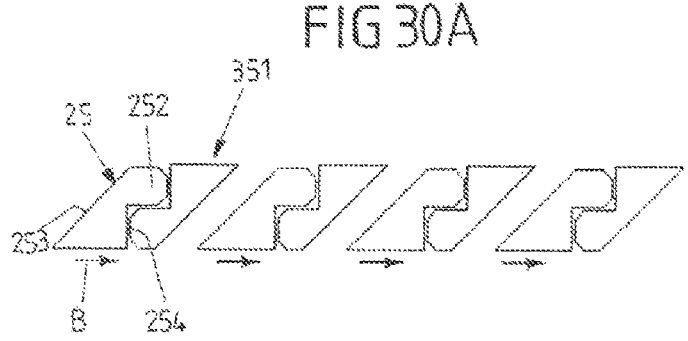
FIG. 30A shows a schematic view of another embodiment of toothing means.
Figure 30B:
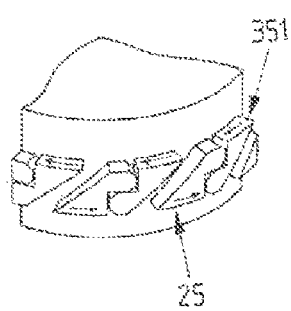
FIG. 30B shows a perspective view of the toothing means as per FIG. 30A.

The embodiment as per FIGS. 30A, 30B is identical to the exemplary embodiment as per FIGS. 29A, 29B aside from the fact that, in the exemplary embodiment as per FIGS. 30A, 30B, no detent lugs 255 as in the exemplary embodiment as per FIGS. 29A, 29B are provided on the projection elements 252 of the teeth of the toothing means 351.

Figure 31A:
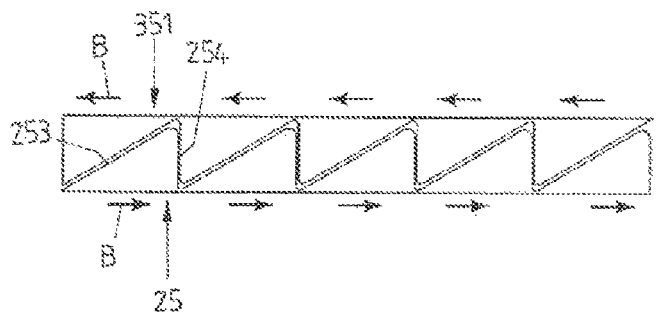
FIG. 31A shows a schematic view of yet another embodiment of toothing means.
Figure 31B:
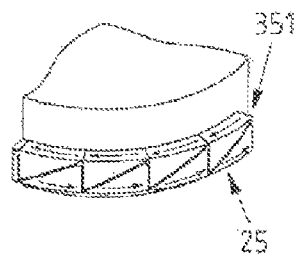
FIG. 31B shows a perspective view of the toothing means as per FIG. 31A.

In the embodiment as per FIGS. 31A, 31B, the toothing means 25, 351 are in the form of sawtooth-like toothings. The teeth of the toothing means 25, 351 in this case have in each case one tooth flank in the form of a run-on bevel 253 and one vertically extending tooth flank 254. A loading of the toothing means 25, 351 in a loading direction B opposite to the winding direction V is locked.

Figure 32A:
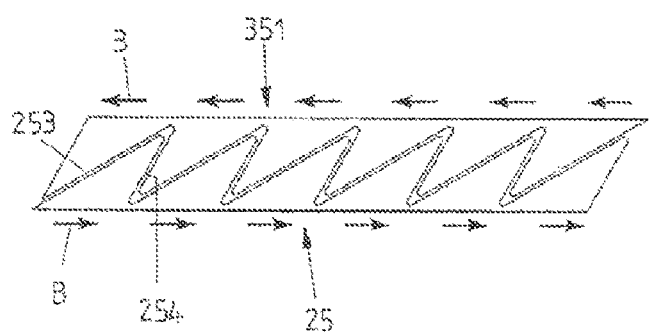
FIG. 32A shows a schematic view of yet another embodiment of toothing means.
Figure 32B:
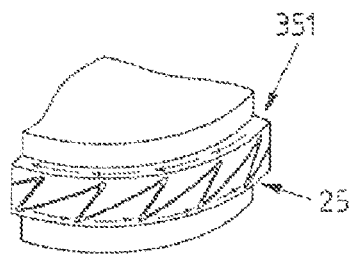
FIG. 32B shows a perspective view of the toothing means as per FIG. 32A.

In an embodiment illustrated in FIGS. 32A, 32B, the teeth of the toothing means 25, 351 are, in relation to the embodiment as per FIGS. 31A, 31B, undercut at the tooth flanks 254, that is to say are inclined obliquely relative to the closing direction X. In the event of the toothing devices 25, 351 being subjected to load in a loading direction B opposite to the winding direction V, the toothing means 25, 351 are locked relative to one another.

In the embodiments as per FIGS. 29A, 29B, 30A, 30B and 32A, 32B, the engagement of the toothing means 25, 351 is self-boosting in the event of load acting in the loading direction B. The fastener parts 2, 3 are thus pulled toward one another in the closing direction X under the action of load. Owing to the positive locking by means of the projection elements 252 or owing to the undercut, the fastener device 1 is furthermore also locked against opening counter to the closing direction X. It is in particular also possible for loading forces which act not purely tangentially, but rather with a component counter to the closing direction X, to be accommodated and dissipated.

Figure 33A:
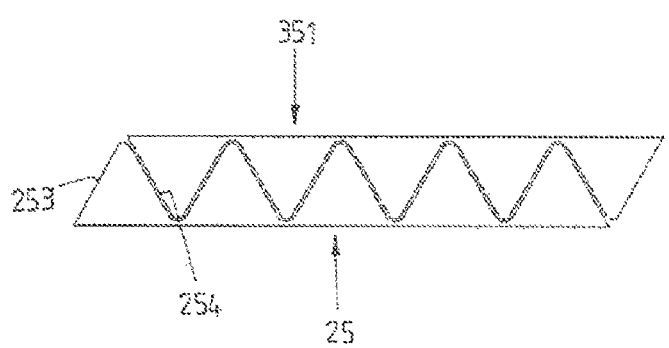
FIG. 33A shows a schematic view of yet another embodiment of toothing means.
Figure 33B:
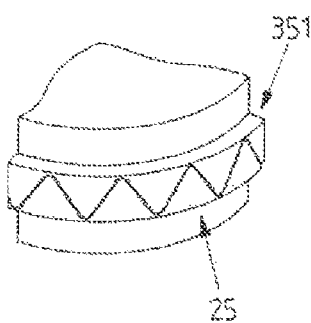
FIG. 33B shows a perspective view of the toothing means as per FIG. 33A.
Figure 34A:
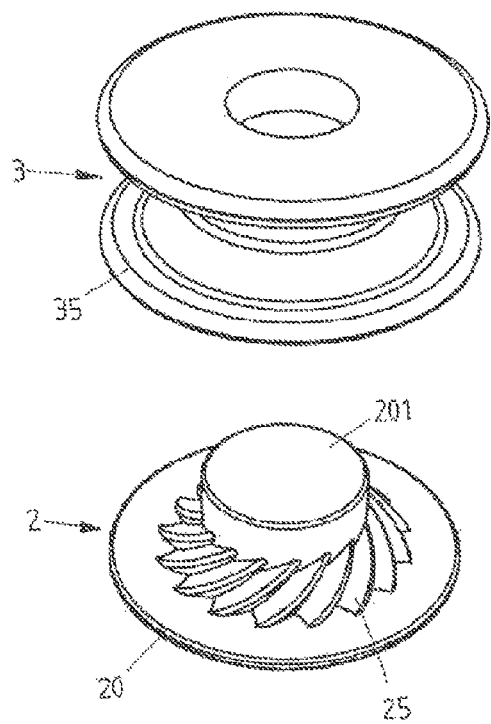
FIG. 34A shows a view of an embodiment of a fastener device, illustrating in particular a toothing means on the first fastener part.
Figure 34B:
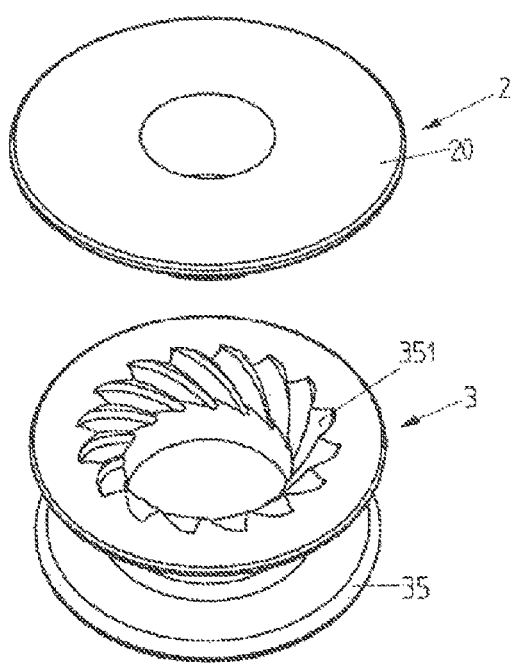
FIG. 34B shows a view of the embodiment as per FIG. 34A, illustrating a toothing means on the second fastener part.
Figure 34C:
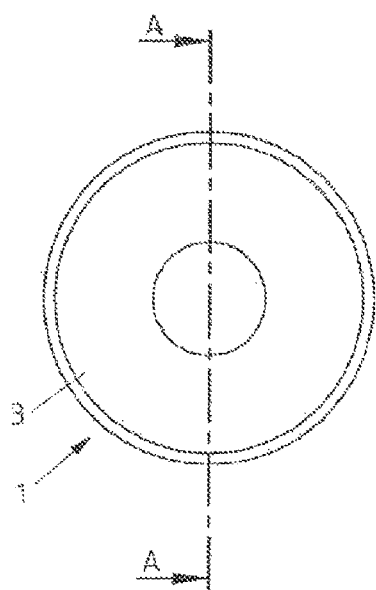
FIG. 34C shows a plan view of the fastener device.
Figure 34D:
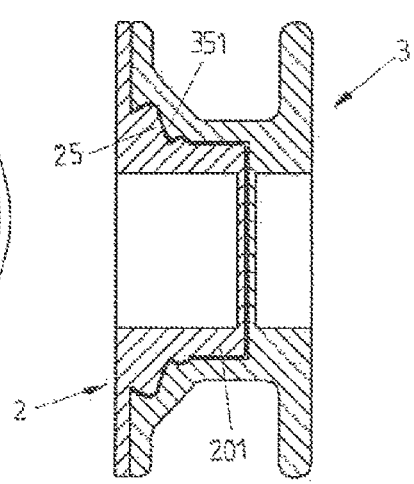
FIG. 34D shows a sectional view along the line A-A as per FIG. 34C.

In the embodiment as per FIGS. 33A, 33B, the teeth of the toothing means 25, 351 are inclined obliquely at both tooth flanks 253, 254 such that they form a run-on bevel and, when a sufficient force acts between the toothing means 25, 351, the toothing means 25, 351 can slide over one another in the winding direction V and also counter to the winding direction V, with the toothing means 25, 351 axially deflecting relative to one another. In the embodiment as per FIGS. 33A, 33B, the toothing means 25, 351 are thus not locked relative to one another either in the winding direction V or counter to the winding direction V, but rather can slide over one another in the manner of a ratchet if the torque acting between the toothing means 25, 351 is sufficiently high.

In an embodiment illustrated in FIGS. 34A-34D, the teeth of the toothing means 25, 351 extend, at their tooth backs, as in the case of a conical gearwheel, obliquely relative to the winding direction V and also relative to the closing direction X, which can increase the size of those surfaces of the teeth of the toothing means 25, 351 which are in engagement with one another and supported on one another in the event of load acting counter to the winding direction V.

FIGS. 35 to 68 show different exemplary embodiments of uses of a fastener device 1 which may be designed according to an exemplary embodiment of the type described above.

Figure 35:
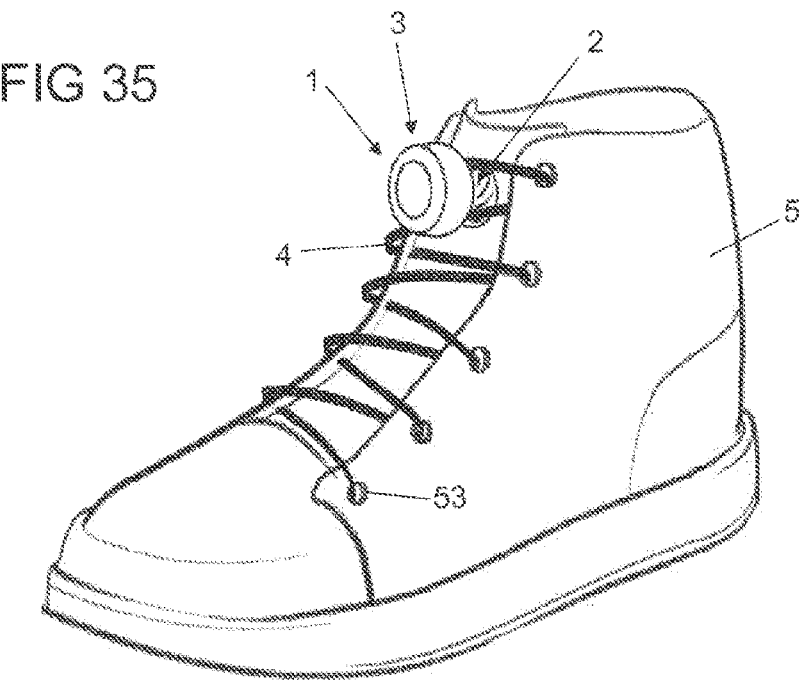
FIG. 35 shows a view of an embodiment of an application of the fastener device for tightening a shoe.

In the exemplary embodiment as per FIG. 35, the fastener device 1 serves for closing and tightening a shoe 5. The fastener part 3 may, for this purpose, be mounted onto the fastener part 2 on a tongue of the shoe 5 in order to tighten a tension element 4 in the form of a shoelace.

Figure 36:
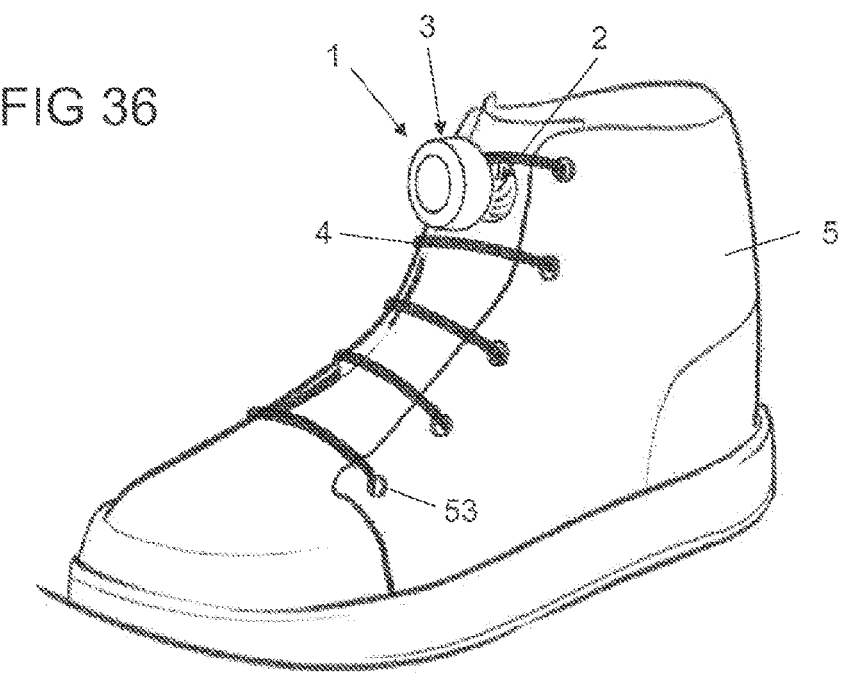
FIG. 36 shows a view of another embodiment of an application of the fastener device for tightening a shoe.

FIG. 36 shows another exemplary embodiment of a shoe 5, which differs from the exemplary embodiment as per FIG. 35 in terms of the winding of the tension element 4 in the form of the shoelace.

In the exemplary embodiment as per FIGS. 35 and 36, one end of the tension element 4 in the form of the shoelace is fixed to the fastener part 3 of the fastener device 1 and can be tightened by rotation of the actuating element 34 together with the winding element 35 relative to the fastener part 2. The tightening is in this case also possible manually by virtue of the fastener part 3 being pulled, and the tension element 4 in the form of the shoelace thereby being tightened, before the fastener part 3 is fixed to the fastener part 2.

Figure 37:
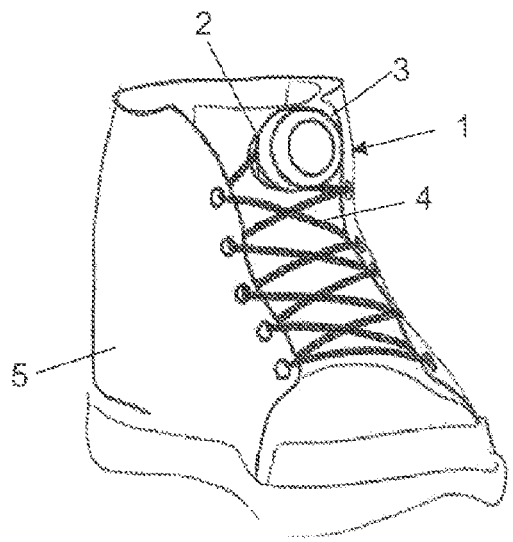
FIG. 37 shows a view of yet another embodiment of an application of the fastener device for tightening a shoe.
Figure 38:
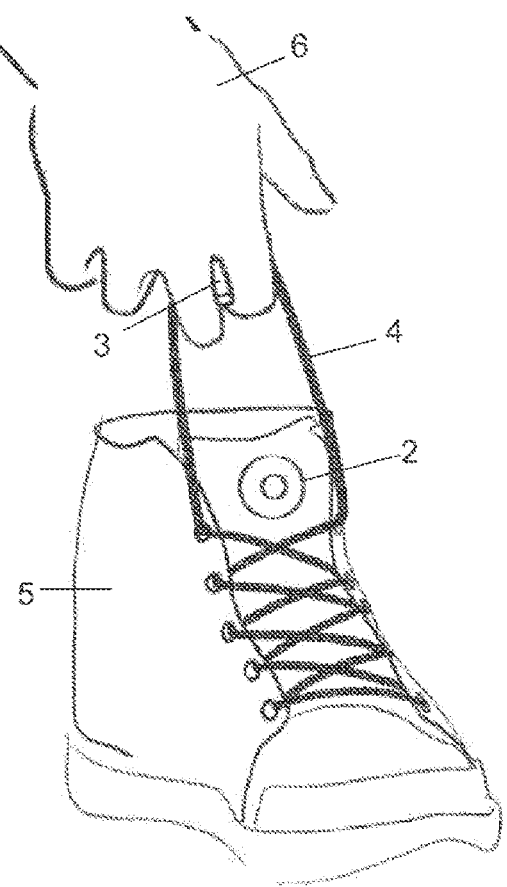
FIG. 38 shows a view of the embodiment as per FIG. 37 during the tightening of the shoe.
Figure 39:
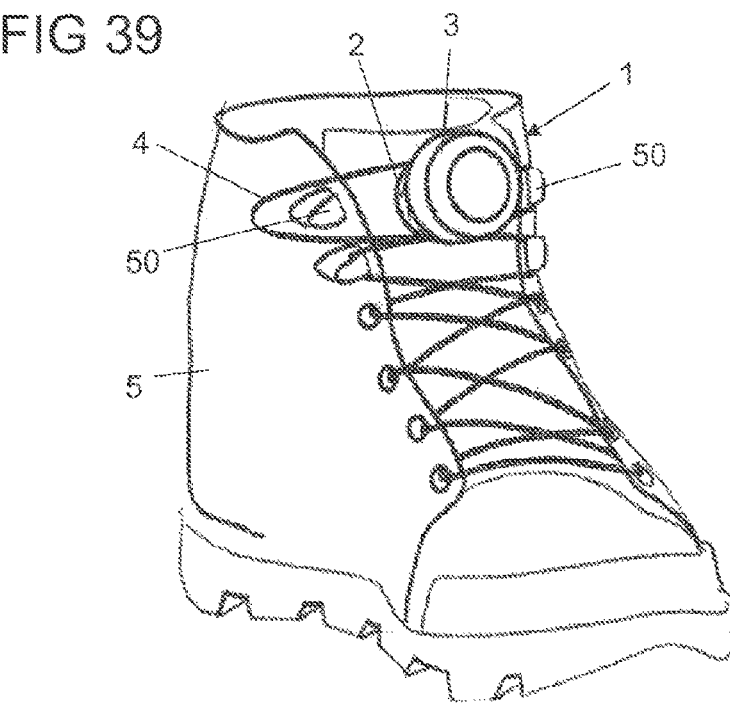
FIG. 39 shows a view of yet another embodiment of an application of the fastener device for tightening a shoe.

In the exemplary embodiment as per FIGS. 37 and 38, two ends of the tension element 4 in the form of the shoelace, which in this case is wound as a loop, are connected to the fastener part 3 of the fastener device 1, such that, by rotation of the fastener part 3 relative to the fastener part 2, the tension element 4 in the form of the shoelace can be wound up with two ends and thus tightened. As illustrated in FIG. 38, before the fastener part 3 is arranged on the fastener part 2, it is possible to perform manual tightening of the tension element 4 by pulling on the tension element 4 using a hand 6.

In the exemplary embodiment as per FIG. 39, it is again the case that two ends of the tension element 4 in the form of the shoelace are connected to the fastener part 3 of the fastener device 1 and can thus be wound up, in order to close and tighten the shoe 5, by rotating the fastener part 3 relative to the fastener part 2. The tension element 4 in the form of the shoelace is in this case laid around tightening elements 50, such that the shoe 5 can be tightened by winding the tension element 4 onto the winding element 35 of the fastener part 3.

Figure 40:
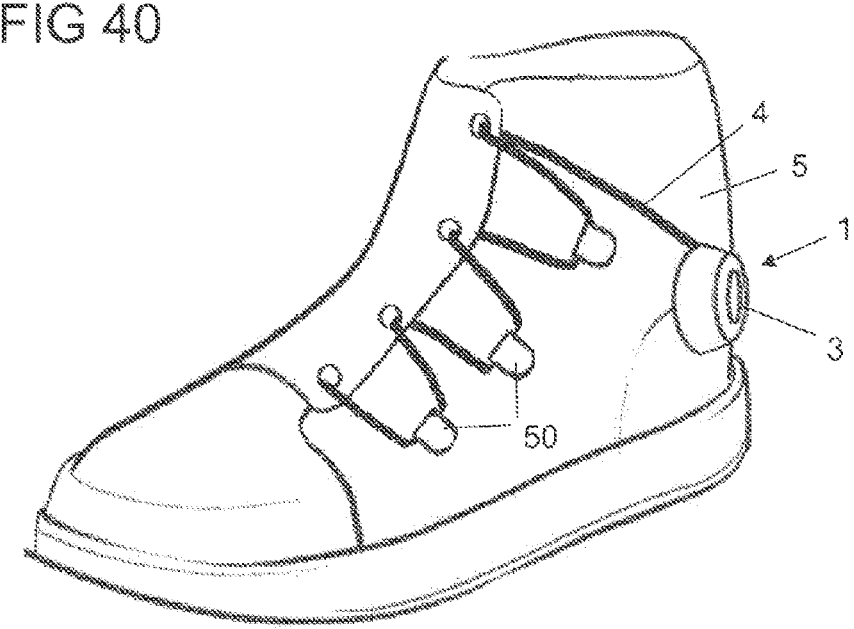
FIG. 40 shows a view of yet another embodiment of an application of the fastener device for tightening a shoe.

FIG. 40 shows another exemplary embodiment, in which the tension element 4 has been laid around tightening elements 50 and is arranged with one end on the fastener part 3 of the fastener device 1 and can thus be tightened by means of the fastener device 1.

Figure 41:
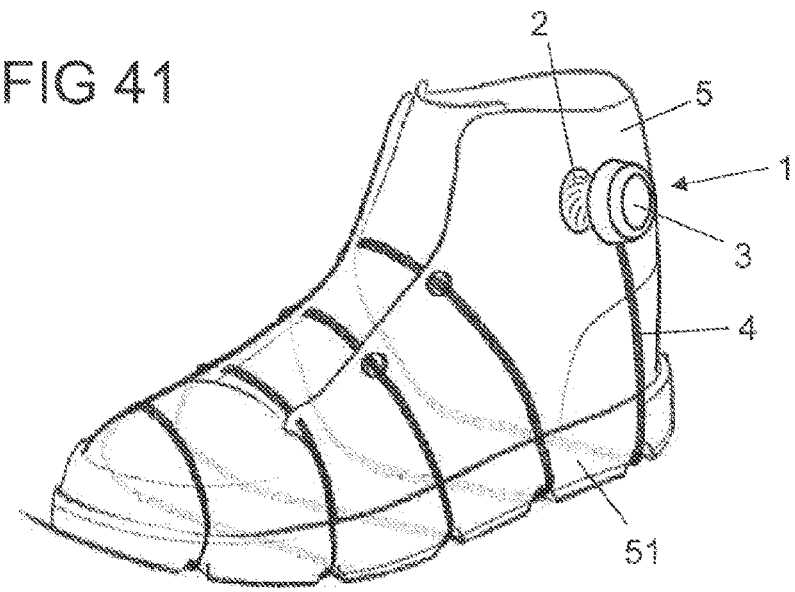
FIG. 41 shows a view of yet another embodiment of an application of the fastener device for tightening a shoe.

In the exemplary embodiment as per FIG. 41, the tension element 4 in the form of the shoelace has (also) been laid around the sole 51 of the shoe 5 and connected by means of one end to the fastener part 3 of the fastener device 1, such that the shoe 5 can be closed and tightened by means of the fastener device 1.

Figure 42:
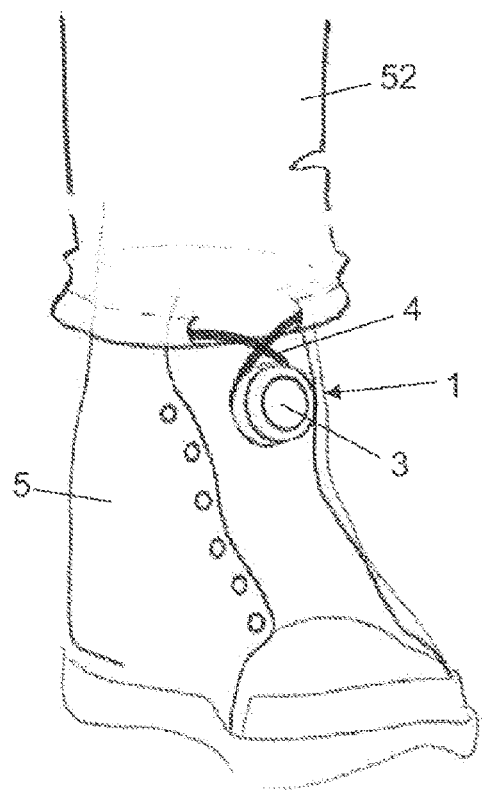
FIG. 42 shows a view of an embodiment of the fastener device for tightening a trouser leg.

In the exemplary embodiment illustrated in FIG. 42, the fastener device 1 serves for bracing a trouser leg 52 together with a shoe 5 by means of a tension element 4 in the form of a band. For this purpose, the tension element 4 extends around the trouser leg 52 and is fixed by means of the fastener device 1 to the shoe 5, such that the trouser leg 52 can be braced relative to the shoe 5 by rotation of the fastener part 3 relative to the fastener part 2.

Figure 43:
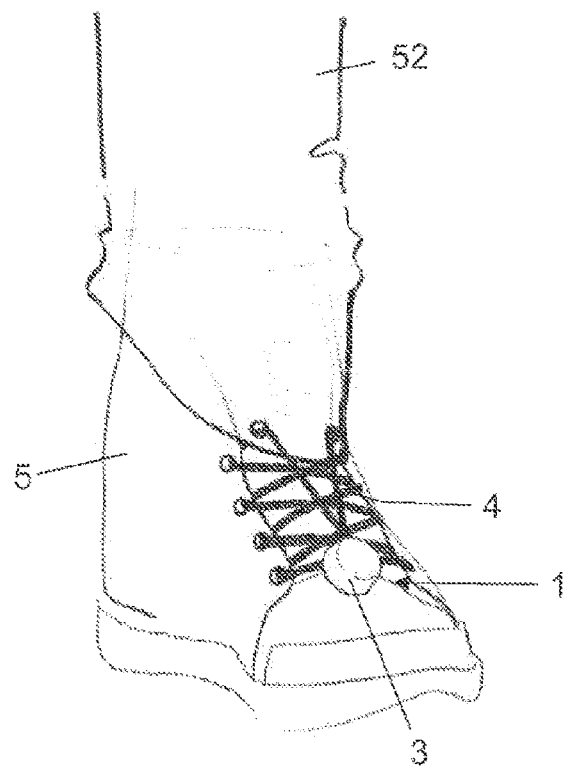
FIG. 43 shows a view of an embodiment of an application of the fastener device for bracing a trouser leg together with a shoe.

Another exemplary embodiment is shown in FIG. 43. In this exemplary embodiment, a trouser leg 52 can again be braced relative to a shoe by virtue of the fact that a tension element 4 which extends through eyelets in the trouser leg 52 can be braced relative to the shoe 5 by means of the fastener device 1.

Figure 44:
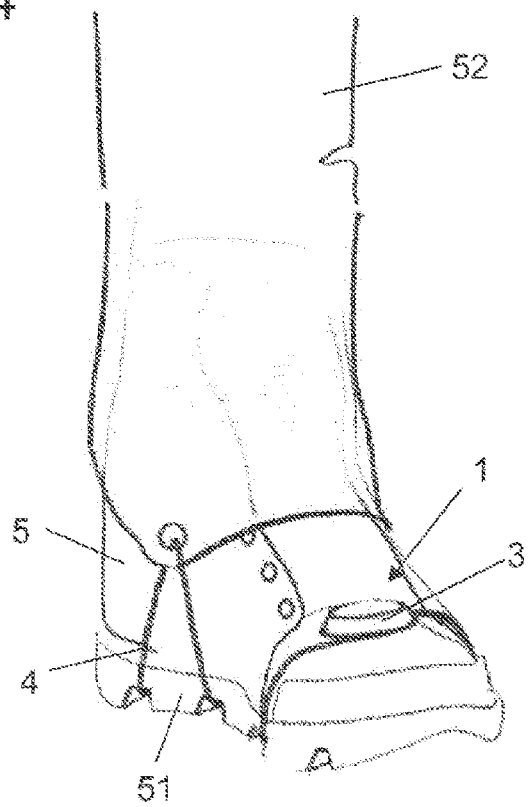
FIG. 44 shows a view of another embodiment of an application of the fastener device for tightening a trouser leg on a shoe.

It is also the case in the exemplary embodiment as per FIG. 44 that a trouser leg 52 can be braced relative to a shoe, wherein, in this case, the tension element 4 extends in the form of a band around the sole 51 of the shoe 5 and can be braced on the shoe 5 by means of the fastener device 1.

Figure 45:
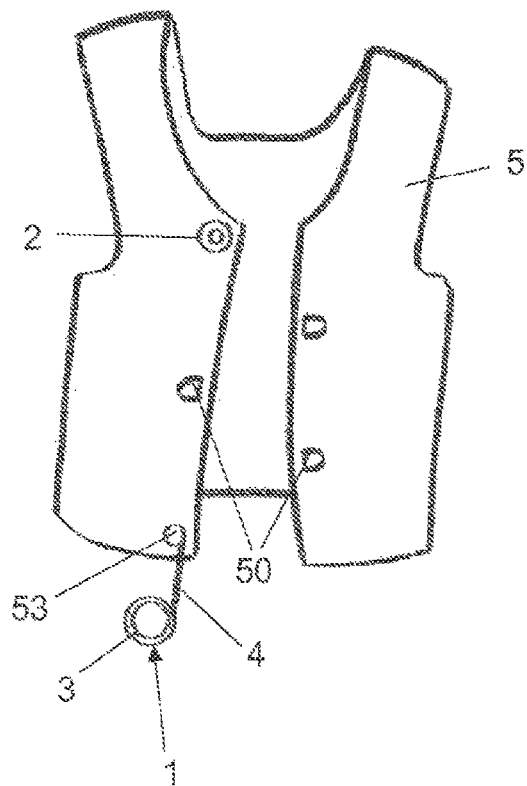
FIG. 45 shows a view of an embodiment of an application of the fastener device for closing an article of clothing.
Figure 46:
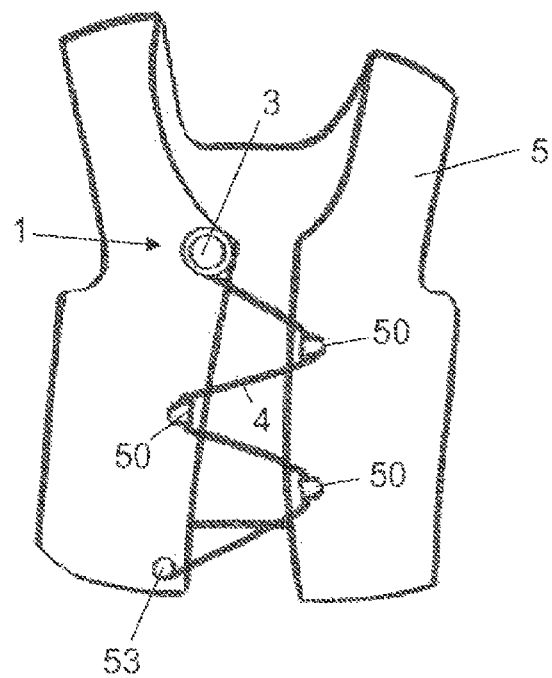

In the exemplary embodiment as per FIGS. 45 and 46, the fastener device 1 serves for closing and tightening an article of clothing 5, for example a vest or a jacket. The tension element 4 in the form of a band or a cord is fixed at a fastening point 53 to the article of clothing 5 and can be laid around tightening elements 50 on both sides of an opening slot of the article of clothing 5 in order to thereby close the article of clothing 5 as illustrated in FIG. 46. By virtue of the fastener part 3 being arranged on the fastener part 2 and the fastener part 3 being rotated relative to the fastener part 2, the article of clothing 5 can then be tightened.

Figure 47:
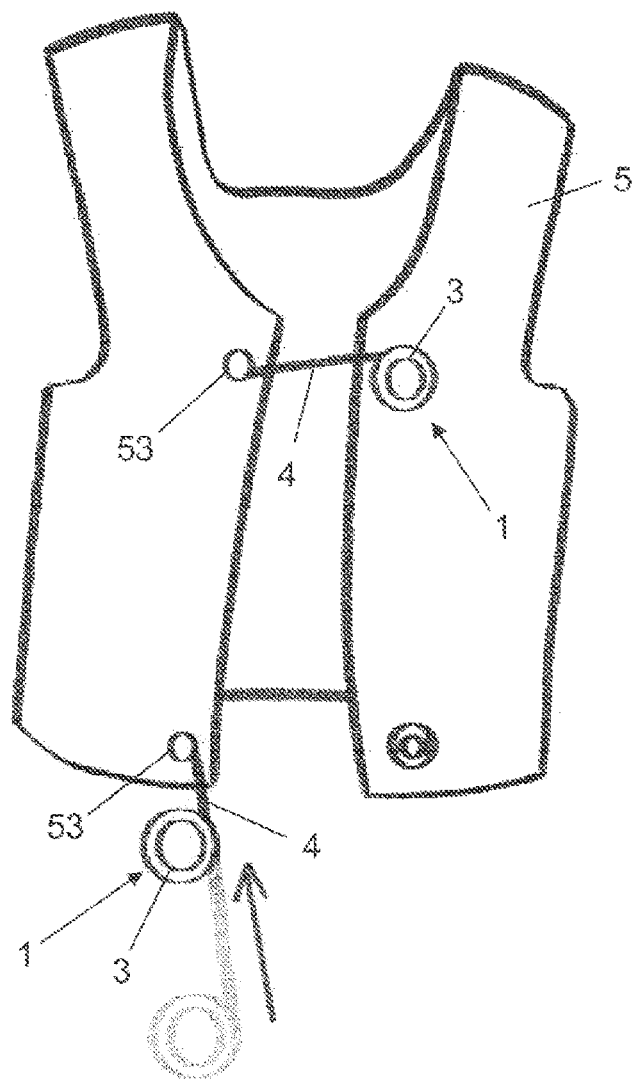

It is also the case in the exemplary embodiment as per FIG. 47 that the fastener device 1 serves for closing an article of clothing 5, wherein, in this case, two fastener devices 1 are provided for tightening two tension elements 4. The tension elements 4 are fixed in each case on one side of the opening slot of the article of clothing 5 at a fastening point 53 and can be tightened by virtue of the respective fastener part 3 being arranged on the associated fastener part 2 of the fastener device 1 on the other side of the opening slot of the article of clothing 5.

Figure 48:
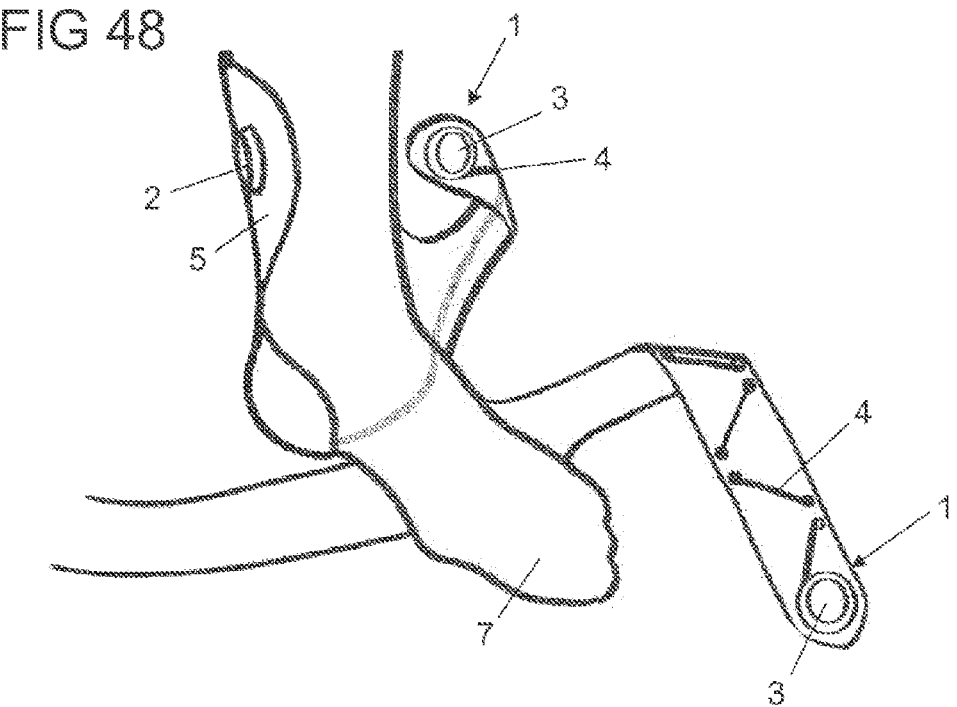
Figure 49:
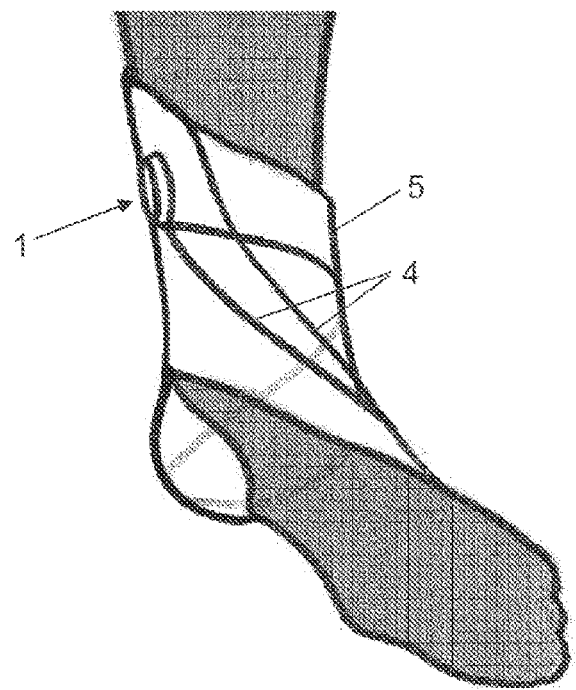

In the exemplary embodiment as per FIGS. 48 and 49, the fastener device 1 serves for closing and tightening a medical aid 5 in the form of an ankle bandage on a foot 7. By virtue of the fastener part 3, which is connected to one end of the ankle bandage, being arranged on the fastener part 2, which is connected to another end of the ankle bandage, and the tension element 4 extending on the ankle bandage being tightened, the ankle bandage can be closed and tightened.

Figure 50:
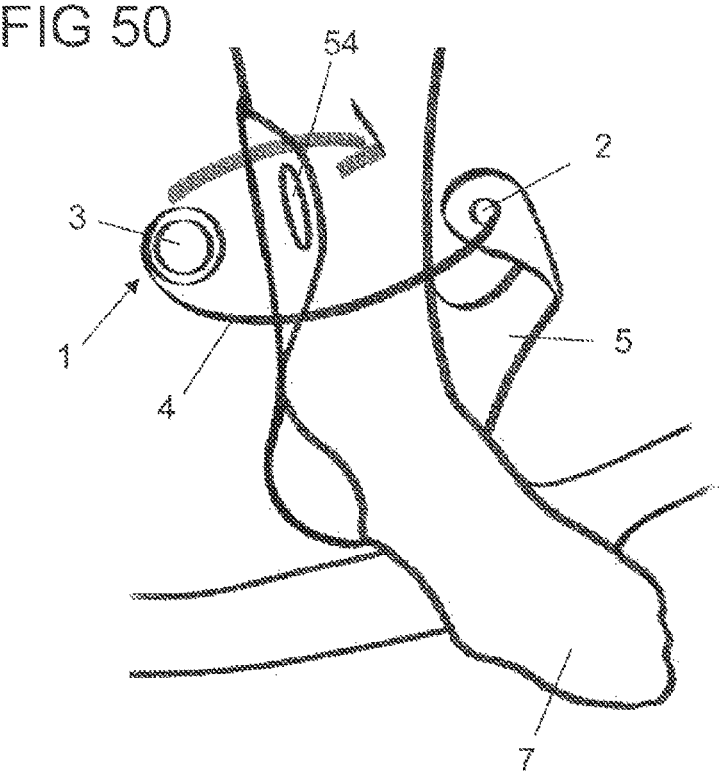
Figure 51:
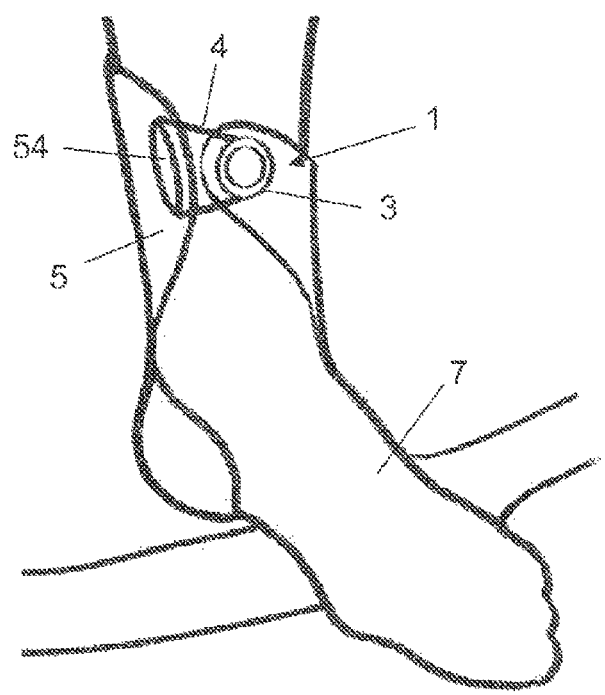

FIGS. 50 and 51 show another exemplary embodiment of a medical aid 5 in the form of an ankle bandage, in the case of which the tension element 4, which is connected at one end to the fastener part 2 and at another end to the fastener part 3, can be laid around a diverting means 54, and, by mounting the fastener part 3 on the fastener part 2, a loop of the tension element 4 is thus formed, which can be tightened by rotating the fastener part 3 relative to the fastener part 2 in order to close and tighten the ankle bandage.

Figure 52:
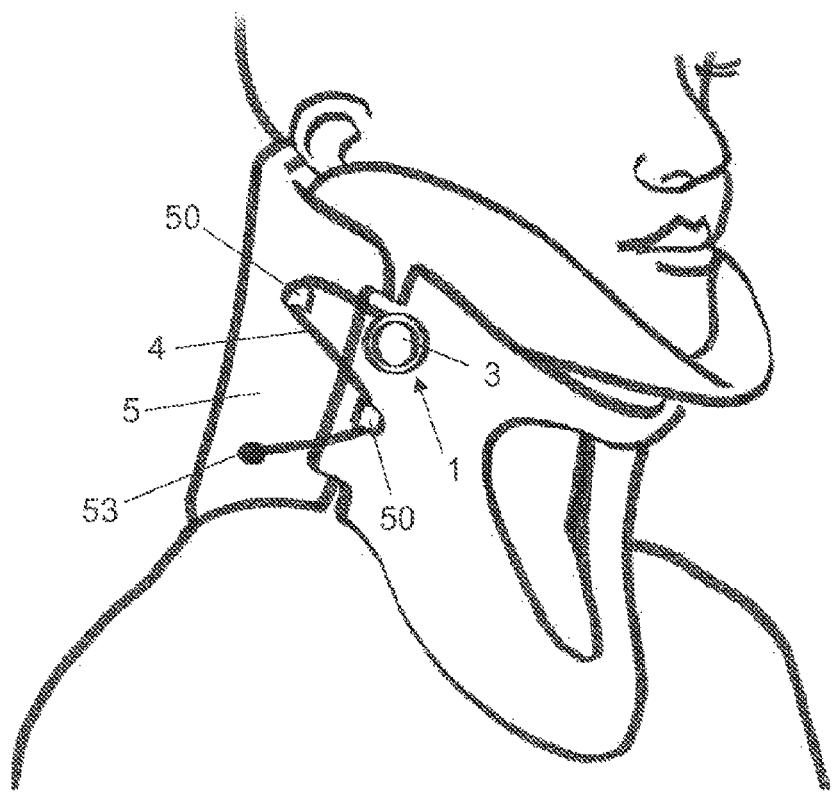

FIG. 52 shows an exemplary embodiment of a medical aid 5 in the form of an orthosis in the form of a neck brace, in the case of which the fastener device 1 serves for closing and tightening. A tension element 4 connected to the fastener part 3 can, proceeding from a fastening point 53, be laid around tightening hooks 50 and tightened by rotation of the fastener part 3 relative to the fastener part 2.

Figure 53:
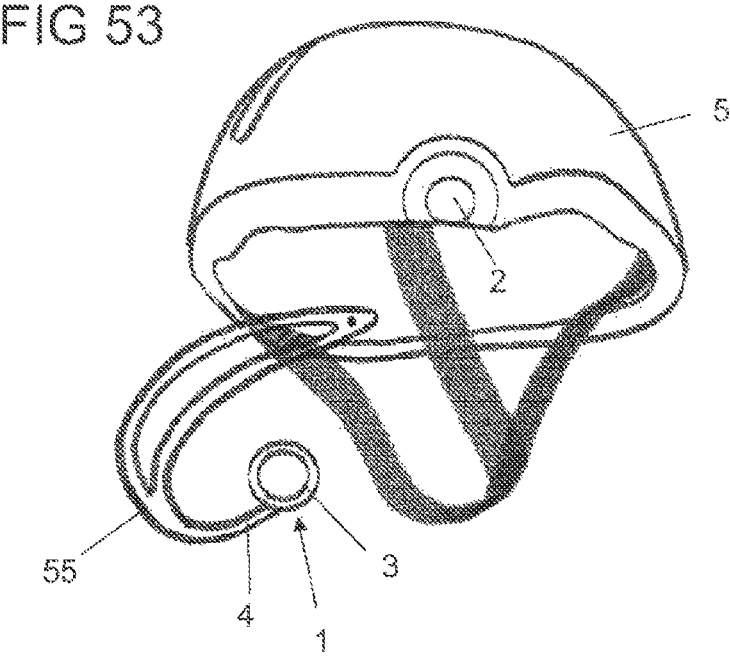
Figure 54:
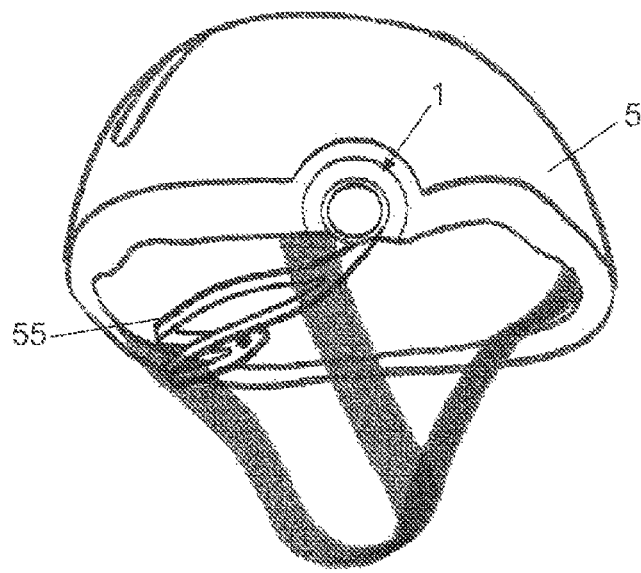

FIGS. 53 and 54 show an exemplary embodiment of a helmet 5, for example of a bicycle helmet, in the case of which the fastener device 1 serves for closing and tightening a belt 55. The tension element 4 is a constituent part of the belt 55 and can be wound onto the fastener part 3, specifically the winding element 35 of the fastener part 3, in order to thereby tighten the belt 55.

Figure 55:
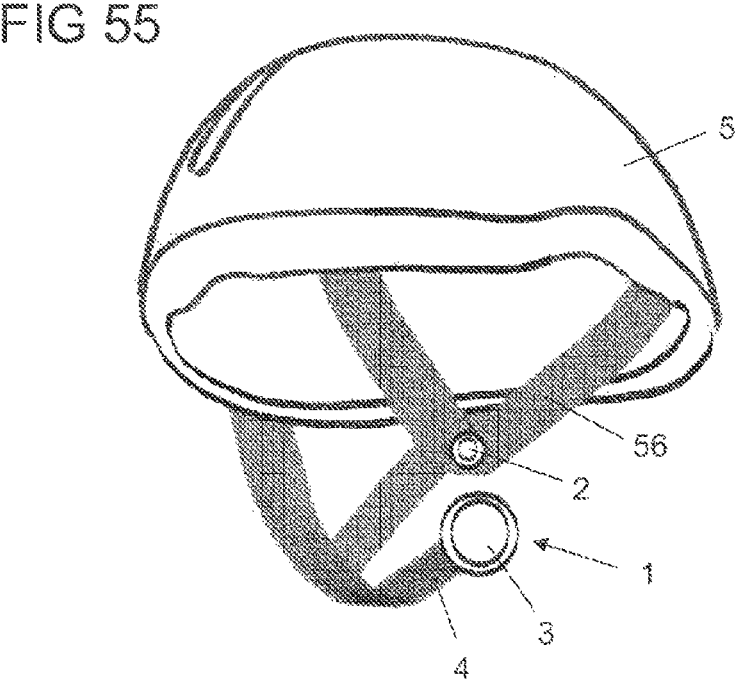
Figure 56:
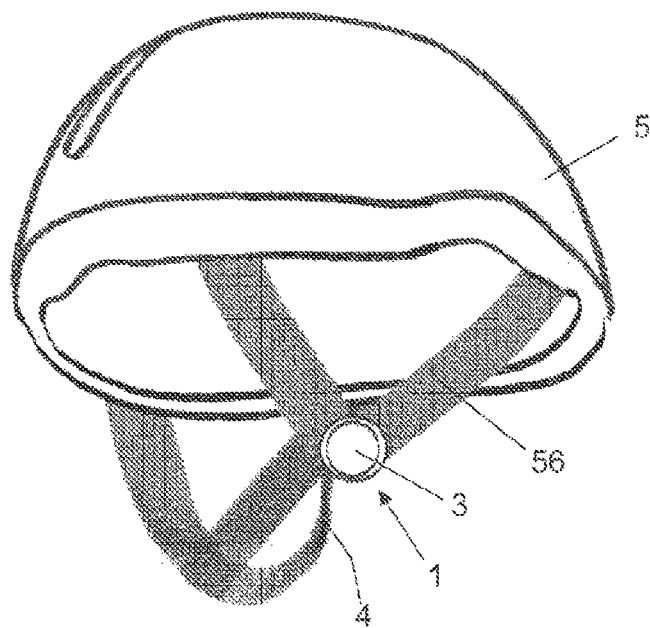

In the exemplary embodiment as per FIGS. 55 and 56, the fastener device 1 serves for tightening a chin strap 56 of a helmet 5, for example of a bicycle helmet. The fastener part 3 of the fastener device 1 may in this case be arranged on the fastener part 2 and rotated relative to the fastener part 2 in order to thereby tighten the strap 56.

Figure 57:
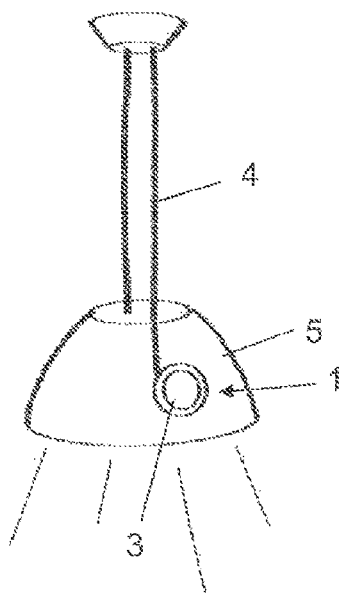

In the exemplary embodiment as per FIG. 57, the fastener device 1 serves for adjusting the height of an assembly 5 in the form of a lamp. The tension element 4 serves in this case for hanging the lamp. By rotating the fastener part 3 of the fastener device 1, the length of the tension element 4 can be varied, and thus the height of the lamp can be adjusted.

In the exemplary embodiment as per FIG. 58, the fastener device 1 serves for hanging an assembly 5 in the form of a picture. By rotating the fastener part 3, the length of the tension element 4 can be changed, and thus the hanging of the picture can be adapted.

In the exemplary embodiment illustrated in FIGS. 59 to 61, the fastener device 1 serves for the electrical connection of an assembly in the form of a lamp 5. For this purpose, the fastener part 2 is in the form of a plug. The fastener part 3 can be rotated relative to the fastener part 2 in the form of the plug in order to thereby change the freely extending length of the electrical cable that forms the tension element 4.

In the exemplary embodiment as per FIG. 62, the fastener device 1 serves for tensioning an assembly 5 in the form of a roller blind. The fastener part 3 is connected by means of the tension element 4 to the roller blind. By virtue of the fastener part 3 being arranged on the fastener part 2, which is arranged for example on a frame, and being rotated, the tension element 4 can be wound up and the roller blind thus adjusted.

In the exemplary embodiment as per FIG. 63, by contrast to the exemplary embodiment as per FIG. 62, two ends of the tension element 4 are connected to the fastener part 3, such that, by rotation of the fastener part 3, the two ends of the tension element 4 can be simultaneously wound up onto the winding element 35 of the fastener part 3.

In an exemplary embodiment illustrated in FIG. 64, the fastener device 1 serves for tightening a tension element 4 in the form of a strap on an article of luggage.

In an exemplary embodiment illustrated in FIG. 65, the fastener device 1 serves for tightening a tension element 4 in the form of a band or a cord on an article of luggage in the form of a rucksack, in order to thereby secure articles to the article of luggage.

In an exemplary embodiment illustrated in FIG. 66, the fastener device 1 serves for securing an article 5, for example a mobile telephone or the like, on a bicycle, in particular to a handlebar of a bicycle. The tension element 4 is in this case looped around the article 5 and can be tightened by being wound, in certain portions, onto the winding element 35 of the fastener part 3.

FIG. 67 shows another exemplary embodiment with different winding of the tension element 4 in order to secure an article 5, for example a mobile telephone, on a bicycle.

In an exemplary embodiment illustrated in FIG. 68, the fastener device 1 serves for securing an article, for example an article of luggage, in a load compartment of a vehicle. Here, the tension element 4 is laid across the article of luggage and thereby holds the article of luggage positionally fixed on the floor of the load compartment. By means of the fastener device 1, the tension element 4 can be tightened in order to secure the article of luggage.

FIGS. 69 to 73 show a further exemplary embodiment of a fastener device 1, in the case of which the fastener parts 2, 3 can be mounted on one another along a closing direction X and are held against one another in a closed position.

In the exemplary embodiment as per FIGS. 69 to 73, the tension element 4 is in the form of a strap which can be wound up onto a winding element 35 in the form of a sleeve of the fastener part 3. The fastener part 3 can be mounted onto the fastener part 2, which has for example a buckle, such that, by means of the fastener device 1, ends of the tension element 4 can be connected to one another and tightened relative to one another.

The fastener part 3 has an actuating element 34 with a hand lever formed integrally thereon, which hand lever can, by an engagement means 345, be placed in engagement with an engagement means 355 of the winding element 35, such that, by means of the actuating element 34, the winding element 35 can be rotated in a winding direction V relative to the fastener part 2.

As can be seen in particular from the sectional view in FIG. 73, the actuating element 34 has a peg 346 with an engagement opening 347, by means of which the actuating element 34 can be mounted in the closing direction X onto a cylinder portion 201 on a body 20 of the fastener part 2 in order to connect the fastener parts 2, 3 to one another.

For example owing to a spring preload between the actuating element 34 and the winding element 35, the engagement means 345, 355 are not in engagement with one another when the fastener parts 2, 3 are separated from one another. The winding element 35 can thus be freely rotated relative to the actuating element 34, such that the tension element 4 can for example be unwound from the winding element 35. For closing, the fastener part 3 is mounted onto the fastener part 3 such that the engagement opening 347 on the peg 346 of the actuating element 34 engages with the cylinder portion 201 of the fastener part 2, wherein the winding element 35 is supported on the body 20 of the fastener part 2 and, owing to magnetic attraction of magnet elements 23, 33 on the cylinder portion 201, on the one hand, and on the peg 346 of the actuating element 34, on the other hand (see FIG. 73), the actuating element 34 is pulled toward the winding element 35 and the engagement means 345, 355 thus engage with one another in positively locking fashion. In this way, an operative connection is produced between the actuating element 34 and the winding element 35, such that, when the fastener parts 2, 3 have been connected to one another, the actuating element 34 and the winding element 35 can be jointly rotated in order to thereby wind the tension element 4 onto the winding element 35 and thereby tighten the tension element 4.

At an end facing toward the body 20, the winding element 35 has a toothing means 351 in the form of a sawtooth-like toothing which, when the fastener parts 2, 3 have been connected to one another, engages with a toothing means 25 on the body 20. The engagement of the toothing means 25, 351 has the effect that the fastener parts 2, 3 can be rotated relative to one another in the winding direction V, in order to tighten the tension element 4 on the winding element 35, but not counter to the winding direction V.

To release the fastener device 1, the fastener parts 2, 3 can be pulled apart from one another counter to the closing direction X, such that the fastener parts 2, 3 are thereby separated from one another.

FIGS. 74A and 74B show the fastener device 1 in the case of separated fastener parts 2, 3 (FIG. 74A) and in the case of a closed fastener device 1 (FIG. 74B). The fastener device 1 may serve for tightening a strap in the form of a waistbelt.

FIG. 75 shows a further exemplary embodiment of a fastener device 1, in the case of which fastener parts 2, 3 can be mounted on one another in a closing direction X, in a manner similar to that described above.

In the exemplary embodiment as per FIG. 75, a gearing 26 is provided on the fastener part 2, which gearing may be in the form of a bevel gearing or worm gearing and serves for rotating the fastener part 3 relative to the fastener part 2, in order to thereby tighten the tension element 4, via the toothing means 25 (which, when the fastener parts 2, 3 have been connected to one another, engages with the toothing means 351 of the fastener part 3, as can be seen for example from FIG. 69). In the embodiment as per FIG. 75, a rotation of the fastener parts 2, 3 relative to one another is thus realized via a gearing provided on the fastener part 2, which can be actuated manually.

FIGS. 76 to 79A, 79B show a further exemplary embodiment, in which precisely such a gearing 26 is implemented for the tightening of the winding element 35.

In the exemplary embodiment as per FIGS. 76 to 79A, 79B, the gearing 26 is designed as a tightening gearing, in the case of which a tightening lever 260 is mounted, so as to be pivotable about a pivot axis 265, on the body 20 of the fastener part 2 and is preloaded relative to the body 20 into a basic position (illustrated in FIGS. 79A, 79B) by means of a spring element 261.

In the exemplary embodiment, the fastener part 3 may be mounted with a winding element 35 onto a cylinder portion 201 of the body 20 and, in a connected position, engages by a toothing means 351 with an associated toothing means 25 of the body 20, as has also been described above. On the winding element 35, there is formed a tightening engagement means 356 in the form of a toothing which runs around the winding element 35 and serves for interacting with the gearing 26.

On the tightening lever 260 of the gearing 26, an engagement lever 262 is arranged so as to be pivotable about a pivot axis 263, which engagement lever serves for engaging into the tightening engagement means 356 of the winding element 35.

For the mounting of the fastener parts 2, 3 on one another, the tightening lever 260 can, as illustrated in FIGS. 78A, 78B, be deflected out of the basic position in a pivoting direction P1 in order to thereby move the engagement lever 262 out of a region assumed by the winding element 35 when the fastener parts 2, 3 have been connected to one another. The fastener parts 2, 3 can thus be readily mounted on one another without being impeded by the gearing 26.

If the tightening lever 260 is released again, the gearing 26 passes with its tightening lever 260 into the basic position as per FIGS. 79A, 79B, in which the engagement lever 262 engages with the tightening engagement means 256.

If the tightening lever 260 is now deflected in a pivoting direction P2, then the engagement lever 262 is moved jointly and rotates the winding element 35 in the winding direction V, such that the tension element 4 is wound onto the winding element 35. The tension element 4 is thus tightened.

Here, the tightening is performed in stepwise fashion. Owing to the spring element 261 and the spring preload provided by it, the tightening lever 260 is, after an actuation, automatically reset into the basic position, wherein the engagement lever 262 slides over the tightening engagement means 356, with elastic deflection of the spring element 264 by means of which the engagement lever 262 is elastically preloaded relative to the tightening lever 260. The tightening of the tension element 4 is thus performed in stepwise fashion by repeated actuation of the tightening lever 260.

By means of the spring element 264, a freewheel is also provided. The winding element 35 can also be rotated by hand in the winding direction V. Here, the engagement means 262 slides over the tightening engagement means 356 of the winding element 35 with elastic deflection of the spring element 264.

The concept on which the solution is based is not restricted to the embodiments highlighted above, but may also be realized in a fundamentally different form.

A fastener device of the type described here combines a mechanical fastener and a winding means. Fastener parts can be mounted onto one another and are held against one another in a closed position. Here, by means of a winding element, a tension element can be wound up and thus tightened, such that assemblies can be connected to one another and tightened relative to one another.

The tension element is generally configured as a flexible element which is suitable (exclusively) for transmitting tensile forces. The tension element may be a cable, strap, belt or band.

Fastener devices of the type described here may be designed as purely mechanical fastener devices without the use of magnet elements. The use of magnet elements may however be advantageous in order to firstly achieve simple intuitive handleability and secondly improve the hold between the fastener parts.

The fastener device may basically realize fundamentally different magnetic-mechanical detent fasteners. The fastener device may—with regard to its magnetic-mechanical detent function—be designed as described in WO 2008/006357 A2, WO 2008/006354 A2, WO 2009/092368 A2, WO 2010/006594 A2, WO 2008/006356 A2, WO 2009/010049 A2, WO 2009/127196 A2, WO 2014/090926 A1 and in the international application with the file reference PCT/EP2013/060762.

LIST OF REFERENCE DESIGNATIONS

1 Fastener device
2 Fastener part
20 Main body
200 Side wall
201 Cylinder collar
202 Apertures 203 Detent recess (detent groove)
21 Undercut element
22 Undercut element
23 Magnet element
24 Blocking element
240 Axle element
241 Spring element
25 Toothing means
250 Toothing element
251 Ring
252 Projection element
253 Run-on bevel
254 Tooth flank
255 Detent lug
26 Gearing means
260 Tightening lever
261 Spring element
262 Engagement lever
263 Pivot axis
264 Spring element
265 Pivot axis
3 Fastener part
30 Housing element
300 Cylinder collar
301 Interior space
302 Toothing
303 Dome
304 Opening
305 Detent groove
31 Undercut element
32 Undercut element
33 Magnet element
34 Actuating element
340 Body
341 Toothing means
342 Peg
343 Locking element
344 Spring element
345 Engagement means
346 Peg
347 Opening
35 Winding element
350 Winding body
351 Toothing means
352 Opening
353 Channel
355 Engagement means
356 Tightening engagement means
36 Detent element
360 Detent projection
37 Detent means
370 Detent element
371 Detent projection
372 Run-on element
373 Preload element (ring)
374 Spring element
375 Operating element
376 Run-on element
38 Engagement element
380 Body
381 Annular collar
382 Receiving opening
383 Opening
384 Spring element
385 Detent element
386 Spring element
387 Opening
39 Operating element
390 Body
391 Annular collar
392 Unlocking opening
393 Opening
394 Spring element
4 Tension element
5 Assembly
50 Tightening hook
51 Sole
52 Trouser leg
53 Securing point
54 Diverting means
55 Belt
56 Strap
6 Hand
7 Foot
B Loading direction
D Actuating direction
E Engagement direction
L Release direction
P1, P2 Pivoting direction
V Winding direction
X Closing direction
Y Opening direction

The invention claimed is:
1. A fastener device, having
a first fastener part and a second fastener part which are mountable on one another along a closing direction, are held against one another in a closed position, and are separable from one another in order to open the fastener device,
wherein the second fastener part comprises a winding element for receiving a tension element, the winding element being rotatable relative to the first fastener part in order to wind up the tension element on the winding element along a winding direction, wherein an axis of rotation for the winding element extends substantially parallel with the closing direction,
wherein the first fastener part and the second fastener part each comprise at least one magnet element, the at least one magnet element of the first fastener part and the at least one magnet element of the second fastener part being configured to provide a magnetic attraction force when mounting the first fastener part and the second fastener part on one another, and
wherein one of the fastener parts has a cylinder collar, which engages into the other of the fastener parts for a rotatable mounting of the fastener parts on one another.
2. The fastener device as claimed in claim 1, wherein at least one of the following:
the winding element is rotatable relative to the first fastener part around the closing direction,
the winding element, in the closed position, is rotatable relative to the first fastener part,
the winding element, in the closed position, is rotatable relative to the first fastener part in the winding direction but not counter to the winding direction, and
the winding element, in the closed position, is not rotatable relative to the first fastener part.
3. The fastener device as claimed in claim 1, wherein the winding element has a toothing means which, in the closed position, engages with a toothing means of the first fastener part.
4. The fastener device as claimed in claim 3, wherein at least one of the following:

the toothing means of the winding element, in the closed position, is movable relative to the toothing means of the first fastener part in the winding direction, but a movement counter to the winding direction is locked, and at least one of the toothing means has at least one toothing element which, in an event of rotation of the winding element in the winding direction, can be forced aside transversely with respect to the winding direction.

5. The fastener device as claimed in claim 1, wherein the first fastener part and the second fastener part are, in the closed position, mechanically detained together in order to hold the fastener parts against one another counter to the closing direction.

6. The fastener device as claimed in claim 5, wherein one of the fastener parts has a detent means with at least one movable detent element which, in a detained position, engages into a detent recess of the other fastener part and thus holds the fastener parts against one another counter to the closing direction.

7. The fastener device as claimed in claim 6, wherein at least one of the following:
  the detent means moves automatically into the detained position during the mounting of the fastener parts,
  the at least one movable detent element is spring-preloaded in a direction of the detained position, and
  the detent means has an operating element which can be actuated in order to disengage the at least one movable detent element from the detent recess.

8. The fastener device as claimed in claim 1, wherein the second fastener part has a housing element which, in the closed position, is arranged on the first fastener part and on which the winding element is rotatably mounted.

9. The fastener device as claimed in claim 8, wherein the first fastener part has at least one first undercut element and the housing element of the second fastener part has at least one second undercut element, wherein the at least one first undercut element and the at least one second undercut element engage with one another during the mounting of the fastener parts, such that the fastener parts are, in the closed position, held on one another counter to the closing direction.

10. The fastener device as claimed in claim 9, wherein at least one of the following:
  at least two first undercut elements are arranged, offset with respect to one another transversely with respect to the closing direction, on a main body of the first fastener part, and/or at least two second undercut elements are arranged, offset with respect to one another transversely with respect to the closing direction, on the housing element of the second fastener part, and
  the at least one first undercut element and/or the at least one second undercut element, viewed in a plane transverse with respect to the closing direction, are arcuate or V-shaped.

11. The fastener device as claimed in claim 9, wherein one of the fastener parts has a blocking element for safeguarding an engagement between the at least one first undercut element and the at least one second undercut element in the closed position of the fastener parts.

12. The fastener device as claimed in claim 11, wherein the blocking element, in a blocking position in which the engagement between the at least one first undercut element and the at least one second undercut element is safeguarded in the closed position of the fastener parts, faces toward a component of the other fastener part such that the at least one first undercut element and the at least one second undercut element are held in the engagement.

13. A fastener device, comprising:
  a first fastener part and a second fastener part which are mountable on one another along a closing direction, are held against one another in a closed position, and are separable from one another in order to open the fastener device,
  wherein the second fastener part comprises a winding element for receiving a tension element, the winding element being rotatable relative to the first fastener part in order to wind up the tension element on the winding element along a winding direction,
  wherein the first fastener part and the second fastener part each comprise at least one magnet element, the at least one magnet element of the first fastener part and the at least one magnet element of the second fastener part being configured to provide a magnetic attraction force when mounting the first fastener part and the second fastener part on one another,
  wherein the second fastener part has a housing element which, in the closed position, is arranged on the first fastener part and on which the winding element is rotatably mounted, and
  wherein the second fastener part has a locking assembly which, in a locked state, locks the winding element such that the winding element is rotatable relative to the housing element in the winding direction but not counter to the winding direction.

14. The fastener device as claimed in claim 13, wherein at least one of the following:
  the locking assembly can be unlocked from the locked state, such that the winding element is rotatable relative to the housing element counter to the winding direction, and
  the locking assembly is automatically unlocked during an opening of the fastener device.

15. The fastener device as claimed in claim 13, wherein the locking assembly has an actuating element which is arranged rotatably on the housing element.

16. The fastener device as claimed in claim 15, wherein the housing element and the actuating element are operatively connected by a freewheel means, such that the actuating element is rotatable relative to the housing element in the winding direction but not counter to the winding direction.

17. The fastener device as claimed in claim 15, wherein the actuating element has a first toothing means and the winding element has a second toothing means.

18. A fastener device, comprising:
  a first fastener part and a second fastener part which are mountable on one another along a closing direction, are held against one another in a closed position, and are separable from one another in order to open the fastener device,
  wherein the second fastener part comprises a winding element for receiving a tension element, the winding element being rotatable relative to the first fastener part in order to wind up the tension element on the winding element along a winding direction,
  wherein the first fastener part and the second fastener part each comprise at least one magnet element, the at least one magnet element of the first fastener part and the at least one magnet element of the second fastener part being configured to provide a magnetic attraction force when mounting the first fastener part and the second fastener part on one another, wherein the second fastener part has a housing element which, in the closed position, is arranged on the first fastener part and on which the winding element is rotatably mounted, wherein the first fastener part has at least one first undercut element and the housing element of the second fastener part has at least one second undercut element, wherein the at least one first undercut element and the at least one second undercut element engage with one another during the mounting of the fastener parts, such that the fastener parts are, in the closed position, held on one another counter to the closing direction, wherein one of the fastener parts has a blocking element for safeguarding an engagement between the at least one first undercut element and the at least one second undercut element in the closed position of the fastener parts, wherein the blocking element, in a blocking position in which the engagement between the at least one first undercut element and the at least one second undercut element is safeguarded in the closed position of the fastener parts, faces toward a component of the other fastener part such that the at least one first undercut element and the at least one second undercut element are held in the engagement, and wherein at least one of the following:
- the blocking element is spring-preloaded in a direction of the blocking position,
- the blocking element is, for an opening of the fastener device, adjustable out of the blocking position, and
- the component of the other fastener part is adjustable in order to eliminate a blocking action of the blocking element.

* * * * *